(12) United States Patent
Curtis et al.

(10) Patent No.: US 8,466,115 B2
(45) Date of Patent: Jun. 18, 2013

(54) SPIROCYCLIC ISOXAZOLINE DERIVATIVES AS ANTIPARASITIC AGENTS

(75) Inventors: Michael Curtis, Portage, MI (US);
Sanjay Menon, Kalamazoo, MI (US);
Valerie A. Vaillancourt, Portage, MI (US); Nathan Anthony Logan Chubb, Richland, MI (US); Denis Billen, Kalamazoo, MI (US); Sean David William Greenwood, Kalamazoo, MI (US); Timothy Lee Stuk, Mattawan, MI (US)

(73) Assignee: Zoetis LLC, Florham Park, NJ (US)

( * ) Notice: Subject to any disclaimer, the term of this patent is extended or adjusted under 35 U.S.C. 154(b) by 0 days.

(21) Appl. No.: 13/414,764

(22) Filed: Mar. 8, 2012

(65) Prior Publication Data

US 2012/0232026 A1   Sep. 13, 2012

Related U.S. Application Data

(60) Provisional application No. 61/490,804, filed on May 27, 2011, provisional application No. 61/489,913, filed on May 25, 2011, provisional application No. 61/451,256, filed on Mar. 10, 2011.

(51) Int. Cl.
*A61K 31/422* (2006.01)
*A61P 33/14* (2006.01)
*C07D 491/10* (2006.01)

(52) U.S. Cl.
USPC .................. 514/30; 514/210.18; 548/240

(58) Field of Classification Search
None
See application file for complete search history.

(56) References Cited

U.S. PATENT DOCUMENTS

| | | | |
|---|---|---|---|
| 5,554,753 | A | 9/1996 | O'Donnell et al. |
| 7,947,715 | B2 | 5/2011 | Mita et al. |
| 2010/0069351 | A1 | 3/2010 | Taniguchi et al. |
| 2011/0009438 | A1 | 1/2011 | Mita et al. |
| 2011/0166358 | A1 | 7/2011 | Iwata et al. |

FOREIGN PATENT DOCUMENTS

| | | |
|---|---|---|
| WO | 2007/075459 | 7/2007 |
| WO | 2007/105814 | 9/2007 |
| WO | 2008/096746 | 8/2008 |
| WO | 2008/122375 | 10/2008 |
| WO | 2009/035004 | 3/2009 |
| WO | 2009/063910 | 5/2009 |
| WO | 2010/025998 | 3/2010 |
| WO | 2010/032437 | 3/2010 |
| WO | 2010/084067 | 7/2010 |
| WO | 2011/104089 | 9/2011 |

OTHER PUBLICATIONS

Dehmlow et al., "Monodeazacinchona Alkaloid Derivatives: Synthesis and Preliminary Applications as Phase-Transfer Catalysts", Eur. J. Org. Chem., 2002(13):2087-2093, 2002.

*Primary Examiner* — Kamal Saeed
(74) *Attorney, Agent, or Firm* — Paul M. Misiak

(57) ABSTRACT

The invention recites spirocyclic isoxazoline derivatives of Formula (V.1), Formula (V.2), Formula (V.1.1), and Formula (1)

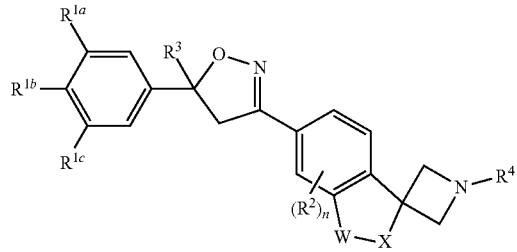
stereoisomers thereof, veterinarily acceptable salts thereof, compositions thereof, processes for making, and their use as a parasiticide in an animal. The variables A, V, Z, $W^1$, $W^2$, $W^3$, W, Y, X, $R^{1a}$, $R^{1b}$, $R^{1c}$, $R^2$, $R^3$, $R^4$, n, and "═" are as described herein.
36 Claims, No Drawings

SPIROCYCLIC ISOXAZOLINE DERIVATIVES AS ANTIPARASITIC AGENTS

CROSS REFERENCE

This invention claims priority to U.S. Provisional Patent Application No. 61/490,804 filed May 27, 2011, U.S. Provisional Patent Application No. 61/489,913 filed May 25, 2011, and U.S. Provisional Patent Application No. 61/451,256 filed Mar. 10, 2011.

FIELD OF THE INVENTION

This invention relates to spirocyclic isoxazoline derivatives having parasiticidal activity. The compounds of interest are spirocyclic isoxazoline derivatives with an azetidine moiety. The invention also relates to processes of making said spirocyclic isoxazoline derivatives, compositions and methods of use thereof.

BACKGROUND

There is a need for improved antiparasitic agents for use with animals, and in particular there is a need for improved insecticides and acaricides. Furthermore there is a need for improved topical and oral products with convenient administration and which contain one or more of such antiparasitic agents which can be used to effectively treat ectoparasites, such as insects (e.g., fleas, lice, and flies) and acarids (e.g., mites and ticks). Such products would be particularly useful for the treatment of animals including: birds (e.g., chickens and turkeys), fish, companion animals (e.g., cats dogs, llamas, and horses), and livestock (e.g., cattle, bison, swine, sheep, deer, elk, and goats).

The compounds currently available for insecticidal and acaricidal treatment of animals do not always demonstrate good activity, good speed of action, or a long duration of action. Most treatments contain hazardous chemicals that can have serious consequences, including neurotoxicity and lethality from accidental ingestion. Persons applying these agents are generally advised to limit their exposure. Pet collars and tags have been utilized to overcome some problems, but these are susceptible to chewing, ingestion, and subsequent toxicological affects to the animal. Thus, current treatments achieve varying degrees of success which depend partly on toxicity, method of administration, and efficacy. Currently, some agents are actually becoming ineffective due to parasitic resistance.

Isoxazoline derivatives have been disclosed in the art as having insecticidal and acaricidal activity. For example, WO2007/105814, WO2008/122375, and WO2009/035004 recite certain alkylene linked amides. WO2010/032437 discloses that the benzyl amide can be moved to the position ortho to the isoxazoline. Further, WO2007/075459 discloses phenyl isoxazolines substituted with 5- to 6-membered heterocycles, and WO2010/084067 and WO2010/025998 disclose phenyl isoxazolines substituted with 10- to 11-membered fused aryl and heteroaryls. Chiral processes for manufacturing isoxazolines have been reported in WO2011/104089 and WO2009/063910. Some spiro-azetidine isobenzofuran derivatives for the treatment of diabetes and hyperlipidemia were described in WO2008/096746. However, none of these citations exemplify spirocyclic substituted isoxazolines, or processes of manufacturing the spirocyclic compounds, nor does the prior art indicate that such compounds would be useful against a spectrum of parasitic species relevant to companion animals, livestock or fowl against the range of parasitic morphological lifecycle stages.

Despite the availability of effective, broad spectrum antiparasitic agents, there remains a need for a safer, convenient, efficacious, and environmentally friendly product that will overcome the ever-present threat of resistance development.

The present invention overcomes one or more of the various disadvantages of, or improves upon, the properties of existing compounds. In particular the present invention develops new spirocyclic isoxazoline substituted azetidine compounds which demonstrate such properties.

SUMMARY

The present invention provides Formula (V.1), Formula (V.2), Formula (V.1.1), and Formula (1) compounds, stereoisomers thereof, which act as parasiticides, in particular, ectoparasiticides; therefore may be used to prevent, treat, repel, and control acarids and insect infection and infestation in animals. In addition, the invention contemplates the control and prevention of tick borne diseases, for example, Lyme disease, canine and bovine anaplasmosis, canine ehrlichiosis, canine rickettsiosis, canine and bovine babesiosis, epizootic bovine abortion, and theileriosis. Thus, according to the invention, there is provided a compound of Formula (V.1) and Formula (V.2)

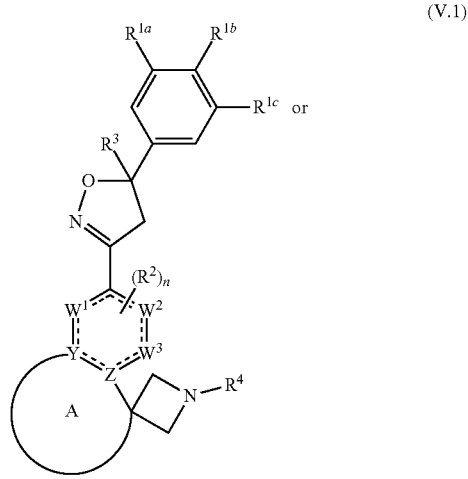

(V.1)

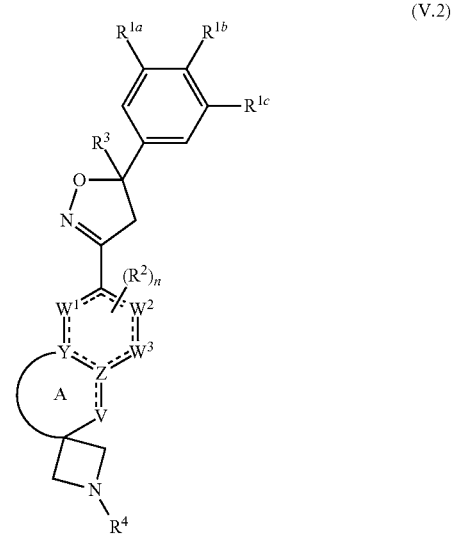

(V.2)

wherein
Y and Z are each independently C or N;
$W^1$, $W^2$, and $W^3$ are each independently C or N;
V is C, N, O, or S;
A taken together with Y and Z or V, Y, and Z is a 5- to 7-membered partially saturated or saturated carbocyclic or heterocyclic ring where the heterocyclic ring contains at least 1 to 3 heteroatoms selected from N, O, or S, and where ring A is optionally substituted with at least one substituent selected from oxo, =S, =$NR^7$, halo, hydroxyl, cyano, $C_1$-$C_6$alkyl, $C_1$-$C_6$haloalkyl, and $C_1$-$C_6$alkoxy;
$R^{1a}$, $R^{1b}$, and $R^{1c}$ are each independently hydrogen, halo, cyano, hydroxyl, nitro, $C_1$-$C_6$alkyl, $C_1$-$C_6$haloalkyl, $C_1$-$C_6$alkoxy, $C_0$-$C_3$alkyl$C_3$-$C_6$cycloalkyl, $C_1$-$C_6$haloalkoxy, —C(O)$NH_2$, —$SF_5$, or —S(O)$_p$R;
$R^2$ is halo, cyano, $C_1$-$C_6$alkyl, $C_1$-$C_6$haloalkyl, nitro, hydroxyl, —C(O)$NR^aR^b$, $C_2$-$C_6$alkenyl, $C_2$-$C_6$alkynyl, —S(O)$_p$R, or —OR;
$R^3$ is cyano, $C_1$-$C_6$alkyl, $C_1$-$C_6$haloalkyl, —C(O)$NR^aR^b$, $C_2$-$C_6$alkenyl, $C_2$-$C_6$alkynyl, $C_2$-$C_6$haloalkenyl, or $C_2$-$C_6$haloalkynyl;
$R^4$ is hydrogen, $C_1$-$C_6$alkyl, $C_0$-$C_6$alkyl$C_3$-$C_6$cycloalkyl, —C(O)$R^5$, —C(S)$R^5$, —C(O)$NR^aR^5$, —C(O)C(O)$NR^aR^5$, —S(O)$_p$$R^c$, —S(O)$_2$$NR^aR^5$, —C($NR^7$)$R^5$, —C($NR^7$)$NR^aR^5$, $C_0$-$C_6$alkylphenyl, $C_0$-$C_6$alkylheteroaryl, or $C_0$-$C_6$alkylheterocycle;
$R^5$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;
$R^6$ is hydrogen, $C_1$-$C_6$alkyl, hydroxyl, or $C_1$-$C_6$alkoxy;
$R^7$ is hydrogen, $C_1$-$C_6$alkyl, hydroxyl, cyano, nitro, —S(O)$_p$$R^c$, or $C_1$-$C_6$alkoxy;
R is $C_1$-$C_6$alkyl or $C_3$-$C_6$cycloalkyl optionally substituted with at least one halo substituent;
$R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;
$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;
$R^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$$NR^aR^b$, —$NR^aR^b$, —$NR^a$C(O)$R^b$, —SC(O)R, —SCN, or —C(O)$NR^aR^b$;
each of $R^4$ and $R^5$ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, —S(O)$_p$$R^c$, —SH, —S(O)$_p$$NR^aR^b$, —$NR^aR^b$, —$NR^a$C(O)$R^b$, —SC(O)R, —SCN, or —C(O)$NR^aR^b$; and
wherein each of $R^4$ and $R^5$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =$NR^7$, hydroxyl, $C_1$-$C_6$alkoxy, $C_1$-$C_6$alkyl, hydroxyl$C_1$-$C_6$alkyl-, $C_1$-$C_6$haloalkyl, —SH, —S(O)$_p$R, and $C_1$-$C_6$haloalkoxy;
n is the integer 0, 1, or 2, and when n is 2, each $R^2$ may be identical or different from each other;
p is the integer 0, 1, or 2; and
---- is a single or double bond;

stereoisomers thereof, and veterinarily acceptable salts thereof.

In another aspect of the invention are compounds of Formula (V.1) that are compounds of Formula (V.1.1)

(V.1.1)

wherein
$W^1$, $W^2$, and $W^3$ are each independently C or N;
X and W are each independently —O—, —S—, —$NR^6$—, —$CH_2$—, —C(O)—, —C($NR^7$)—, or —C(S)—, when X is —O—, —S—, or —$NR^6$—, then W is —$CH_2$—, —C(O)—, —C($NR^7$)—, or —C(S)—, and when W is —O—, —S—, or —$NR^6$—, then X is —$CH_2$—, —C(O)—, —C($NR^7$)—, or —C(S)—;
$R^{1a}$, $R^{1b}$, and $R^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$cycloalkyl, $C_1$-$C_6$haloalkoxy, —C(O)$NH_2$, —$SF_5$, or —S(O)$_p$R;
$R^2$ is fluoro, chloro, or $C_1$-$C_6$alkyl;
$R^3$ is cyano, $C_1$-$C_6$alkyl, $C_1$-$C_6$haloalkyl, —C(O)$NR^aR^b$, $C_2$-$C_6$alkenyl, $C_2$-$C_6$alkynyl, $C_2$-$C_6$haloalkenyl, or $C_2$-$C_6$haloalkynyl
$R^4$ is hydrogen, $C_1$-$C_6$alkyl, $C_0$-$C_6$alkyl$C_3$-$C_6$cycloalkyl, —C(O)$R^5$, —C(S)$R^5$, —C(O)$NR^aR^5$, —C(O)C(O)$NR^aR^5$, —S(O)$_p$$R^c$, —S(O)$_2$$NR^aR^5$, —C($NR^7$)$R^5$, —C($NR^7$)$NR^aR^5$, $C_0$-$C_6$alkylphenyl, $C_0$-$C_6$alkylheteroaryl, or $C_0$-$C_6$alkylheterocycle;
$R^5$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;
$R^6$ is hydrogen, $C_1$-$C_6$alkyl, hydroxyl, or $C_1$-$C_6$alkoxy;
$R^7$ is hydrogen, $C_1$-$C_6$alkyl, hydroxyl, cyano, nitro, —S(O)$_p$$R^c$, or $C_1$-$C_6$alkoxy;
R is $C_1$-$C_6$alkyl or $C_3$-$C_6$cycloalkyl optionally substituted with at least one halo substituent;
$R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;
$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;
$R^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$$NR^aR^b$, —$NR^aR^b$, —$NR^a$C(O)$R^b$, —SC(O)R, —SCN, or —C(O)$NR^aR^b$;
each of $R^4$ and $R^5$ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, —S(O)$_p$R$^c$, —SH, —S(O)$_p$NR$^a$R$^b$, —NR$^a$R$^b$, —NR$^a$C(O)R$^b$, —SC(O)R, —SCN, or —C(O)NR$^a$R$^b$; and wherein each of R$^4$ and R$^5$ is $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =NR$^7$, hydroxyl$C_1$-$C_6$alkyl-, hydroxyl, $C_1$-$C_6$alkoxy, $C_1$-$C_6$alkyl, $C_1$-$C_6$haloalkyl, —SH, —S(O)$_p$R, and $C_1$-$C_6$haloalkoxy;

n is the integer 0, 1, or 2, and when n is 2, each R$^2$ may be identical or different from each other; and p is the integer 0, 1, or 2, stereoisomers thereof, and veterinarily acceptable salts thereof.

In another aspect of the invention are compounds of Formula (V.1.1) wherein W$^1$ is N and W$^2$ and W$^3$ are each C, or W$^2$ is N and W$^1$ and W$^3$ are each C, or W$^3$ is N and W$^1$ and W$^2$ are each C. In yet another aspect, W$^1$ is N and W$^2$ and W$^3$ are each C. In yet another aspect, W$^2$ is N and W$^1$ and W$^3$ are each C. In yet another aspect, W$^3$ is N and W$^1$ and W$^2$ are each C. In each case, X is O and W is —C(O)— or —CH$_2$—, or W is O and X is —C(O)— or —CH$_2$—, or X is —NR$^6$— and W is —CH$_2$— or —C(O)—, or W is —NR$^6$— and X is —CH$_2$— or —C(O)—. In one embodiment, X is O and W is —C(O)—. In another embodiment, X is O and W is —CH$_2$—. In another embodiment, X is —NR$^6$— and W is —CH$_2$—. In yet another embodiment, X is —NR$^6$— and W is —C(O)—. In another embodiment, W is O and X is —C(O)—. In another embodiment, W is O and X is —CH$_2$—. In another embodiment, W is —NR$^6$— and X is —CH$_2$—. In yet another embodiment, W is —NR$^6$— and X is —C(O)—, stereoisomers thereof, and veterinarily acceptable salts thereof.

In another aspect of the invention are compounds of Formula (1)

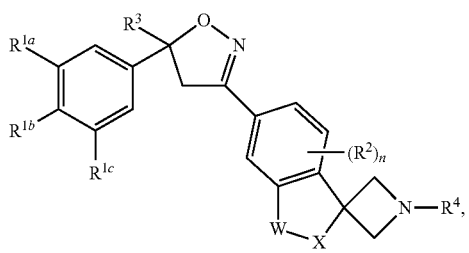

(1)

wherein

X and W are each independently —O—, —S—, —NR$^6$—, —CH$_2$—, —C(O)—, —C(NR$^7$)—, or —C(S)—, when X is —O—, —S—, or —NR$^6$—, then W is —CH$_2$—, —C(O)—, —C(NR$^7$)—, or —C(S)—, and when W is —O—, —S—, or —NR$^6$—, then X is —CH$_2$—, —C(O)—, —C(NR$^7$)—, or —C(S)—;

R$^{1a}$, R$^{1b}$, and R$^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$cycloalkyl, $C_1$-$C_6$haloalkoxy, —C(O)NH$_2$, —SF$_5$, or —S(O)$_p$R;

R$^2$ is fluoro, chloro, or $C_1$-$C_6$alkyl;

R$^3$ is cyano, $C_1$-$C_6$alkyl, $C_1$-$C_6$haloalkyl, —C(O)NR$^a$R$^b$, $C_2$-$C_6$alkenyl, $C_2$-$C_6$alkynyl, $C_2$-$C_6$haloalkenyl, or $C_2$-$C_6$haloalkynyl R$^4$ is hydrogen, $C_1$-$C_6$alkyl, $C_0$-$C_6$alkyl$C_3$-$C_6$cycloalkyl, —C(O)R$^5$, —C(S)R$^5$, —C(O)NR$^a$R$^5$, —C(O)C(O)NR$^a$R$^5$, —S(O)$_p$R$^c$, —S(O)$_2$NR$^a$R$^5$, —C(NR$^7$)R$^5$, —C(NR$^7$)NR$^a$R$^5$, $C_0$-$C_6$alkylphenyl, $C_0$-$C_6$alkylheteroaryl, or $C_0$-$C_6$alkylheterocycle;

R$^5$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;

R$^6$ is hydrogen, $C_1$-$C_6$alkyl, hydroxyl, or $C_1$-$C_6$alkoxy;

R$^7$ is hydrogen, $C_1$-$C_6$alkyl, hydroxyl, cyano, nitro, —S(O)$_p$R$^c$, or $C_1$-$C_6$alkoxy;

R is $C_1$-$C_6$alkyl or $C_3$-$C_6$cycloalkyl optionally substituted with at least one halo substituent;

R$^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

R$^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

R$^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R, —SCN, or —C(O)NR$^a$R$^b$;

each of R$^4$ and R$^5$ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, —S(O)$_p$R$^b$, —SH, —S(O)$_p$NR$^a$R$^b$, —NR$^a$R$^b$, —NR$^a$C(O)R$^b$, —SC(O)R, —SCN, or —C(O)NR$^a$R$^b$; and wherein each of R$^4$ and R$^5$ is $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =NR$^7$, hydroxyl$C_1$-$C_6$alkyl-, hydroxyl, $C_1$-$C_6$alkoxy, $C_1$-$C_6$alkyl, $C_1$-$C_6$haloalkyl, —SH, —S(O)$_p$R, and $C_1$-$C_6$haloalkoxy;

n is the integer 0, 1, or 2, and when n is 2, each R$^2$ may be identical or different from each other; and p is the integer 0, 1, or 2;

stereoisomers thereof, and veterinarily acceptable salts thereof.

In another aspect of the invention of Formula (1), X is —O— and W is —C(O)—.

The compound of Formula (1) when X is —O— and W is —C(O)— is also represented as Formula (1.1)

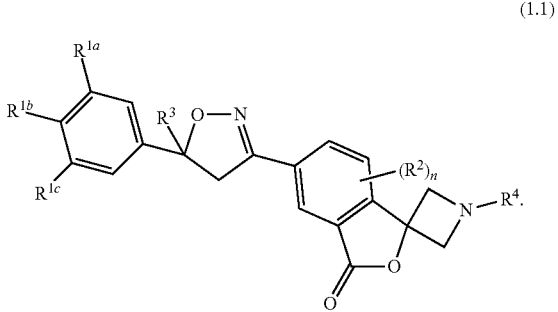

(1.1)

In another aspect of the invention of Formula (1), X is —O— and W is —C(NR⁷)—.

In another aspect of the invention of Formula (1), X is —O— and W is —C(S)—.

In another aspect of the invention of Formula (1), X is —O— and W is —CH₂—.

The compound of Formula (1) when X is —O— and W is —CH₂— is also represented as Formula (1.2)

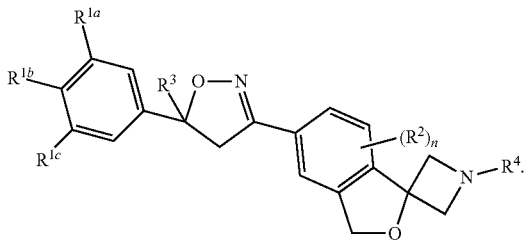

(1.2)

In another aspect of the invention of Formula (1), X is —NR⁶— and W is —C(NR⁷)—.

The compound of Formula (1) when X is —NR⁶— and W is —C(O)— is also represented as Formula (1.3)

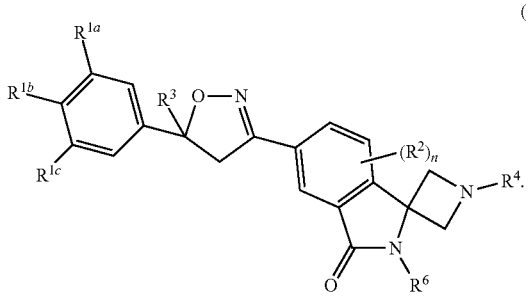

(1.3)

In another aspect of the invention, when W is —C(O)— and X is NR⁶, then R⁶ is hydrogen or C₁-C₆alkyl. In yet another aspect of the invention, when W is —C(O)— and X is NR⁶, then R⁶ is hydrogen, methyl, ethyl, isopropyl, propyl, or t-butyl. In yet another aspect of the invention, when W is —C(O)— and X is NR⁶, then R⁶ is hydrogen, methyl, ethyl, or isopropyl. In yet another aspect of the invention, when W is —C(O)— and X is NR⁶, then R⁶ is hydrogen, methyl, or ethyl. In yet another aspect of the invention, when W is —C(O)— and X is NR⁶, then R⁶ is hydrogen or methyl. In yet another aspect of the invention, when W is —C(O)— and X is NR⁶, then R⁶ is hydrogen. In yet another aspect of the invention, when W is —C(O)— and X is NR⁶, then R⁶ is methyl.

In another aspect of the invention of Formula (1), X is —NR⁶— and W is —C(S)—.

In another aspect of the invention of Formula (1), X is —NR⁶— and W is —CH₂—.

In another aspect of the invention of Formula (1), X is —NR⁶— and W is —C(O)—.

In another aspect of the invention of Formula (1), X is —S— and W is —C(S)—.

In another aspect of the invention of Formula (1), X is —S— and W is —C(O)—.

In another aspect of the invention of Formula (1), X is —S— and W is —C(NR⁷)—.

In another aspect of the invention of Formula (1), X is —S— and W is —CH₂—.

In another aspect of the invention of Formula (1), W is —O— and X is —C(O)—.

The compound of Formula (1) when W is —O— and X is —C(O)— is also represented as Formula (1.4)

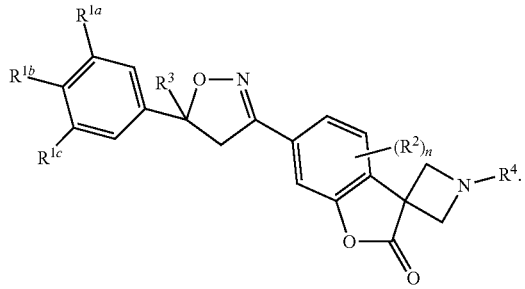

(1.4)

In another aspect of the invention of Formula (1), W is —O— and X is —C(NR⁷)—.

In another aspect of the invention of Formula (1), W is —O— and X is —C(S)—.

In another aspect of the invention of Formula (1), W is —O— and X is —CH₂—.

The compound of Formula (1) when W is —O— and X is —CH₂— is also represented as Formula (1.5)

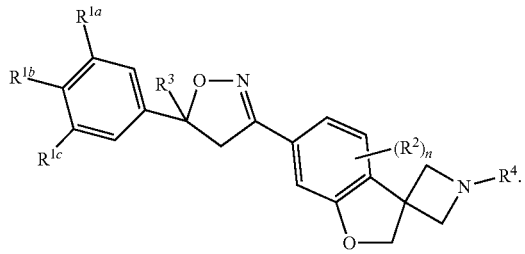

(1.5)

In another aspect of the invention of Formula (1), W is —NR⁶— and X is —C(S)—.

In another aspect of the invention of Formula (1), W is —NR⁶— and X is —C(O)—.

The compound of Formula (1) when W is —NR⁶— and X is —C(O)— is also represented as Formula (1.6)

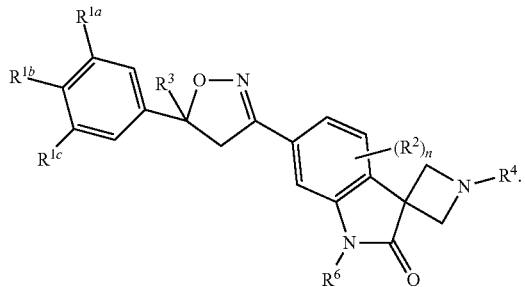

(1.6)

In another aspect of the invention of Formula (1), W is —$NR^6$— and X is —$CH_2$—.

In another aspect of the invention of Formula (1), W is —$NR^6$— and X is —C(S)—.

In another aspect of the invention of Formula (1), W is —$NR^6$— and X is —$CH_2$—.

In another aspect of the invention of Formula (1), W is —S— and X is —C(S)—.

In another aspect of the invention of Formula (1), W is —S— and X is —C(O)—.

In another aspect of the invention of Formula (1), W is —S— and X is —C($NR^7$)—.

In another aspect of the invention of Formula (1), W is —S— and X is —$CH_2$—.

In yet another aspect of the invention, each of $R^{1a}$, $R^{1b}$, and $R^{1c}$ are independently selected from hydrogen, halo, cyano, $C_1$-$C_6$ haloalkyl, and $C_0$-$C_3$alkyl$C_3$-$C_6$cycloalkyl. In yet another aspect of the invention, each of $R^{1a}$, $R^{1b}$, and $R^{1c}$ are independently selected from hydrogen, halo, cyano, and $C_1$-$C_6$, haloalkyl. In yet another aspect of the invention, each of $R^{1a}$, $R^{1b}$, and $R^{1c}$ are independently selected from hydrogen, fluoro, chloro, bromo, cyano, and $C_1$-$C_6$, haloalkyl. In yet another aspect of the invention, each of $R^{1a}$, $R^{1b}$, and $R^{1c}$ are independently selected from hydrogen, fluoro, chloro, bromo, and $C_1$-$C_6$ haloalkyl.

In yet another aspect of the invention, each of $R^{1a}$, $R^{1b}$, and $R^{1c}$ are independently selected from hydrogen, fluoro, chloro, bromo, and —$CF_3$. In another aspect of the invention, $R^{1a}$ and $R^{1c}$ are both chloro and $R^{1b}$ is fluoro. In another aspect of the invention, the integer n of $(R^2)_n$ is 0. In another aspect of the invention, the integer n of $(R^2)_n$ is 1. When the integer n is 1, then $R^2$ is fluoro, chloro, methyl, or ethyl. In another aspect of the invention, when the integer n is 1, then $R^2$ is fluoro. In yet another aspect of the invention, when the integer n is 1, then $R^2$ is chloro. In yet another aspect of the invention, when the integer n is 1, then $R^2$ is methyl. In yet another aspect of the invention, when the integer n is 1, then $R^2$ is ethyl. In yet another aspect of the invention, the integer n of $(R^2)_n$ is 2. When the integer n is 2, then each $R^2$ is independently fluoro or chloro.

In yet another aspect of the invention, $R^3$ is cyano, $C_1$-$C_6$alkyl, $C_1$-$C_6$haloalkyl, or —C(O)$NH_2$. In another aspect of the invention, $R^3$ is cyano, $C_1$-$C_6$alkyl, or $C_1$-$C_6$haloalkyl. In yet another aspect of the invention, $R^3$ is cyano, methyl, ethyl, or $C_1$-$C_6$haloalkyl. In yet another aspect of the invention, $R^3$ is cyano, methyl, or $C_1$-$C_6$haloalkyl. In yet another aspect of the invention, $R^3$ is cyano or $C_1$-$C_6$haloalkyl. In yet another aspect of the invention, $R^3$ is $C_1$-$C_6$haloalkyl. In yet another aspect of the invention, $R^3$ is —$CF_3$, —$CHF_2$, —$CH_2F$, and —$CF_2Cl$. In yet another aspect of the invention, $R^3$ is —$CF_3$, —$CHF_2$, and —$CH_2F$. In yet another aspect of the invention, $R^3$ is —$CF_3$.

In yet another aspect of the invention, $R^4$ is hydrogen, $C_1$-$C_6$alkyl, $C_0$-$C_6$alkyl$C_3$-$C_6$cycloalkyl, —C(O)$R^5$, —C(S)$R^5$, —C(O)$NR^aR^5$, —S(O)$_pR^c$, —S(O)$_2NR^aR^5$, —C($NR^7$)$R^5$, $C_0$-$C_6$alkylphenyl, $C_0$-$C_6$alkylheteroaryl, or $C_0$-$C_6$alkylheterocycle. In yet another aspect of the invention, $R^4$ is hydrogen, $C_1$-$C_6$alkyl, $C_0$-$C_6$alkyl$C_3$-$C_6$cycloalkyl, —C(O)$R^5$, —C(S)$R^5$, —C(O)$NR^aR^5$, —S(O)$_pR^c$, —S(O)$_2NR^aR^5$, or —C($NR^7$)$R^5$. In yet another aspect of the invention, $R^4$ is hydrogen, $C_1$-$C_6$alkyl, $C_0$-$C_6$alkyl$C_3$-$C_6$cycloalkyl, or —C(O)$R^5$. In yet another aspect of the invention, $R^4$ is hydrogen, $C_1$-$C_6$alkyl, or —C(O)$R^5$. In yet another aspect of the invention, $R^4$ is hydrogen or —C(O)$R^5$. In yet another aspect of the invention, $R^4$ is hydrogen. In yet another aspect of the invention, $R^4$ is —C(O)$R^5$. $R^4$ can be optionally substituted as defined herein.

In yet another aspect of the invention, $R^5$ is $C_1$-$C_6$alkyl, $C_0$-$C_6$alkyl$C_3$-$C_6$cycloalkyl, $C_0$-$C_6$alkylheteroaryl, or $C_0$-$C_6$alkylheterocycle. In yet another aspect of the invention, $R^5$ is $C_1$-$C_6$alkyl. In yet another aspect of the invention, $R^5$ is methyl, ethyl, propyl, isopropyl, t-butyl, and isobutyl. Each of the $R^5$ $C_1$-$C_6$alkyls can be optionally substituted as defined herein, for example, with at least one substituent selected from hydroxyl, halo, trifluoromethyl, thiomethyl, thiotrifluoromethyl, —$SO_2CH_3$, —$SO_2CF_3$, and —NHCHO. In yet another aspect of the invention, $R^5$ is $C_0$-$C_6$alkyl$C_3$-$C_6$cycloalkyl. In yet another aspect of the invention, $R^5$ is cyclopropyl, cyclobutyl, cyclopropylmethyl, cyclopropylethyl, cyclobutylmethyl, and cyclopentyl. Each of the $R^5$ $C_0$-$C_6$alkyl$C_3$-$C_6$cycloalkyls can be optionally substituted as defined herein, for example, with at least one substituent selected from hydroxyl, —$CH_2OH$, halo, methyl, ethyl, and trifluoromethyl. In yet another aspect of the invention, $R^5$ is $C_0$-$C_6$alkylheteroaryl. In yet another aspect of the invention, $R^5$ is —$CH_2$pyrazole, and —$CH_2$pyridazine. Each of the $R^5$ $C_0$-$C_6$alkylheteroaryl moieties can be optionally substituted as defined herein, for example, with at least one substituent selected from hydroxyl, methyl, halo, and trifluoromethyl. In yet another aspect of the invention, $R^5$ is $C_0$-$C_6$alkylheterocycle. In yet another aspect of the invention $R^5$ is oxetane, thiatane, azetidine, tetrahydrofuran, tetrahydrothiophene, and pyrrolidine. Each of the $R^5$ $C_0$-$C_6$alkylheterocycle moieties can be optionally substituted as defined herein, for example, with at least one substituent selected from halo, —$CH_2OH$, methyl, oxo, and trifluoromethyl.

In yet another aspect of the invention, when X is —O— and W is —C(O)—, or when X is —O— and W is —$CH_2$—, then $R^{1a}$, $R^{1b}$, and $R^{1c}$ are each independently hydrogen, halo, or $C_1$-$C_6$haloalkyl, $R^3$ is —$CF_3$, and $R^4$ is —C(O)$R^5$; stereoisomers thereof, and veterinarily acceptable salts thereof. In yet another aspect of the invention, when X is —O— and W is —C(O)—, or when X is —O— and W is —$CH_2$—, then $R^{1a}$, $R^{1b}$, and $R^{1c}$ are each independently hydrogen, halo, or $C_1$-$C_6$haloalkyl, $R^3$ is —$CF_3$, $R^4$ is —C(O)$R^5$, and $R^5$ is $C_1$-$C_6$alkyl, $C_0$-$C_6$alkyl$C_3$-$C_6$cycloalkyl, $C_0$-$C_6$alkylheteroaryl, or $C_0$-$C_6$alkylheterocycle, wherein each of $R^5$ $C_1$-$C_6$alkyl or $C_0$-$C_6$alkyl$C_3$-$C_6$cycloalkyl moiety can be optionally and independently substituted by at least one substituent selected from cyano, halo, hydroxyl, —$CH_2OH$, oxo, $C_1$-$C_6$alkoxy, $C_1$-$C_6$haloalkoxy, $C_1$-$C_6$haloalkyl, —S(O)$_pR^c$, —SH, —S(O)$_pNR^aR^b$, —$NR^aR^b$, —$NR^aC(O)R^b$, —SC(O)R, —SCN, or —C(O)$NR^aR^b$, and wherein each of $R^5$ $C_0$-$C_6$alkylheteroaryl or $C_0$-$C_6$alkylheterocycle moiety can be further optionally substituted with at least one substituent selected from cyano, —$CH_2OH$, halo, oxo, =S, =$NR^7$, hydroxyl, $C_1$-$C_6$alkoxy, $C_1$-$C_6$alkyl, $C_1$-$C_6$haloalkyl, —SH, —S(O)$_pR$, and $C_1$-$C_6$haloalkoxy, stereoisomers thereof, and veterinarily acceptable salts thereof. More specifically, the $R^5$ $C_1$-$C_6$alkyl or $C_0$-$C_6$alkyl$C_3$-$C_6$cycloalkyl moiety can be optionally and independently substituted by at least one substituent selected from halo, hydroxyl, $C_1$-$C_6$haloalkyl, —S(O)$_pR^c$, and —$NR^aC(O)R^b$. More specifically, the $R^5$ $C_0$-$C_6$alkylheteroaryl or $C_0$-$C_6$alkylheterocycle moiety can be further optionally substituted with at least one substituent selected from halo, oxo, and $C_1$-$C_6$alkyl.

In another aspect of the invention, are Formula (1) compounds selected from:

1-(cyclopropanecarbonyl)-5'-(3,4,5-trichlorophenyl)-5-(trifluoromethyl)-4,5-dihydroisoxazol-3-yl)-3'H-spiro{azetidine-3,1'-isobenzofuran}-3'-one;

5'-(5-(3,5-dichloro-4-fluorophenyl)-5-(trifluoromethyl)-4,5-dihydroisoxazol-3-yl)-1-propionyl-3'H-spiro[azetidine-3,1-isobenzofuran]-3'-one;

1-(cyclopropanecarbonyl)-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(3-methylbutanoyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2-hydroxy-2-methylpropanoyl)-3'H-spiro[azetidine-3,1'-isobenzofuran]-3'-one;

1-(2-cyclopropylacetyl)-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

1-acetyl-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(1-hydroxycyclopropanecarbonyl)-3'H-spiro[azetidine-3,1'-isobenzofuran]-3'-one;

1-(cyclobutanecarbonyl)-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-pivaloyl-3'H-spiro[azetidine-3,1-isobenzofuran]-3'-one;

5'-(5-(3,5-dichloro-4-fluorophenyl)-5-(trifluoromethyl)-4,5-dihydroisoxazol-3-yl)-1-(2-hydroxyacetyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2-(1-hydroxycyclopropyl)acetyl)-3'H-spiro[azetidine-3,1'-isobenzofuran]-3'-one;

1-butyryl-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2-(methylthio)acetyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2-(methylsulfinyl)acetyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2-(methylsulfonyl)acetyl)-3'H-spiro[azetidine-3,1'-isobenzofuran]-3'-one;

1-(2-(1H-pyrazol-1-yl)acetyl)-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(1-(trifluoromethyl)cyclopropanecarbonyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-isobutyryl-3'H-spiro[azetidine-3,1-isobenzofuran]-3'-one;

5'-(5-(3,5-dichloro-4-fluorophenyl)-5-(trifluoromethyl)-4,5-dihydroisoxazol-3-yl)-1-(2-(3-methyl-1H-pyrazol-1-yl)acetyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(3-hydroxy-2-methylpropanoyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2,2-difluorocyclopropanecarbonyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(4,4,4-trifluorobutanoyl)-3'H-spiro[azetidine-3,1'-isobenzofuran]-3'-one;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-((trifluoromethypthio)ethanone;

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1-oxidothietan-3-yl)methanone;

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;

(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;

(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;

(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;

(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-methylpropan-1-one;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-hydroxyethanone;

cyclobutyl(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)methanone;

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1-hydroxycyclopropyl)methanone;

N-(2-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-oxoethyl)formamide;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)propan-1-one;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-hydroxy-2-methylpropan-1-one;

2-cyclopropyl-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2,2-dimethylpropan-1-one;

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1-(trifluoromethyl)cyclopropyl)-methanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-3-hydroxy-2-methylpropan-1-one;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(3-methyl-1H-pyrazol-1-yl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-3-methylbutan-1-one;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(1H-pyrazol-1-yl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-3-hydroxybutan-1-one;

cyclopropyl(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)methanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)butan-1-one;

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(thietan-3-yl)methanone;

(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;

(R)-(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;

(S)-(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;

2-(methylsulfonyl)-1-(5'-(5-(3,4,5-trichlorophenyl)-5-(trifluoromethyl)-4,5-dihydroisoxazol-3-yl)-3'H-spiro[azetidine-3,1'-isobenzofuran]-1-yl)ethanone;

1-(5'-(5-(3,5-dichlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3-chloro-5-(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3,4-dichloro-5-(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)-ethanone;

1-(5'-(5-(4-bromo-3,5-dichlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(R)-1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(S)-1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3-bromo-5-chlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(4-chloro-3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3-chloro-5-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(R)-1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(S)-1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone;

(R)-2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone;

(S)-2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone;

5'-(5-(3,5-bis(trifluoromethyl)phenyl)-5-(trifluoromethyl)-4,5-dihydroisoxazol-3-yl)-1-(2-(methylsulfonyl)acetyl)spiro[azetidine-3,1'-isoindolin]-3'-one;

5'-(5-(3,5-dichloro-4-fluorophenyl)-5-(trifluoromethyl)-4,5-dihydroisoxazol-3-yl)-1-(2-(methylsulfonyl)acetyl)spiro[azetidine-3,1'-isoindolin]-3'-one;

1-(cyclopropanecarbonyl)-5'-(5-(3,5-dichloro-4-fluorophenyl)-5-(trifluoromethyl)-4,5-dihydroisoxazol-3-yl)spiro[azetidine-3,1'-isoindolin]-3'-one;

5'-(5-(3,4-dichloro-5-(trifluoromethyl)phenyl)-5-(trifluoromethyl)-4,5-dihydroisoxazol-3-yl)-1-(2-(methylsulfonyl)acetyl)spiro[azetidine-3,1'-isoindolin]-3'-one;

1-(2-(methylsulfonyl)acetyl)-5'-(5-(3,4,5-trichlorophenyl)-5-(trifluoromethyl)-4,5-dihydroisoxazol-3-yl)spiro[azetidine-3,1'-isoindolin]-3'-one;

5'-(5-(3-chloro-5-(trifluoromethyl)phenyl)-5-(trifluoromethyl)-4,5-dihydroisoxazol-3-yl)-1-(2-(methylsulfonyl)acetyl)spiro[azetidine-3,1'-isoindolin]-3'-one;

5'-(5-(4-bromo-3,5-dichlorophenyl)-5-(trifluoromethyl)-4,5-dihydroisoxazol-3-yl)-1-(2-(methylsulfonyl)acetyl)spiro[azetidine-3,1'-isoindolin]-3'-one;

5'-(5-(3,5-dichlorophenyl)-5-(trifluoromethyl)-4,5-dihydroisoxazol-3-yl)-1-(2-(methylsulfonyl)acetyl)spiro[azetidine-3,1'-isoindolin]-3'-one;

5'-(5-(3,5-dichloro-4-fluorophenyl)-5-(trifluoromethyl)-4,5-dihydroisoxazol-3-yl)-1-(thietane-3-carbonyl)spiro[azetidine-3,1'-isoindolin]-3'-one;

5'-(5-(3,5-dichloro-4-fluorophenyl)-5-(trifluoromethyl)-4,5-dihydroisoxazol-3-yl)-1-(1,1-dioxidothietane-3-carbonyl)spiro[azetidine-3,1'-isoindolin]-3'-one;

5'-(5-(3,5-bis(trifluoromethyl)phenyl)-5-(trifluoromethyl)-4,5-dihydroisoxazol-3-yl)-1-(cyclopropanecarbonyl)spiro[azetidine-3,1'-isoindolin]-3'-one;

5'-(5-(3-chloro-5-(trifluoromethyl)phenyl)-5-(trifluoromethyl)-4,5-dihydroisoxazol-3-yl)-1-(cyclopropanecarbonyl)spiro[azetidine-3,1'-isoindolin]-3'-one;

5'-(5-(4-bromo-3,5-dichlorophenyl)-5-(trifluoromethyl)-4,5-dihydroisoxazol-3-yl)-1-(cyclopropanecarbonyl)spiro[azetidine-3,1'-isoindolin]-3'-one;

2'-methyl-1-(2-(methylsulfonyl)acetyl)-5'-(5-(3,4,5-trichlorophenyl)-5-(trifluoromethyl)-4,5-dihydroisoxazol-3-yl)spiro[azetidine-3,1'-isoindolin]-3'-one;

5'-(5-(3,5-dichloro-4-fluorophenyl)-5-(trifluoromethyl)-4,5-dihydroisoxazol-3-yl)-2'-methyl-1-(2-(methylsulfonyl)acetyl)spiro[azetidine-3,1'-isoindolin]-3'-one; and 1-(cyclopropanecarbonyl)-2'-methyl-5'-(5-(3,4,5-trichlorophenyl)-5-(trifluoromethyl)-4,5-dihydroisoxazol-3-yl)spiro[azetidine-3,1'-isoindolin]-3'-one, or a stereoisomer thereof, or a veterinarily acceptable salt thereof.

In another aspect of the invention, are Formula (1) compounds selected from:

1-(cyclopropanecarbonyl)-5'-(3,4,5-trichlorophenyl)-5-(trifluoromethyl)-4,5-dihydroisoxazol-3-yl)-3'H-spiro{azetidine-3,1'-isobenzofuran}-3'-one;

5'-(5-(3,5-dichloro-4-fluorophenyl)-5-(trifluoromethyl)-4,5-dihydroisoxazol-3-yl)-1-propionyl-3'H-spiro[azetidine-3,1-isobenzofuran]-3'-one;

1-(cyclopropanecarbonyl)-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(3-methylbutanoyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2-hydroxy-2-methylpropanoyl)-3'H-spiro[azetidine-3,1'-isobenzofuran]-3'-one;

1-(2-cyclopropylacetyl)-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

1-acetyl-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(1-hydroxycyclopropanecarbonyl)-3'H-spiro[azetidine-3,1'-isobenzofuran]-3'-one;

1-(cyclobutanecarbonyl)-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-pivaloyl-3'H-spiro[azetidine-3,1-isobenzofuran]-3'-one;

5'-(5-(3,5-dichloro-4-fluorophenyl)-5-(trifluoromethyl)-4,5-dihydroisoxazol-3-yl)-1-(2-hydroxyacetyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2-(1-hydroxycyclopropyl)acetyl)-3'H-spiro[azetidine-3,1'-isobenzofuran]-3'-one;

1-butyryl-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2-(methylthio)acetyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2-(methylsulfinyl)acetyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2-(methylsulfonyl)acetyl)-3'H-spiro[azetidine-3,1'-isobenzofuran]-3'-one;

1-(2-(1H-pyrazol-1-yl)acetyl)-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(1-(trifluoromethyl)cyclopropanecarbonyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-isobutyryl-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2-(3-methyl-1H-pyrazol-1-yl)acetyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(3-hydroxy-2-methylpropanoyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2,2-difluorocyclopropanecarbonyl)-3'H-spiro[azetidine-3,1'-isobenzofuran]-3'-one; and 5'-(5-(3,5-dichloro-4-fluorophenyl)-5-(trifluoromethyl)-4,5-dihydroisoxazol-3-yl)-1-(4,4,4-trifluorobutanoyl)-3'H-spiro[azetidine-3,1'-isobenzofuran]-3'-one, or a stereoisomer thereof, or a veterinarily acceptable salt thereof.

In another aspect of the invention, are Formula (1) compounds selected from:

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-((trifluoromethypthio)ethanone;

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1-oxidothietan-3-yl)methanone;

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;

(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;

(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;

(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;

(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-methylpropan-1-one;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-hydroxyethanone;

cyclobutyl(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)methanone;

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1-hydroxycyclopropyl)methanone;

N-(2-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-oxoethyl)formamide;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)propan-1-one;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-hydroxy-2-methylpropan-1-one;

2-cyclopropyl-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2,2-dimethylpropan-1-one;

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1-(trifluoromethyl)cyclopropyl)-methanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-3-hydroxy-2-methylpropan-1-one;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(3-methyl-1H-pyrazol-1-yl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-3-methylbutan-1-one;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(1H-pyrazol-1-yl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-3-hydroxybutan-1-one;

cyclopropyl(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)methanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl) butan-1-one;

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(thietan-3-yl)methanone;

(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;

(R)-(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;

(S)-(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;

2-(methylsulfonyl)-1-(5'-(5-(3,4,5-trichlorophenyl)-5-(trifluoromethyl)-4,5-dihydroisoxazol-3-yl)-3'H-spiro[azetidine-3,1'-isobenzofuran]-1-yl)ethanone;

1-(5'-(5-(3,5-dichlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3-chloro-5-(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3,4-dichloro-5-(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)-ethanone;

1-(5'-(5-(4-bromo-3,5-dichlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(R)-1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(S)-1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3-bromo-5-chlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(4-chloro-3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3-chloro-5-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(R)-1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(S)-1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone;

(R)-2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone; and (S)-2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone, or a stereoisomer thereof, or a veterinarily acceptable salt thereof.

In another aspect of the invention, are Formula (1) compounds selected from:

5'-(5-(3,5-bis(trifluoromethyl)phenyl)-5-(trifluoromethyl)-4,5-dihydroisoxazol-3-yl)-1-(2-(methylsulfonyl)acetyl)spiro[azetidine-3,1'-isoindolin]-3'-one;

5'-(5-(3,5-dichloro-4-fluorophenyl)-5-(trifluoromethyl)-4,5-dihydroisoxazol-3-yl)-1-(2-(methylsulfonyl)acetyl)spiro[azetidine-3,1'-isoindolin]-3'-one;

1-(cyclopropanecarbonyl)-5'-(5-(3,5-dichloro-4-fluorophenyl)-5-(trifluoromethyl)-4,5-dihydroisoxazol-3-yl)spiro[azetidine-3,1'-isoindolin]-3'-one;

5'-(5-(3,4-dichloro-5-(trifluoromethyl)phenyl)-5-(trifluoromethyl)-4,5-dihydroisoxazol-3-yl)-1-(2-(methylsulfonyl)acetyl)spiro[azetidine-3,1'-isoindolin]-3'-one;

1-(2-(methylsulfonyl)acetyl)-5'-(5-(3,4,5-trichlorophenyl)-5-(trifluoromethyl)-4,5-dihydroisoxazol-3-yl)spiro[azetidine-3,1'-isoindolin]-3'-one;

5'-(5-(3-chloro-5-(trifluoromethyl)phenyl)-5-(trifluoromethyl)-4,5-dihydroisoxazol-3-yl)-1-(2-(methylsulfonyl)acetyl)spiro[azetidine-3,1'-isoindolin]-3'-one;

5'-(5-(4-bromo-3,5-dichlorophenyl)-5-(trifluoromethyl)-4,5-dihydroisoxazol-3-yl)-1-(2-(methylsulfonyl)acetyl)spiro[azetidine-3,1'-isoindolin]-3'-one;

5'-(5-(3,5-dichlorophenyl)-5-(trifluoromethyl)-4,5-dihydroisoxazol-3-yl)-1-(2-(methylsulfonyl)acetyl)spiro[azetidine-3,1'-isoindolin]-3'-one;

5'-(5-(3,5-dichloro-4-fluorophenyl)-5-(trifluoromethyl)-4,5-dihydroisoxazol-3-yl)-1-(thietane-3-carbonyl)spiro[azetidine-3,1'-isoindolin]-3'-one;

5'-(5-(3,5-dichloro-4-fluorophenyl)-5-(trifluoromethyl)-4,5-dihydroisoxazol-3-yl)-1-(1,1-dioxidothietane-3-carbonyl)spiro[azetidine-3,1'-isoindolin]-3'-one;

5'-(5-(3,5-bis(trifluoromethyl)phenyl)-5-(trifluoromethyl)-4,5-dihydroisoxazol-3-yl)-1-(cyclopropanecarbonyl)spiro[azetidine-3,1'-isoindolin]-3'-one;

5'-(5-(3-chloro-5-(trifluoromethyl)phenyl)-5-(trifluoromethyl)-4,5-dihydroisoxazol-3-yl)-1-(cyclopropanecarbonyl)spiro[azetidine-3,1'-isoindolin]-3'-one;

5'-(5-(4-bromo-3,5-dichlorophenyl)-5-(trifluoromethyl)-4,5-dihydroisoxazol-3-yl)-1-(cyclopropanecarbonyl)spiro[azetidine-3,1'-isoindolin]-3'-one;

2'-methyl-1-(2-(methylsulfonyl)acetyl)-5'-(5-(3,4,5-trichlorophenyl)-5-(trifluoromethyl)-4,5-dihydroisoxazol-3-yl)spiro[azetidine-3,1'-isoindolin]-3'-one;

5'-(5-(3,5-dichloro-4-fluorophenyl)-5-(trifluoromethyl)-4,5-dihydroisoxazol-3-yl)-2'-methyl-1-(2-(methylsulfonyl)acetyl)spiro[azetidine-3,1'-isoindolin]-3'-one; and 1-(cyclopropanecarbonyl)-2'-methyl-5'-(5-(3,4,5-trichlorophenyl)-5-(trifluoromethyl)-4,5-dihydroisoxazol-3-yl)spiro[azetidine-3,1'-isoindolin]-3'-one, or a stereoisomer thereof, or a veterinarily acceptable salt thereof.

In another aspect of the invention, is the Formula (1) compound:

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;

(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;

(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;

(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;

(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;

(R)-(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;

(S)-(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;

1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(R)-1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(S)-1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(R)-1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(S)-1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone;

(R)-2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone; and (S)-2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone, or a stereoisomer thereof, or a veterinarily acceptable salt thereof.

In another aspect of the invention, is a process for preparing the chiral spiroisoxazolines of Formula (63) of Scheme 16

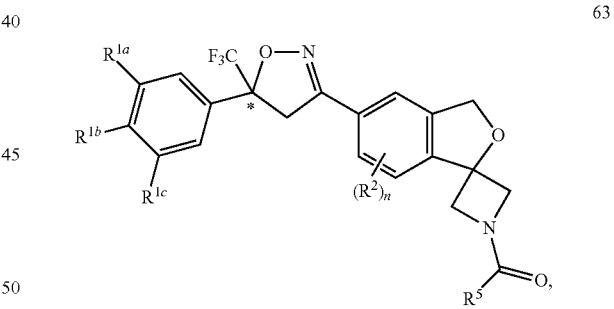

wherein $R^{1a}$, $R^{1b}$, and $R^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$cycloalkyl, $C_1$-$C_6$haloalkoxy, —C(O)NH$_2$, —SF$_5$, or —S(O)$_p$R;

$R^2$ is halo, cyano, $C_1$-$C_6$alkyl, $C_1$-$C_6$haloalkyl, nitro, hydroxyl, —C(O)NR$^a$R$^b$, $C_2$-$C_6$alkenyl, $C_2$-$C_6$alkynyl, —S(O)$_p$R, or —OR;

$R^5$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;

$R^7$ is hydrogen, $C_1$-$C_6$alkyl, hydroxyl, cyano, nitro, —S(O)$_p$R$^c$, or $C_1$-$C_6$alkoxy;

R is $C_1$-$C_6$alkyl or $C_3$-$C_6$cycloalkyl optionally substituted with at least one halo substituent;

$R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

$R^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R, —SCN, or —C(O)NR$^a$R$^b$;

wherein $R^5$ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, hydroxy$C_1$-$C_6$alkyl-, $C_1$-$C_6$haloalkyl, —S(O)$_p$R$^c$, —SH, —S(O)$_p$NR$^a$R$^b$, —NR$^a$R$^b$, —NR$^a$C(O)R$^b$, —SC(O)R, —SCN, or —C(O)NR$^a$R$^b$; and wherein $R^5$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =NR$^7$, hydroxyl, $C_1$-$C_6$alkoxy, $C_1$-$C_6$alkyl, hydroxy$C_1$-$C_6$alkyl-, $C_1$-$C_6$haloalkyl, —SH, —S(O)$_p$R, and $C_1$-$C_6$haloalkoxy;

n is the integer 0, 1, or 2, and when n is 2, each $R^2$ may be identical or different from each other;

p is the integer 0, 1, or 2; and

* depicts a chiral center, stereoisomers thereof, and veterinarily acceptable salts thereof, said process comprising, optionally in a solvent, a) metallating an iodobromobenzyl derivative of Formula 57 with a Grignard reagent or halogen-metal exchange with an alkyllithium and reacting with a protected azetidinone in a one-pot process or in a step-wise process to provide a compound of Formula 58, wherein $Y^2$ is bromine, chlorine, iodine, hydroxyl, or a sulfonate leaving group;

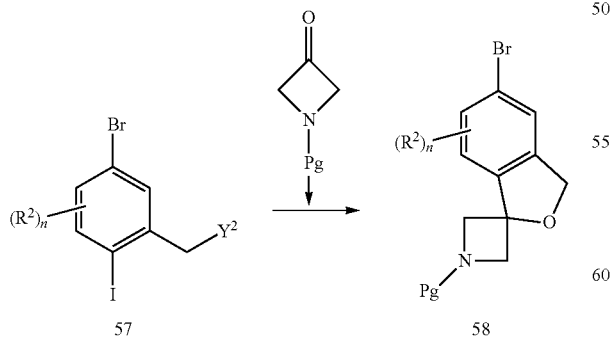

b) palladium catalyzed condensation of a compound of Formula 58 with a vinyl ether to provide a compound of Formula 59, wherein $R^8$ is a $C_1$-$C_6$alkyl;

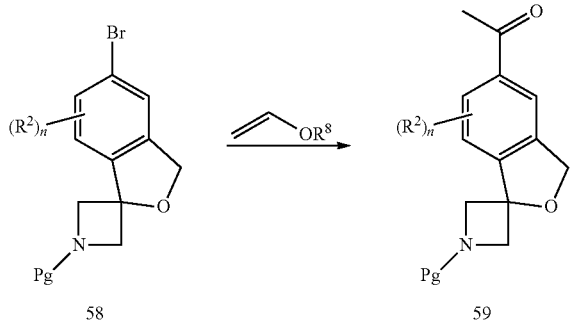

c) condensation of a compound of Formula 59 with a substituted trifluoroacetophenone of Formula 56 to provide a compound of Formula 60;

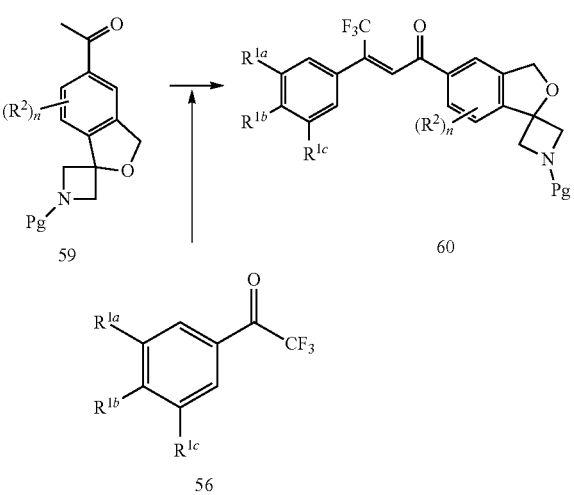

d) addition of hydroxylamine to a compound of Formula 60 and cyclization in the presence of a quinine based chiral catalyst to provide a compound of Formula 61;

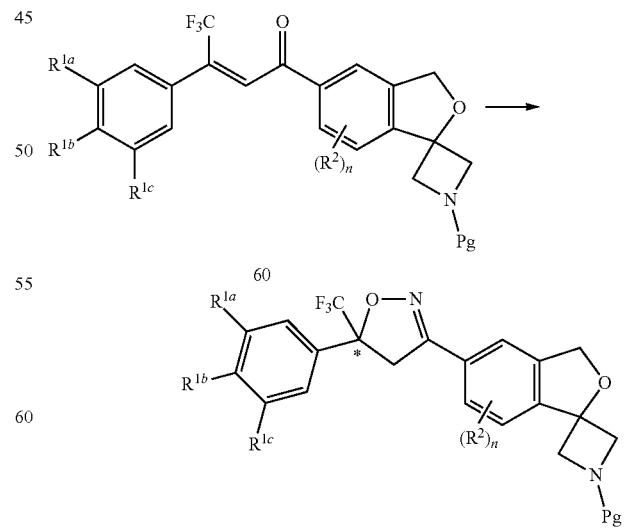

e) removal of the azetidine protecting group of the compound of Formula 61 to provide a compound of Formula 62; and

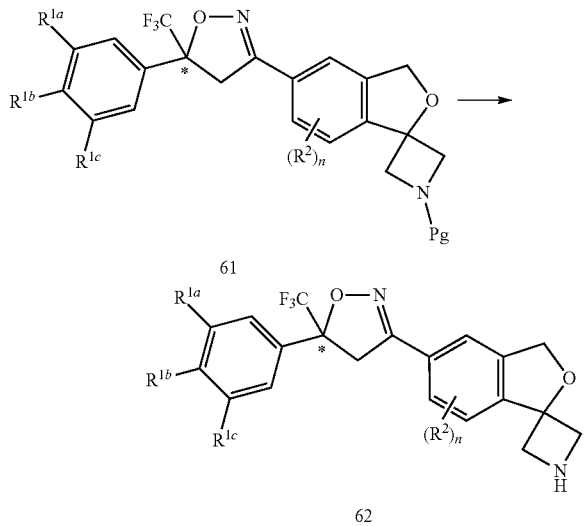

61

62 f) coupling the compound of Formula 62 with an acid or acid chloride under standard amide formation conditions to provide a compound of Formula 63.

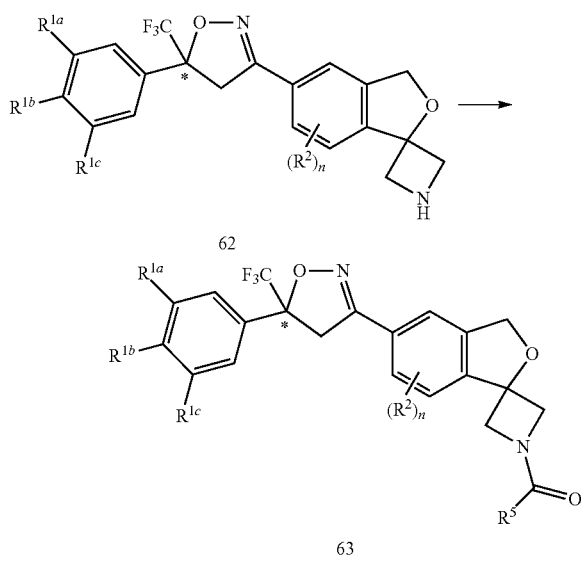

62

63

In another aspect of the invention, is a process for preparing the chiral spiroisoxazolines of Formula (63) of Scheme 16, wherein $R^{1a}$, $R^{1b}$, and $R^{1c}$ are each independently hydrogen, halo, or $C_1$-$C_6$haloalkyl; $R^5$ is $C_1$-$C_6$alkyl, $C_0$-$C_6$alkyl$C_3$-$C_6$cycloalkyl, $C_0$-$C_6$alkylheteroaryl, or $C_0$-$C_6$alkylheterocycle; wherein $R^5$ $C_1$-$C_6$alkyl or $C_0$-$C_6$alkyl$C_3$-$C_6$cycloalkyl moiety can be optionally and independently substituted by at least one substituent selected from halo, hydroxyl, hydroxy$C_1$-$C_6$alkyl-, $C_1$-$C_6$haloalkyl, or —S(O)$_p$R$^c$; and wherein $R^5$ $C_0$-$C_6$alkylheteroaryl or $C_0$-$C_6$alkylheterocycle moiety can be further optionally substituted with at least one substituent selected from oxo, hydroxyl, hydroxy$C_1$-$C_6$alkyl-, $C_1$-$C_6$alkyl, or $C_1$-$C_6$haloalkyl; $R^c$ is $C_1$-$C_6$alkyl;

n is the integer 0; and
p is the integer 0, 1, or 2;
stereoisomers thereof, and veterinarily acceptable salts thereof.

In another aspect of the invention, is a process for preparing the chiral spiroisoxazolines of Formula (63) of Scheme 16, wherein $R^{1a}$, $R^{1b}$, and $R^{1c}$ are each independently hydrogen, chloro, fluoro, bromo, or trifluoromethyl;

$R^5$ is methyl, ethyl, propyl, isopropyl, butyl, isobutyl, t-butyl, cyclopropyl, or cyclobutyl, wherein each substituent can be optionally and independently substituted by at least one substituent selected from halo, hydroxyl, $C_1$-$C_6$haloalkyl, or —S(O)$_p$R$^c$; or $R^5$ is thietanyl, pyrazolyl, or —CH$_2$pyrazolyl, wherein each substituent can be further optionally substituted with at least one substituent selected from oxo, or $C_1$-$C_6$alkyl; and $R^c$ is methyl or ethyl; stereoisomers thereof, and veterinarily acceptable salts thereof.

In another aspect of the invention, is a process for preparing the chiral spiroisoxazolines of Formula (63) of Scheme 16, comprising, optionally in a solvent, wherein the iodobromobenzyl derivative is 4-bromo-2-(chloromethyl)-1-iodobenzene and the protected azetidinone is 3-oxooazetidine-1-carboxylic acid tert-butyl ester or 1-benzhydrylazetidin-3-one.

In another aspect of the invention, is a process for preparing the chiral spiroisoxazolines of Formula (63) of Scheme 16, wherein $R^{1a}$ and $R^{1c}$ are each chloro, $R^{1b}$ is fluoro, and $R^5$ is —CH$_2$S(O)$_2$CH$_3$; stereoisomers thereof, and veterinarily acceptable salts thereof.

In another aspect of the invention, are compounds selected from the group consisting of:
tert-butyl 5'-bromo-3'H-spiro[azetidine-3,1'-isobenzofuran]-1-carboxylate;
1-benzhydryl-5'-bromo-3'H-spiro[azetidine-3,1'-isobenzofuran];
tert-butyl 5'-acetyl-3'H-spiro[azetidine-3,1'-isobenzofuran]-1-carboxylate;
1-(1-benzhydryl-3'H-spiro[azetidine-3,1'-isobenzofuran]-5'-yl)ethanone;
tert-butyl 5'-(3-(3,5-dichloro-4-fluorophenyl)-4,4,4-trifluorobut-2-enoyl)-3'H-spiro[azetidine-3,1'-isobenzofuran]-1-carboxylate;
(R)-tert-butyl 5'-(5-(3,5-dichloro-4-fluorophenyl)-5-(trifluoromethyl)-4,5-dihydroisoxazol-3-yl)-3'H-spiro[azetidine-3,1'-isobenzofuran]-1-carboxylate;
(S)-tert-butyl 5'-(5-(3,5-dichloro-4-fluorophenyl)-5-(trifluoromethyl)-4,5-dihydroisoxazol-3-yl)-3'H-spiro[azetidine-3,1'-isobenzofuran]-1-carboxylate;
(E/Z)-1-(1-benzhydryl-3'H-spiro[azetidine-3,1'-isobenzofuran]-5'-yl)-3-(3,5-dichloro-4-fluorophenyl)-4,4,4-trifluorobut-2-en-1-one;
tert-butyl 5'-(5-(3,5-dichloro-4-fluorophenyl)-5-(trifluoromethyl)-4,5-dihydroisoxazol-3-yl)-3'H-spiro[azetidine-3,1'-isobenzofuran]-1-carboxylate;
(R)-5'-(5-(3,5-dichloro-4-fluorophenyl)-5-(trifluoromethyl)-4,5-dihydroisoxazol-3-yl)-3'H-spiro[azetidine-3,1'-isobenzofuran]para-toluene sulfonate;
(S)-5'-(5-(3,5-dichloro-4-fluorophenyl)-5-(trifluoromethyl)-4,5-dihydroisoxazol-3-yl)-3'H-spiro[azetidine-3,1'-isobenzofuran]para-toluene sulfonate;
1-benzhydryl-5'-(5-(3,5-dichloro-4-fluorophenyl)-5-(trifluoromethyl)-4,5-dihydroisoxazol-3-yl)-3'H-spiro[azetidine-3,1'-isobenzofuran];
(R)-1-benzhydryl-5'-(5-(3,5-dichloro-4-fluorophenyl)-5-(trifluoromethyl)-4,5-dihydroisoxazol-3-yl)-3'H-spiro[azetidine-3,1'-isobenzofuran]

(S)-1-benzhydryl-5'-(5-(3,5-dichloro-4-fluorophenyl)-5-(trifluoromethyl)-4,5-dihydroisoxazol-3-yl)-3'H-spiro[azetidine-3,1'-isobenzofuran]; and 5'-(5-(3,5-dichloro-4-fluorophenyl)-5-(trifluoromethyl)-4,5-dihydroisoxazol-3-yl)-3'H-spiro[azetidine-3,1'-isobenzofuran]para-toluene sulfonate, or a stereoisomer thereof, or a veterinarily acceptable salt thereof.

In another aspect of the invention, is a veterinary composition that comprises a) a Formula (V.1), Formula (V.2), Formula (V.1.1), and Formula (1) compounds, stereoisomers thereof, or a veterinarily acceptable salt thereof, and (b) a veterinarily acceptable excipient, diluent, or carrier. Preferably, the composition comprises a therapeutically effective amount of a Formula (V.1), Formula (V.2), Formula (V.1.1), and Formula (1) compounds, stereoisomer thereof, or veterinarily acceptable salt thereof, and a veterinarily acceptable excipient, diluent, or carrier.

The composition may comprise at least one additional veterinary agent. Preferred additional veterinary agents include endoparasiticides, endectocides, ectoparasiticides, insecticides, and anthelmintics, and are described herein. In one aspect of the invention, the additional veterinary agent is selected from amitraz, amino acetonitriles, anthelmintics (e.g., albendazole, cambendazole, fenbendazole, flubendazole, mebendazole, octadepsipeptides, oxfendazole, oxibendazole, paraherquamide, parbendazole, piperazines, praziquantel, thiabendazole, tetramisole, triclabendazole, levamisole, pyrantel pamoate, oxantel, morantel, and the like), avermectins (e.g., abamectin, doramectin, emamectin, eprinomectin, ivermectin, moxidectin, selamectin, and the like), milbemycin, milbemycin oxime, demiditraz, diethylcarbamazine, fipronil, hydroprene, kinoprene, methoprene, metaflumizone, niclosamide, permethrin, pyrethrins, pyriproxyfen, and spinosad. In another aspect of the invention, the additional agent is selected from an amino acetonitrile, albendazole, cambendazole, fenbendazole, flubendazole, mebendazole, oxfendazole, oxibendazole, paraherquamide, parbendazole, praziquantel, thiabendazole, tetramisole, triclabendazole, levamisole, pyrantel pamoate, oxantel, morantel, abamectin, doramectin, emamectin, eprinomectin, ivermectin, moxidectin, selamectin, milbemycin, milbemycin oxime, demiditraz, diethylcarbamazine, fipronil, hydroprene, kinoprene, methoprene, metaflumizone, niclosamide, pyriproxyfen, and spinosad. In yet another aspect of the invention, the additional agent is selected from an amino acetonitrile, paraherquamide, praziquantel, abamectin, doramectin, emamectin, eprinomectin, ivermectin, moxidectin, selamectin, milbemycin, and milbemycin oxime. In yet another aspect of the invention, the additional agent is selected from abamectin, doramectin, emamectin, eprinomectin, ivermectin, moxidectin, selamectin, milbemycin, and milbemycin oxime. In yet another aspect of the invention, the additional agent is selected from abamectin, doramectin, eprinomectin, ivermectin, moxidectin, selamectin, milbemycin, and milbemycin oxime. In yet another aspect of the invention, the additional agent is selected from moxidectin, selamectin, and milbemycin oxime. In yet another aspect of the invention, the additional agent is selected from moxidectin and milbemycin oxime.

In yet another aspect of the invention is the use of a Formula (V.1), Formula (V.2), Formula (V.1.1), and Formula (1) compound for the manufacture of a medicament.

In yet another aspect of the invention is a method for treating a parasitic infection or infestation in an animal that includes the step of administering to said animal, in need of such treatment, a therapeutically effective amount of a compound of the present invention, stereoisomer thereof, or veterinarily acceptable salt thereof. In one aspect, the animal is a mammal, specifically a companion animal (for example, dog, cat, or horse) or livestock (for example, sheep, goat, cattle, and pig). In another aspect, the animal is a bird, specifically, fowl (for example, chicken, turkey, duck, and geese). In another aspect, the animal is a fish. The compounds of the present invention, and compositions thereof, can be administered to the animal orally or topically. The compounds of the present invention, and compositions thereof, can also be administered to the animal by intramuscular-, intraperitoneal-, or subcutaneous-injection. Preferably, the compounds of the present invention, and compositions thereof, can be administered to the animal orally or topically.

In yet another aspect of the invention is a method for treating a parasitic infection or infestation in an animal that includes the step of administering to said animal, in need of such treatment, a therapeutically effective amount of a compound of the present invention, stereoisomer thereof, or veterinarily acceptable salt thereof, in combination with at least one additional veterinary agent. In one aspect, the animal is a mammal, specifically a companion animal (for example, dog, cat, or horse) or livestock (for example, sheep, goat, cattle, and pig). In another aspect, the animal is a bird, specifically, fowl (for example, chicken, turkey, duck, and geese). In another aspect, the animal is a fish. The compounds of the present invention, and compositions thereof, can be administered to the animal orally or topically. The compounds of the present invention, and compositions thereof, can also be administered to the animal by intramuscular-, intraperitoneal-, or subcutaneous-injection. Preferably, the compounds of the present invention, and compositions thereof, can be administered to the animal orally or topically. Equally preferred, the compounds of the present invention can be administered by injection.

Compounds of the present invention alone, or in combination with an additional veterinary agent(s) may be administered as (a) a single veterinary composition which comprises a compound of the present invention, stereoisomer thereof, veterinarily acceptable salt thereof, and optionally, at least one additional veterinary agent as described herein and a veterinarily acceptable excipient, diluent, or carrier; or (b) two separate veterinary compositions comprising (i) a first composition comprising a compound of the present invention, stereoisomer thereof, veterinarily acceptable salt thereof, and a veterinarily acceptable excipient, diluent, or carrier, and (ii) a second composition comprising at least one additional veterinary agent, as described herein and a veterinarily acceptable excipient, diluent, or carrier. The veterinary compositions may be administered simultaneously or sequentially and in any order.

All of the recited WO patent publications herein are incorporated by reference.

Definitions

For purposes of the present invention, as described and claimed herein, the following terms and phrases are defined as follows:

"Additional veterinary agent(s)" as used herein, unless otherwise indicated, refers to other veterinary or pharmaceutical compounds or products that provide a therapeutically effective amount of said agents that are useful for the treatment of a parasitic infection in an animal, as described herein.

"Alkoxy", as used herein, unless otherwise indicated, refers to an oxygen moiety having a further alkyl substituent. The alkyl portion (i.e., alkyl moiety) of an alkoxy group has the same definition as below. Non-limiting examples include: —OCH$_3$, —OCH$_2$CH$_3$, and the like.

"Alkyl", as used herein, unless otherwise indicated, refers to saturated monovalent hydrocarbon alkane radicals of the general formula C$_n$H$_{2n+1}$. The alkane radical may be straight or branched and may be unsubstituted or substituted. For example, the term "(C$_1$-C$_6$)alkyl" refers to a monovalent, straight or branched aliphatic group containing 1 to 6 carbon atoms. Non-exclusive examples of (C$_1$-C$_6$) alkyl groups include, but are not limited to methyl, ethyl, propyl, isopropyl, sec-butyl, t-butyl, n-propyl, n-butyl, i-butyl, s-butyl, n-pentyl, 1-methylbutyl, 2-methylbutyl, 3-methylbutyl, neopentyl, 3,3-dimethylpropyl, 2-methylpentyl, hexyl, and the like. The alkyl moiety may be attached to the chemical moiety by any one of the carbon atoms of the aliphatic chain. Alkyl groups are optionally substituted as described herein. Further when used in compound words such as alkylphenyl, said alkyl moiety has the same meaning as herein defined and may be attached to the chemical moiety by any one of the carbon atoms of the aliphatic chain. Non-limiting examples of the compound word, alkylphenyl include: C$_1$alkylphenyl is —CH$_2$-phenyl, C$_2$alkylphenyl is —CH$_2$CH$_2$-phenyl, C$_0$phenyl is phenyl, and the like.

"Alkenyl" as used herein, unless otherwise indicated, refers to a straight or branched aliphatic hydrocarbon chain having 2- to 6-carbon atoms and containing at least one carbon-carbon double bond (for example —C═C—, or —C═CH$_2$). Non-exclusive examples of alkenyl include: ethenyl, 1-propenyl, 2-propenyl, isopropenyl, 1-butenyl, 2-butenyl, 3-butenyl, 2-pentenyl, and the like.

"Alkynyl" as used herein, unless otherwise indicated, refers to straight or branched aliphatic hydrocarbon chain having 2- to 6-carbon atoms and containing at least one carbon-carbon triple bond (for example, —C≡C— or —C≡CH$_2$). Non-exclusive examples of alkynyl include: ethynyl, 2-propynyl, 1-methyl-2-propynyl, 2-butynyl, 3-butynyl, 2-methyl-3-butynyl, and the like.

"Animal(s)", as used herein, unless otherwise indicated, refers to an individual animal that is a mammal, bird, or fish. Specifically, mammal refers to a vertebrate animal that is human and non-human, which are members of the taxonomic class Mammalia. Non-exclusive examples of non-human mammals include companion animals and livestock. Non-exclusive examples of a companion animal include: dog, cat, llama, and horse. Preferred companion animals are dog, cat, and horse. More preferred is dog. Non-exclusive examples of livestock include: swine, camel, rabbits, goat, sheep, deer, elk, bovine (cattle), and bison. Preferred livestock is cattle and swine. Specifically, bird refers to a vertebrate animal of the taxonomic class Aves. Birds are feathered, winged, bipedal, endothermic, and egg-laying. Non-exclusive examples of bird include, poultry (e.g., chicken, turkey, duck, and geese), all of which are also referred to herein as fowl. Specifically, fish refers to the taxonomic class Chondrichthyes (cartilaginous fishes, e.g., sharks and rays) and Osteichthyes (bony fishes) which live in water, have gills or mucus-covered skin for respiration, fins, and may have scales. Non-exclusive examples of fish include shark, salmon, trout, whitefish, catfish, tilapia, sea bass, tuna, halibut, turbot, flounder, sole, striped bass, eel, yellowtail, grouper, and the like.

"Carbocyclic", as used herein, unless otherwise indicated, refers to a partially saturated or saturated 5- to 7-membered ring containing only carbon atoms and can be monocyclic or part of a fused ring or spiro ring moiety. Examples of carbocyclic rings include cyclopentane, cyclohexane, and cycloheptane. The carbocyclic ring is optionally substituted as described herein.

"Chiral", as used herein, unless otherwise indicated, refers to the structural characteristic of a molecule that makes it impossible to superimpose it on its mirror image, (e.g., "R" and "S" enantiomers). The term is also depicted as an asterisk (i.e.,*) in the Eamples and preparations and refers to a chiral center which includes both the S and R enantiomers.

"Compounds of the present invention", as used herein, unless otherwise indicated, refers to compounds of Formula (V.1), Formula (V.2), Formula (V.1.1), and Formula (1) compounds, and stereoisomers thereof.

"Cycloalkyl", as used herein, unless otherwise indicated, includes fully saturated or partially saturated carbocyclic alkyl moieties. Non-limiting examples of partially saturated cycloalkyls include: cyclopropene, cyclobutene, cycloheptene, cyclooctene, cyclohepta-1,3-diene, and the like. Preferred cycloalkyls are 3- to 6-membered saturated monocyclic rings including cyclopropyl, cyclobutyl, cyclopentyl, and cyclohexyl. The cycloalkyl group may be attached to the chemical moiety by any one of the carbon atoms within the carbocyclic ring. Cycloalkyl groups are optionally substituted with at least one substituent. Further when used in compound words such as alkylcycloalkyl, said alkyl and cycloalkyl moiety has the same meaning as herein defined and may be attached to the chemical moiety by any one of the carbon atoms of the aliphatic chain. Examples of C$_0$-C$_6$alkylC$_3$-C$_6$cycloalkyl include, methylcyclopropane (C$_1$alkylC$_3$cycloalkyl or —CH$_2$cyclopropane), ethylcyclopropane (C$_2$alkylC$_3$cycloalkyl or —CH$_2$CH$_2$cyclopropane), methylcyclobutane (C$_1$alkylC$_4$cycloalkyl or —CH$_2$cyclobutane), ethylcyclobutane (C$_2$alkylC$_4$cycloalkyl or —CH$_2$CH$_2$cyclobutane), methylcyclohexane (C$_1$alkylC$_6$cycloalkyl or —CH$_2$cyclohexane), and the like. C$_0$alkylC$_3$-C$_6$cycloalkyl is C$_3$-C$_6$cycloalkyl. Cycloalkyl moieties are optionally substituted as described herein "Halogen" or "halo", as used herein, unless otherwise indicated, refers to fluorine, chlorine, bromine and iodine. Further, when used in compound words such as "haloalkyl", "haloalkoxy", "haloalkenyl", or "haloalkynyl", said alkyl, alkoxy, alkenyl, and alkynyl may be partially or fully substituted with halogen atoms which may be the same or different and said alkyl, alkoxy, alkenyl, and alkynyl moiety has the same meaning as above and may be attached to the chemical moiety by any one of the carbon atoms of the aliphatic chain. Examples of "haloalkyl" include F$_3$C—, ClCH$_2$—, CF$_3$CH$_2$— and CF$_3$CCl$_2$—, and the like. The term "haloalkoxy" is defined analogously to the term "haloalkyl". Examples of "haloalkoxy" include CF$_3$O—, CCl$_3$CH$_2$O—, HCF$_2$CH$_2$CH$_2$O— and CF$_3$CH$_2$O—, and the like. The term "haloalkenyl is defined analogously to the term "haloalkyl" except that the aliphatic chain contains at least one carbon-carbon double bond. Examples of "haloalkenyl" include CF$_3$C═C—, CCl$_3$C═C—, HCF$_2$C═C— and CF$_3$C═CC—, and the like. The term "haloalkynyl" is defined analogously to the term "haloalkyl" except that the aliphatic chain contains at least one carbon-carbon triple bond. Examples of "haloalkynyl" include CF$_3$C≡C—, CCl$_3$C≡C—, HCF$_2$C≡C— and CF$_3$C≡CC—, and the like.

"Heteroaryl" or "Het", as used herein, unless otherwise indicated, refers to a 5- to 6-membered aromatic monocyclic ring or an 8- to 10-membered fused aromatic ring where said monocyclic- and fused-ring moiety contains one or more heteroatoms each independently selected from N, O, or S, preferably from one to four heteroatoms. Non-exclusive examples of monocyclic heteroaryls include pyrrolyl, furanyl, thiophenyl, pyrazolyl, imidazolyl, triazolyl, tetrazolyl, thiazolyl, isoxazolyl, oxazolyl, oxadiazolyl, thiadiazolyl, pyridinyl, pyridazinyl, pyrimidinyl, pyrazinyl, and the like.

Non-exclusive examples of fused heteroaryls include: benzofuranyl, benzothiophenyl, indolyl, benzimidazolyl, indazolyl, benzotriazolyl, thieno[2,3-c]pyridine, thieno[3,2-b]pyridine, benzo[1,2,5]thiadiazole, and the like. The heteroaryl group may be attached to the chemical moiety by any one of the carbon atoms or nitrogen heteroatoms within the monocyclic or fused ring. Further when used in compound words such as alkylheteroaryl, said alkyl and heteroaryl moiety have the same meaning as herein defined and may be attached to the chemical moiety by any one of the carbon atoms of the aliphatic chain. For example, $C_0$alkylheteroaryl is heteroaryl, $C_1$alkylheteroaryl is —$CH_2$heteroaryl, $C_2$alkylheteroaryl is —$CH_2CH_2$heteroaryl, and the like. Heteroaryls are optionally substituted as described herein.

"Heterocycle", as used herein, unless otherwise indicated, refers to a partially saturated or saturated 3- to 7-membered monocyclic ring containing one or more heteroatoms each independently selected from N, O, or S, preferably from one to four heteroatoms. The heterocyclic ring can be part of a fused ring or spiro-ring moiety. Non-exclusive examples of heterocycle include oxirane, thiarane, aziridine, oxetane, azetidine, thiatane, tetrahydrofuran, tetrahydrothiophene, pyrrolidine, tetrahydropyrane, piperidine, piperazine, tetrahydropyridine, 2H-azirine, 2,3-dihydro-azete, 3,4-dihydro-2H-pyrrole, and the like. The heterocycle group may be attached to the chemical moiety by any one of the carbon atoms or nitrogen heteroatoms within the ring. Further when used in compound words such as alkylheterocycle, said alkyl and heterocycle moiety have the same meaning as herein defined and may be attached to the chemical moiety by any one of the carbon atoms of the aliphatic chain. For example, $C_0$alkylheterocycle is heterocycle, $C_1$alkylheterocycle is —$CH_2$heterocycle, $C_2$alkylheterocycle is —$CH_2CH_2$heterocycle, and the like. Heterocycles are optionally substituted as described herein.

"Optionally substituted", is used herein interchangeably with the phrase substituted or unsubstituted. Unless otherwise indicated, an optionally substituted group may have a substituent at each substitutable position of the group, and each substitution is independent of the other. An optionally substituted group also may have no substituents. Therefore, the phrase "optionally substituted with at least one substituent" means that the number of substituents may vary from zero up to a number of available positions for substitution.

"Parasite(s)", as used herein, unless otherwise indicated, refers to endoparasites and ectoparasites. Endoparasites are parasites that live within the body of its host and include helminths (e.g., trematodes, cestodes, and nematodes) and protozoa. Ectoparasites are organisms of the Arthropoda phylum (e.g., arachnids, insects, and crustaceans (e.g., copepods-sea lice) which feed through or upon the skin of its host. Preferred arachnids are of the order Acarina, e.g., ticks and mites. Preferred insects are midges, fleas, mosquitos, biting flies (stable fly, horn fly, blow fly, horse fly, and the like), bed bugs, and lice. Preferred compounds of the present invention can be used for the treatment of parasites, i.e., treatment of a parasitic infection or infestation.

"Protecting group" or "Pg", as used herein, unless otherwise indicated, refers to a substituent that is commonly employed to block or protect an amine on the compound thereby protecting its functionality while allowing for the reaction of other functional groups on the compound. Non-exclusive examples of an amine-protecting group include: acyl groups (e.g., formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl, and the like), acyloxy groups (e.g., 1-tert-butyloxycarbonyl (Boc), methoxycarbonyl, 9-fluorenyl-methoxycarbonyl, 2,2,2-trifluoroethoxy-carbonyl, 2-trimethylsilylethxoycarbonyl, vinyloxycarbonyl, allyloxycarbonyl, 1,1-dimethyl-propynyloxycarbonyl, benzyloxy-carbonyl, p-nitrobenzyloxycarbonyl, 2,4-dichlorobenzyloxycarbonyl, and the like), diphenylmethane, and benzylcarbamates.

"Sulfonate leaving group", as used herein, unless otherwise indicated, refers to anions with the general formula $RSO_2O^-$. Non limiting examples of a sulfonate leaving group include: mesylate (R=$CH_3$), triflate (R=$CF_3$), tosylate (R=$CH_3C_6H_4$), besylate (R=$C_6H_5$), tresylate (R=$CH_2CF_3$), and the like.

"Therapeutically effective amount", as used herein, unless otherwise indicated, refers to an amount of the compounds of the present invention that (i) treat the particular parasitic infection or infestation, (ii) attenuates, ameliorates, or eliminates one or more symptoms of the particular parasitic infection or infestation, or (iii) prevents or delays the onset of one or more symptoms of the particular parasitic infection or infestation described herein.

"Treatment", "treating", and the like, as used herein, unless otherwise indicated, refers to reversing, alleviating, or inhibiting the parasitic infection, infestation, or condition. As used herein, these terms also encompass, depending on the condition of the animal, preventing the onset of a disorder or condition, or of symptoms associated with a disorder or condition, including reducing the severity of a disorder or condition or symptoms associated therewith prior to affliction with said infection or infestation. Thus, treatment can refer to administration of the compounds of the present invention to an animal that is not at the time of administration afflicted with the infection or infestation. Treating also encompasses preventing the recurrence of an infection or infestation or of symptoms associated therewith as well as references to "control" (e.g., kill, repel, expel, incapacitate, deter, eliminate, alleviate, minimize, and eradicate).

"Veterinary acceptable" as used herein, unless otherwise indicated, indicates that the substance or composition must be compatible chemically and/or toxicologically, with the other ingredients comprising a formulation, composition, and/or the animal being treated therewith. The term "pharmaceutically" acceptable has the same meaning as that recited for "veterinarily" acceptable.

DETAILED DESCRIPTION

The present invention provides Formula (V.1), Formula (V.2), Formula (V.1.1), and Formula (1) compounds, stereoisomers thereof, as well as veterinary compositions that are useful as antiparasitic agents for animals, in particular, compounds that act as ectoparasiticides.

Compounds of the present invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, "Reagents for Organic Synthesis", 1; 19, Wiley, New York (1967, 1999 ed.), or *Beilsteins Handbuch der organischen Chemie,* 4, Aufl. ed. Springer-Verlag, Berlin, including supplements (also available via the Beilstein online database)). For illustrative purposes, the reaction schemes depicted below demonstrate potential routes for synthesizing compounds of the present invention, and key intermediates. For a more detailed description of the individual reaction steps, see the Examples section below. A skilled artisan will appreciate that other suitable starting materials, reagents, and synthetic routes may be used to synthesize the compounds of the present invention and a variety of derivatives thereof. Further, many of the compounds prepared by the methods described below can be further modified in light of this disclosure using conventional chemistry well known to the skilled artisan.

Compounds of the present invention described herein contain at least one asymmetric or chiral center; and, therefore, exist in different stereoisomeric forms. The R and S configurations are based upon knowledge of known chiral inversion/retention chemistry. Unless specified otherwise, it is intended that all stereoisomeric forms of the compounds of the present invention as well as mixtures thereof, including racemic mixtures and diastereomeric mixtures, form part of the present invention.

Enantiomeric mixtures can be separated into their individual enantiomers on the basis of their physical chemical differences by methods well known to those skilled in the art, such as chromatography and/or fractional crystallization. A more detailed description of techniques that can be used to resolve stereoisomers of compounds from their racemic mixture can be found in Jean Jacques Andre Collet, Samuel H. Wilen, Enantiomers, Racemates and Resolutions, John Wiley and Sons, Inc. (1981).

Compounds of this invention can exist as one or more stereoisomers. The various stereoisomers include enantiomers, diastereomers and atropisomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereo isomers or as an optically active form. For example, two possible enantiomers of Formula I are depicted as Formula 1a and Formula 1b involving the spirocyclic isoxazoline chiral center identified with an asterisk (*). Molecular depictions drawn herein follow standard conventions for depicting stereochemistry.

For illustrative purposes, the reaction schemes depicted below demonstrate potential routes for synthesizing key intermediates and compounds of the present invention. For a more detailed description of the individual reaction steps, see the Examples section below. Those skilled in the art will appreciate that other suitable starting materials, reagents, and synthetic routes may be used to synthesize the intermediates and compounds of the present invention and a variety of derivatives thereof. Further, many of the compounds prepared by the methods described below can be further modified in light of this disclosure using conventional chemistry. Schemes 1-17 outline the general procedures useful for the preparation and isolation of compounds of the present invention. It is to be understood, however, that the invention, as fully described herein and as recited in the claims, is not intended to be limited by the details of the following schemes or modes of preparation.

In the preparation of compounds of the present invention, protection of remote functionality of intermediates from undesired reactions can be accomplished with a protecting group. The term "protecting group" or "Pg" refers to a substituent that is commonly employed to block or protect a particular functionality while reacting other functional groups on the compound. For example, an amine-protecting group is a substituent attached to an amine that blocks or protects the amine-functionality of the compound or intermediate. Suitable amine protecting groups include: 1-tert-butyloxycarbonyl (Boc), acyl groups including: formyl, acetyl, chloroacetyl, trichloro-acetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl, and the like; and acyloxy groups including: methoxycarbonyl, 9-fluorenyl-methoxycarbonyl, 2,2,2-trifluoroethoxycarbonyl, 2-trimethylsilylethxoycarbonyl, vinyloxycarbonyl, allyloxycarbonyl, 1,1-dimethyl-propynyloxycarbonyl, benzyloxy-carbonyl, p-nitrobenzyloxycarbony, 2,4-dichlorobenzyloxycarbonyl, and the like. Similarly, diphenylmethane and benzylcarbamates can be used as amine protecting groups. Suitable protecting groups and their respective uses are readily determined by one skilled in the art. For a general description of protecting groups and their use, see T. W. Greene, *Protective Groups in Organic Synthesis*, John Wiley & Sons, New York, 1991.

In the Schemes and Examples below, the following catalysts/reactants and miscellaneous abbreviations include: mobile phase (MP); supercritical fluid chromatography (SFC); N,N-dimethyl formamide (DMF); dimethyl acetamide (DMA); acetonitrile (ACN or Acn); formic acid (FA); dichloromethane (DCM); N-chloro-succinimide (NCS); ethanol (EtOH); methyl tert-butyl ether (MTBE); triethylamine (TEA); methanol (MeOH), tetrahydrofuran (THF); ethyl acetate (EtOAc); trifluoroacetic acid (TFA); triphenylphosphine palladium (Pd(PPh$_3$)$_4$); (2,2,6,6-tetramethylpiperidin-1-yl)oxyl (TEMPO); and diisobutylaluminium hydride (DIBAL-H); 4-dimethylaminopyridine (DMAP); potassium bis(trimethylsilyl) (KHMDS); N-chlorosuccinimide (NCS); 1,3-bis(diphenylphosphino)propane (DPPP); amidecarbonyldiimidazole (CDI); 1-hydroxybenzotriazole hydrate (HOBt); and N,N,N',N'-Tetramethyl-O-(7-azabenzotriazol-1-yl)uronium hexafluorophosphate (HATU), methanesulfonyl chloride (mesyl chloride, MsCl); isopropylmagnesium chloride (iPrMgCl); t-butyloxycarbonyl (BOC); palladium(II) acetate (Pd(OAc)$_2$); and lithium borohydride (LiBH$_4$).

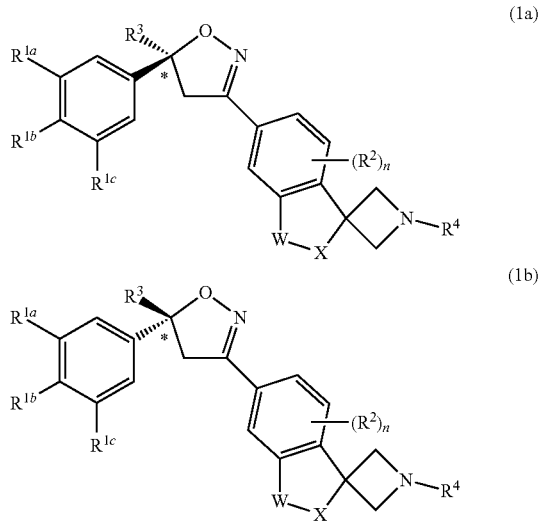

Scheme 1

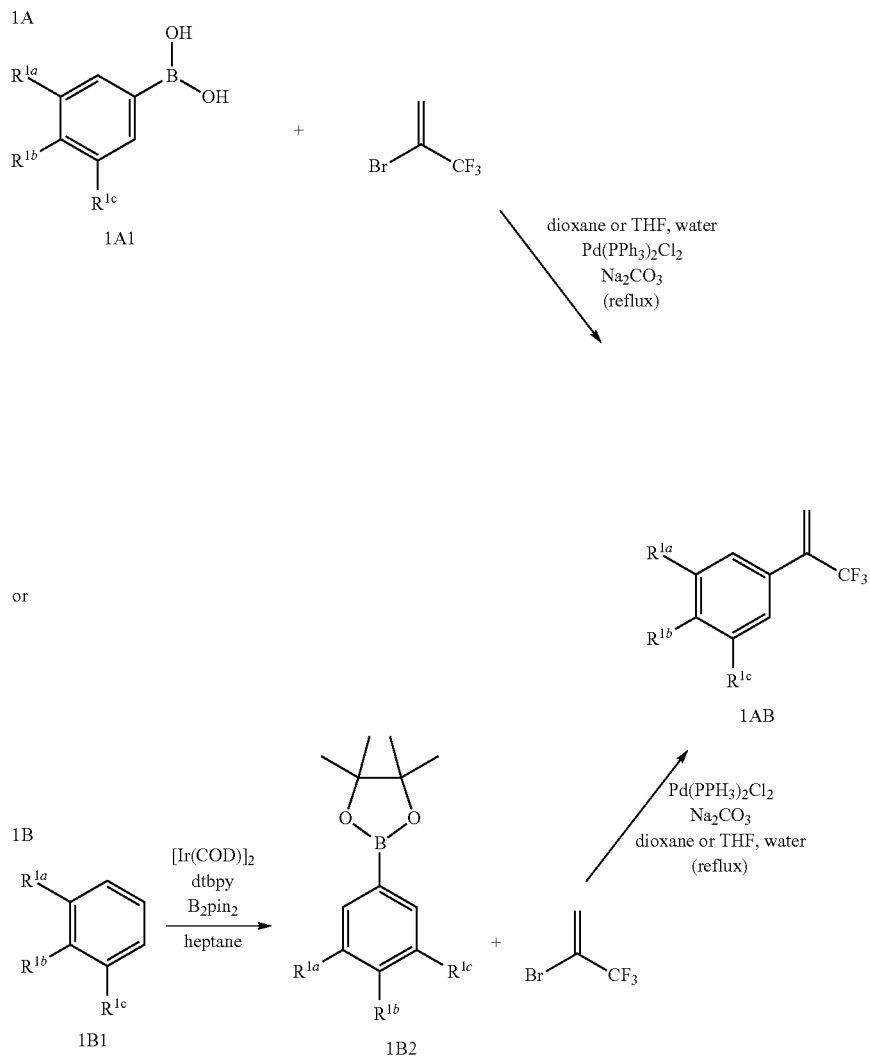

$R^{1a}$, $R^{1b}$, and $R^{1c}$ are as defined herein.

The aryl olefins (1AB) can be prepared according to Scheme 1. The requisite organoborates can be prepared as boronate ester intermediates (1B2) from literature methods (*Org. Lett.* 2007, 9, 761-764) or purchased as boronic acids (1A1) such as 3,5-dichloroboronic acid from Aldrich. Intermediate 1A1 or 1B2 compounds can be added to dioxane or THF and water, followed by 2-bromo-3,3,3-trifluoropropene, potassium carbonate, and bis(triphenylphosphine) palladium II chloride to afford the intermediate olefin (1AB) compounds.

Scheme 2

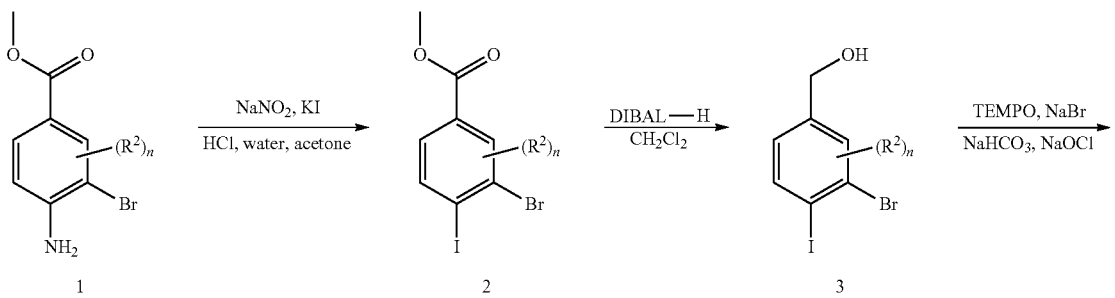

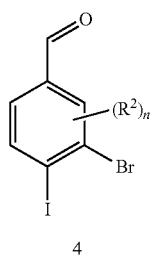
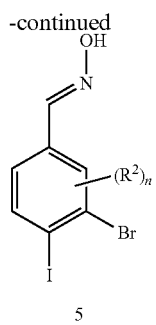
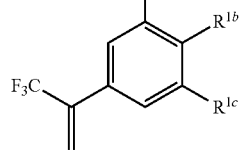
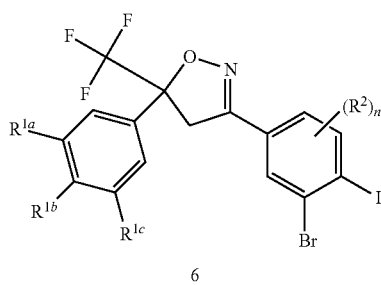
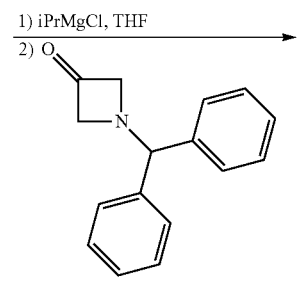
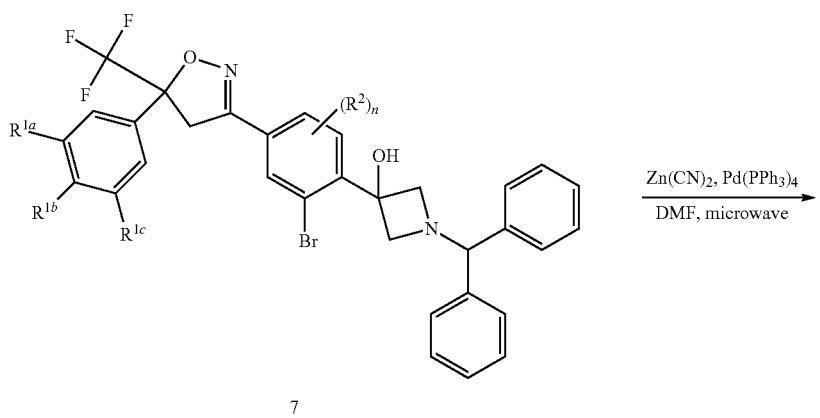
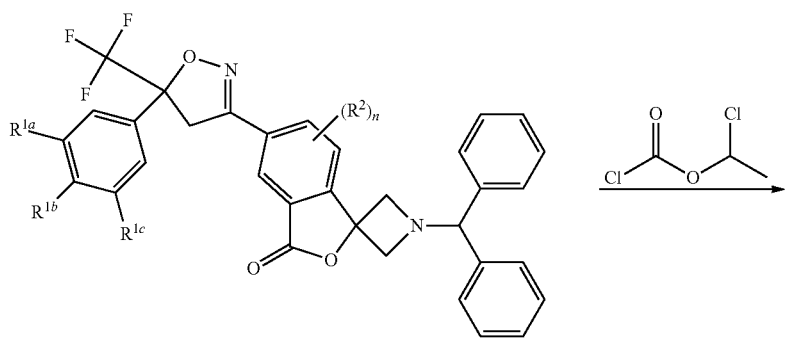

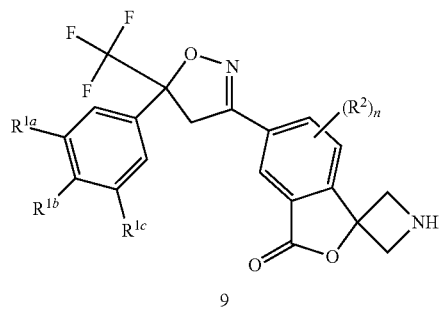

9

$R^{1a}$, $R^{1b}$, $R^{1c}$, $R^2$, and n are as defined herein.

The iodoester 2 can be prepared by treatment of the aminoester 1 with sodium nitrite and potassium iodide. Reduction of the ester to the alcohol with diisobutylaluminum hydride followed by oxidation with TEMPO or Dess-Martin affords the iodoaldehyde 4. This aldehyde can undergo condensation with hydroxylamine, chlorination and cyclization to give the isoxazoline 6. Grignard formation using iPrMgCl occurs selectively with the iodine and the resulting organometallic adds to the N-protected azetidinone to afford the phenylazetidine 7. Lactone 8 can be prepared through metal-catalyzed cyanation followed by intramolecular cyclization upon aqueous work-up. Removal of the benzhydryl protecting group with chloroethylchloroformate provides the spirocyclic azetidine 9.

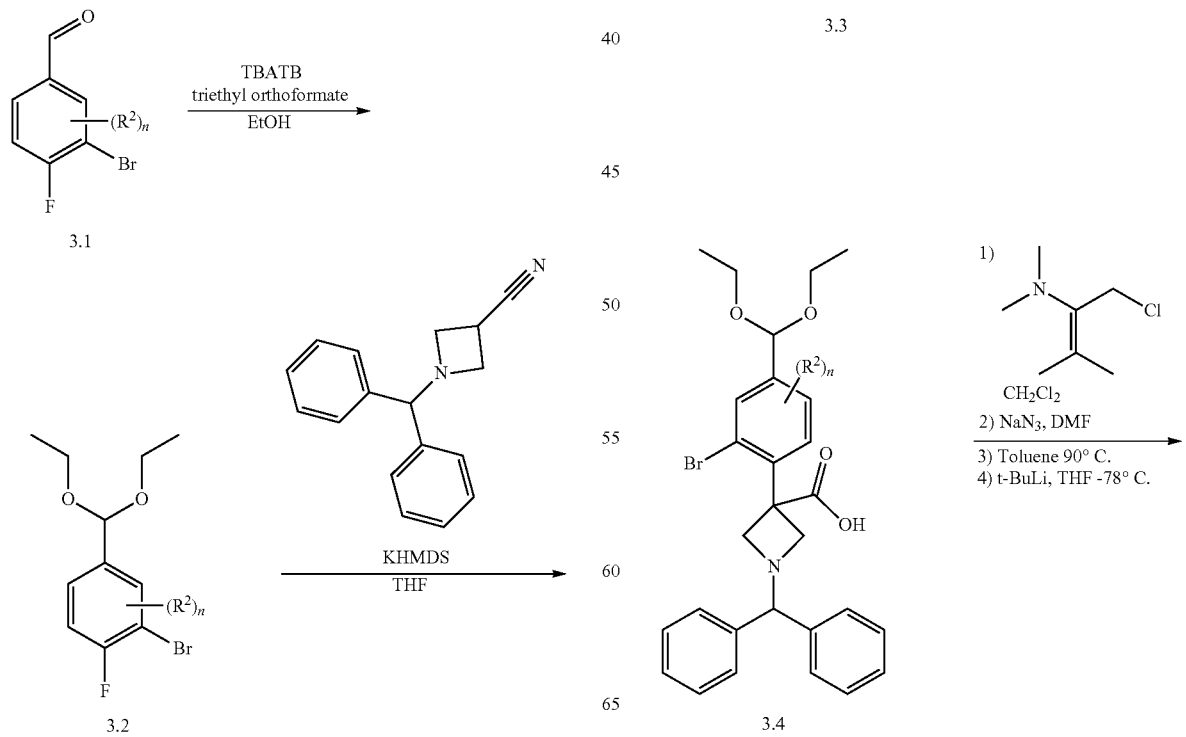

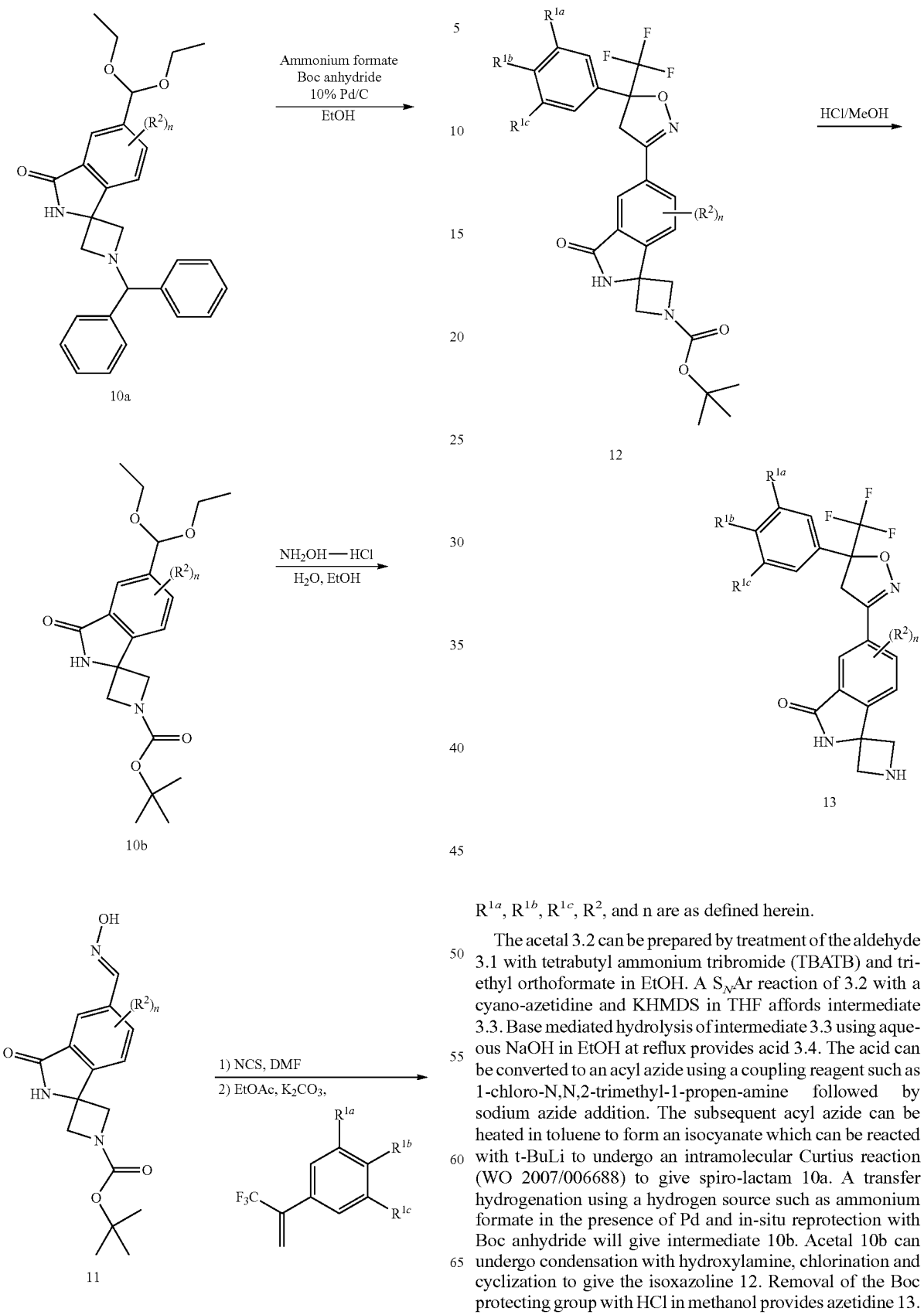

$R^{1a}$, $R^{1b}$, $R^{1c}$, $R^2$, and n are as defined herein.

The acetal 3.2 can be prepared by treatment of the aldehyde 3.1 with tetrabutyl ammonium tribromide (TBATB) and triethyl orthoformate in EtOH. A $S_NAr$ reaction of 3.2 with a cyano-azetidine and KHMDS in THF affords intermediate 3.3. Base mediated hydrolysis of intermediate 3.3 using aqueous NaOH in EtOH at reflux provides acid 3.4. The acid can be converted to an acyl azide using a coupling reagent such as 1-chloro-N,N,2-trimethyl-1-propen-amine followed by sodium azide addition. The subsequent acyl azide can be heated in toluene to form an isocyanate which can be reacted with t-BuLi to undergo an intramolecular Curtius reaction (WO 2007/006688) to give spiro-lactam 10a. A transfer hydrogenation using a hydrogen source such as ammonium formate in the presence of Pd and in-situ reprotection with Boc anhydride will give intermediate 10b. Acetal 10b can undergo condensation with hydroxylamine, chlorination and cyclization to give the isoxazoline 12. Removal of the Boc protecting group with HCl in methanol provides azetidine 13.

Scheme 4
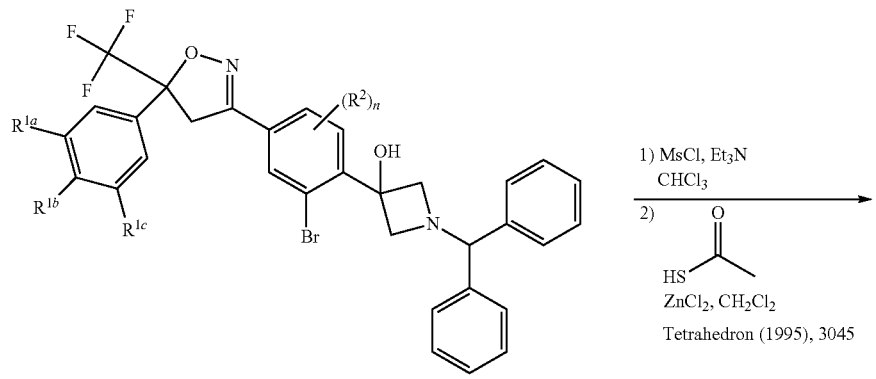
7
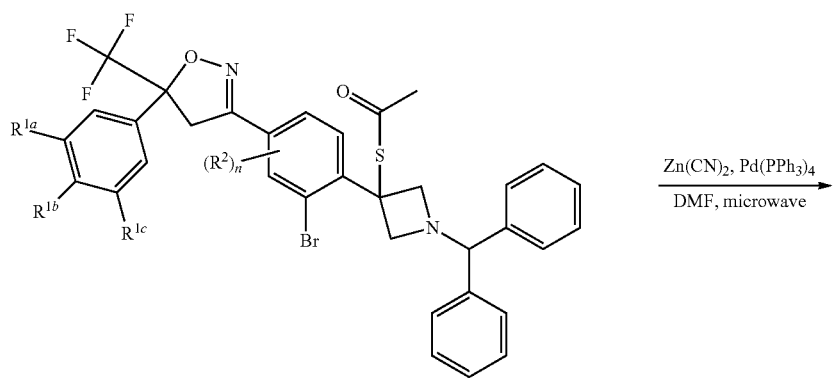
14
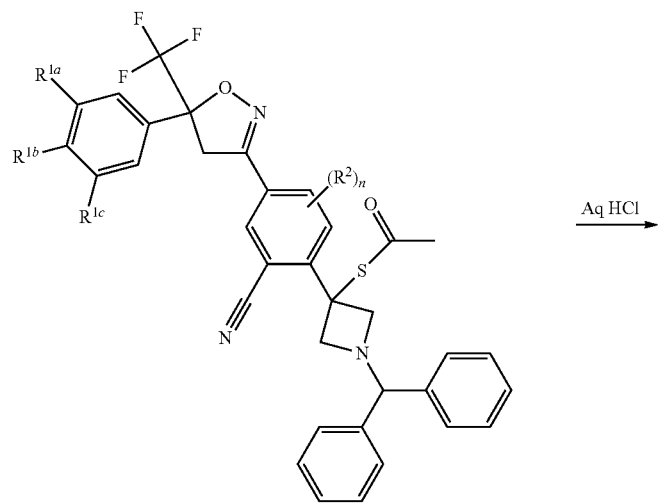
15

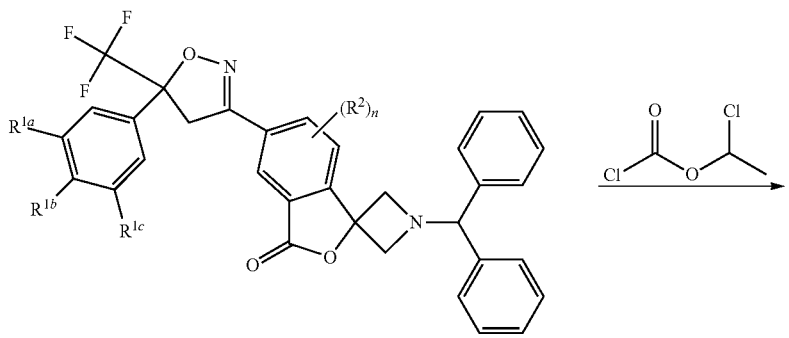

16

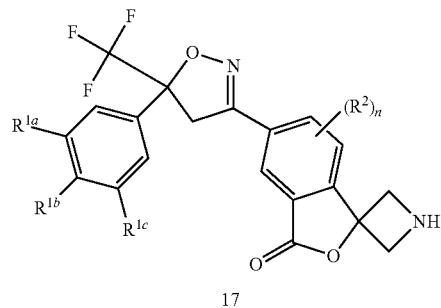

17

$R^{1a}$, $R^{1b}$, $R^{1c}$, $R^2$, $R^5$, and n are as defined herein.

Intermediate 14 can be prepared by treating 7 with mesyl chloride, followed by subsequent addition of thioacetate (*Tetrahedron*, 1995, 3045-3050). Metal-catalyzed cyanation followed by acidic aqueous removal of the acetate group will result in an intramolecular cyclization to afford intermediate 16. Removal of the benzhydryl protecting group with chloroethylchloroformate provides the azetidine 17.

Scheme 5

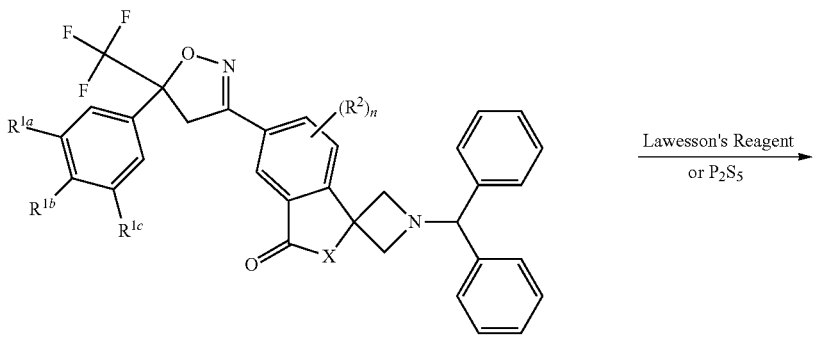

8, 13, or 16

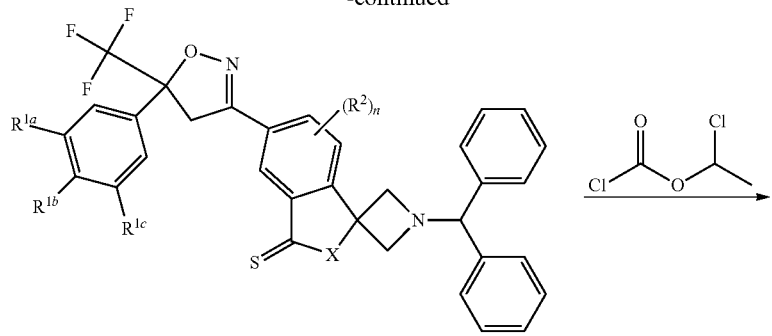
$R^{1a}$, $R^{1b}$, $R^{1c}$, $R^2$, X, and n are as defined herein.
Intermediate derivatives of 8, 13, or 16 can be converted to thiocarbonyl analogs using an electrophilic thionating agent such as Lawesson's reagent or $P_2S_5$ providing intermediates 19. Removal of the benzhydryl protecting group with chloroethylchloroformate provides the azetidine 20.
Scheme 6
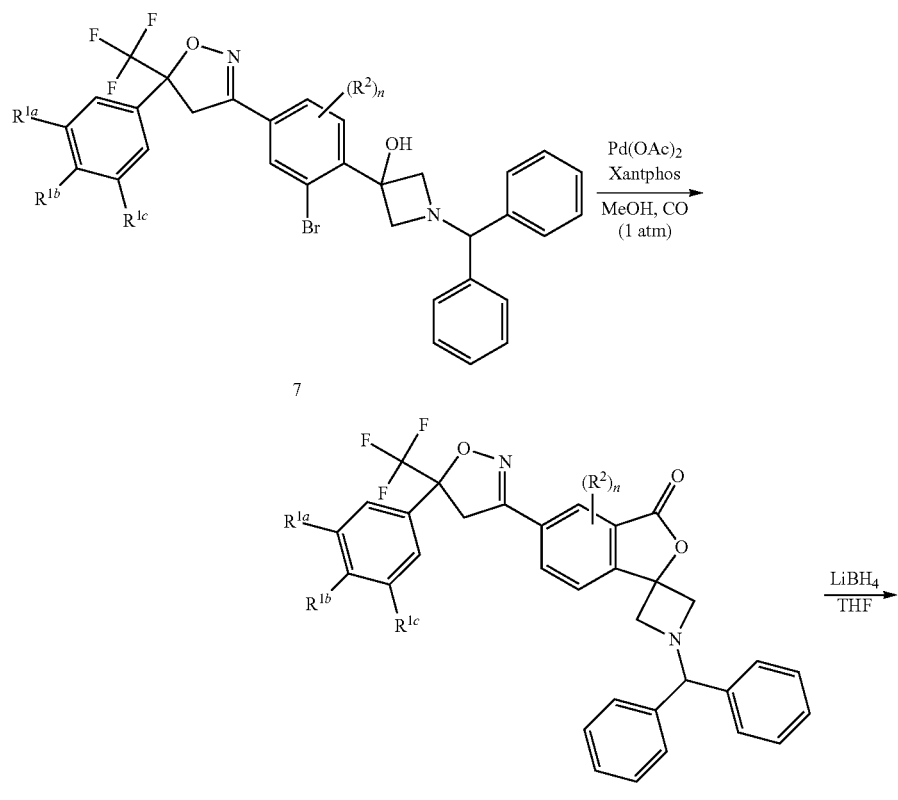

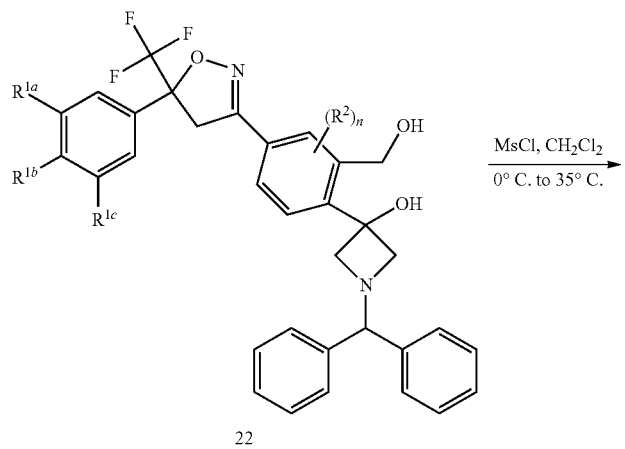

22

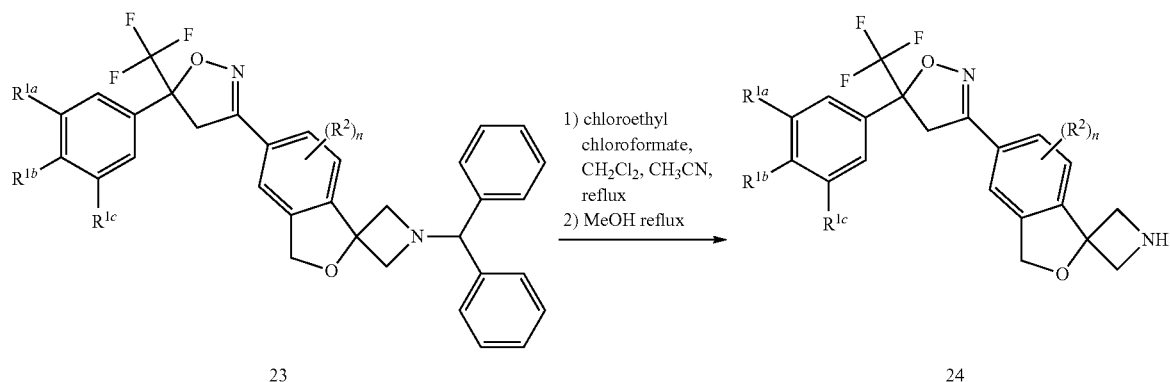

23 → 24

R$^{1a}$, R$^{1b}$, R$^{1c}$, R$^2$, and n are as defined herein.

Phenylazetidine 7 can undergo a metal-catalyzed intramolecular cyclization in the presence of carbon monoxide to afford lactone 21. Reduction of 21 using a reducing agent such as LiBH$_4$ provides bis-alcohol 22. Subsequent mesylation using methanesulfonyl chloride followed by displacement of the leaving group gives ether 23. Additionally, nitrogen or sulfur analogs of ether 23 can be made in a similar manner employing an amine derivative or thioacetate. Removal of the benzhydryl protecting group with chloroethyl-chloroformate provides the azetidine 24.

Scheme 7

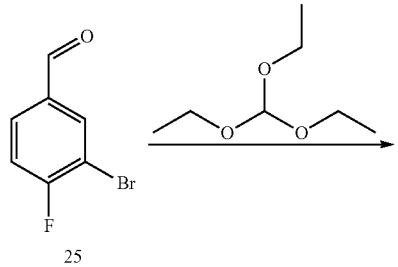

25

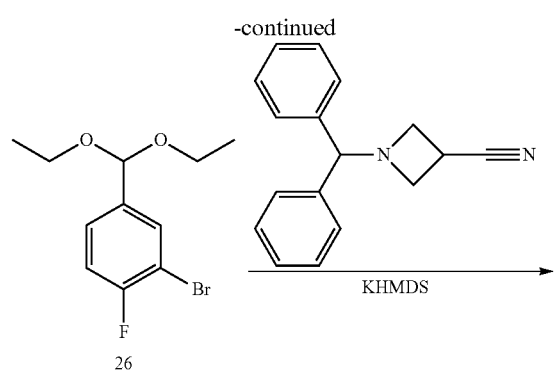

26

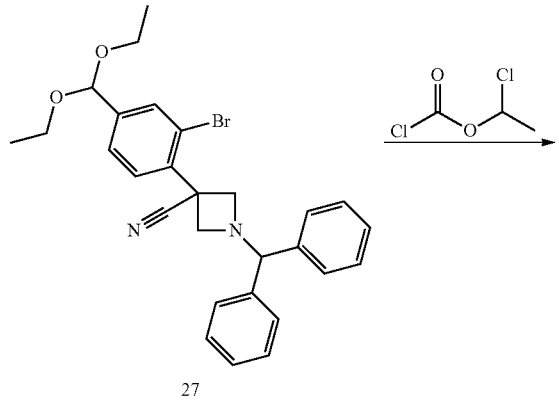

27

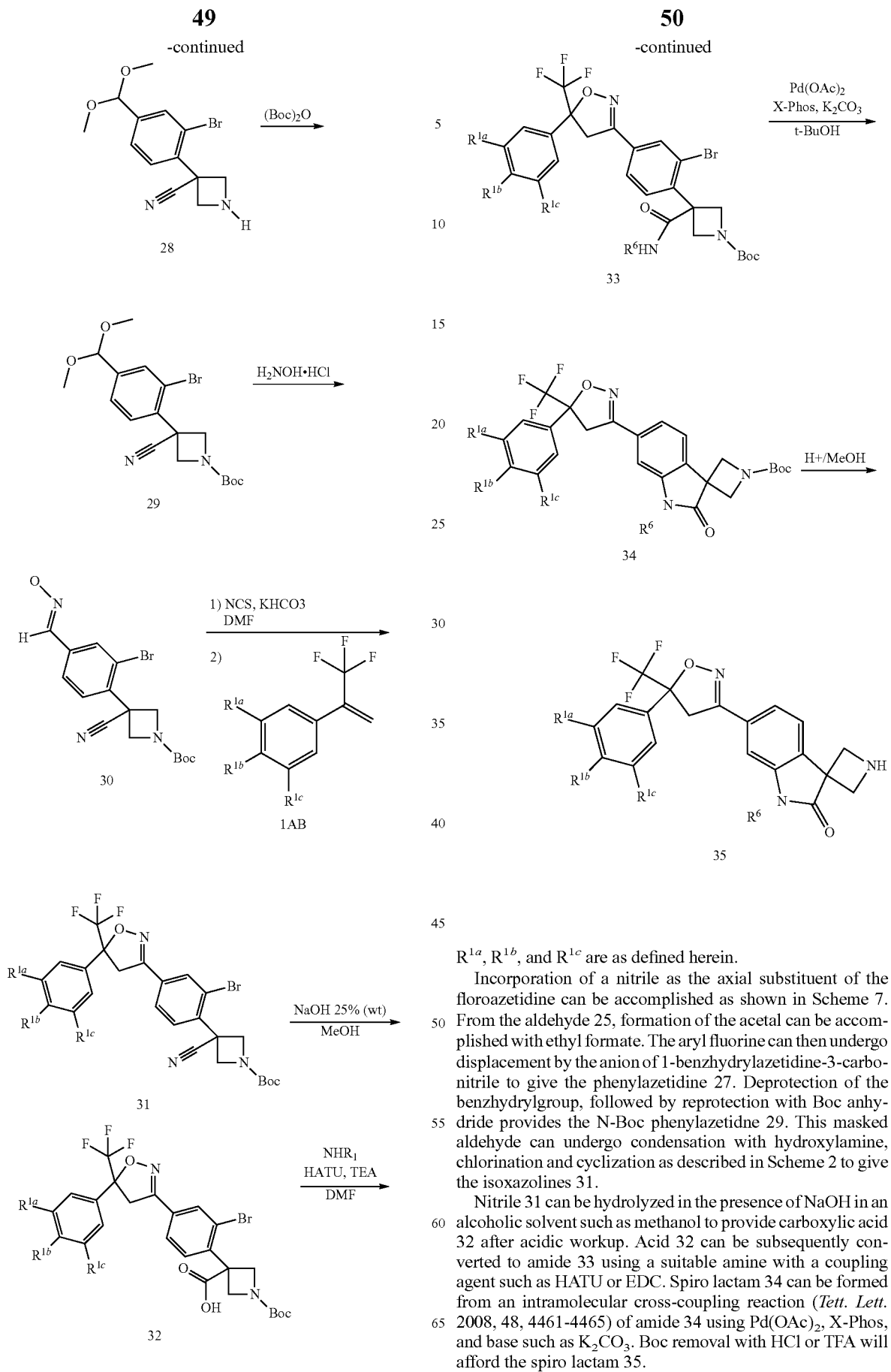

$R^{1a}$, $R^{1b}$, and $R^{1c}$ are as defined herein.

Incorporation of a nitrile as the axial substituent of the floroazetidine can be accomplished as shown in Scheme 7. From the aldehyde 25, formation of the acetal can be accomplished with ethyl formate. The aryl fluorine can then undergo displacement by the anion of 1-benzhydrylazetidine-3-carbonitrile to give the phenylazetidine 27. Deprotection of the benzhydrylgroup, followed by reprotection with Boc anhydride provides the N-Boc phenylazetidne 29. This masked aldehyde can undergo condensation with hydroxylamine, chlorination and cyclization as described in Scheme 2 to give the isoxazolines 31.

Nitrile 31 can be hydrolyzed in the presence of NaOH in an alcoholic solvent such as methanol to provide carboxylic acid 32 after acidic workup. Acid 32 can be subsequently converted to amide 33 using a suitable amine with a coupling agent such as HATU or EDC. Spiro lactam 34 can be formed from an intramolecular cross-coupling reaction (*Tett. Lett.* 2008, 48, 4461-4465) of amide 34 using Pd(OAc)$_2$, X-Phos, and base such as K$_2$CO$_3$. Boc removal with HCl or TFA will afford the spiro lactam 35.

Scheme 8

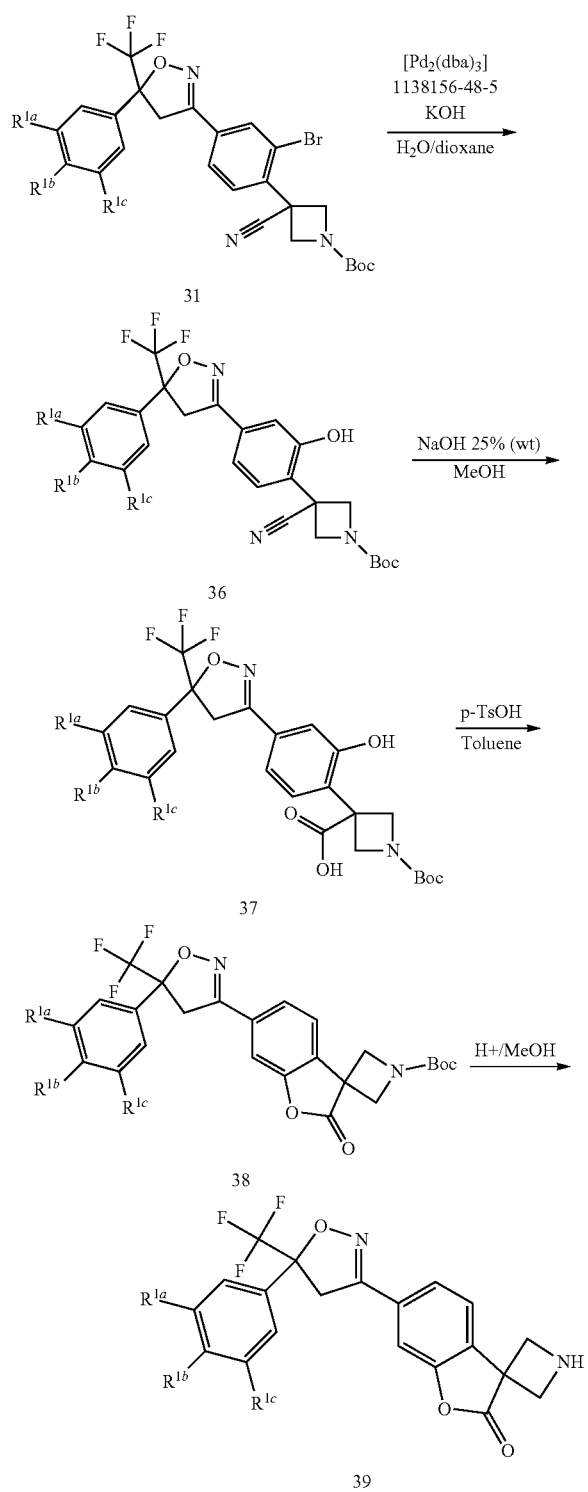

$R^{1a}$, $R^{1b}$, and $R^{1c}$ are as defined herein.

Alternatively, the bromophenyl isoxazoline 31 can be converted to phenol 36 through a cross-coupling reaction (*Angew. Chem. Int. Ed.* 2009, 48, 918-921) using Pd₂(dba)₃, a phosphine ligand, and KOH. 36 can be hydrolyzed in the presence of NaOH in an alcoholic solvent such as methanol to provide carboxylic acid 37 after acidic workup. Catalytic p-TsOH in refluxing toluene will provide spirolactone 38. Boc removal with HCl or TFA will afford the spirocyclic azetidines 39.

Scheme 9

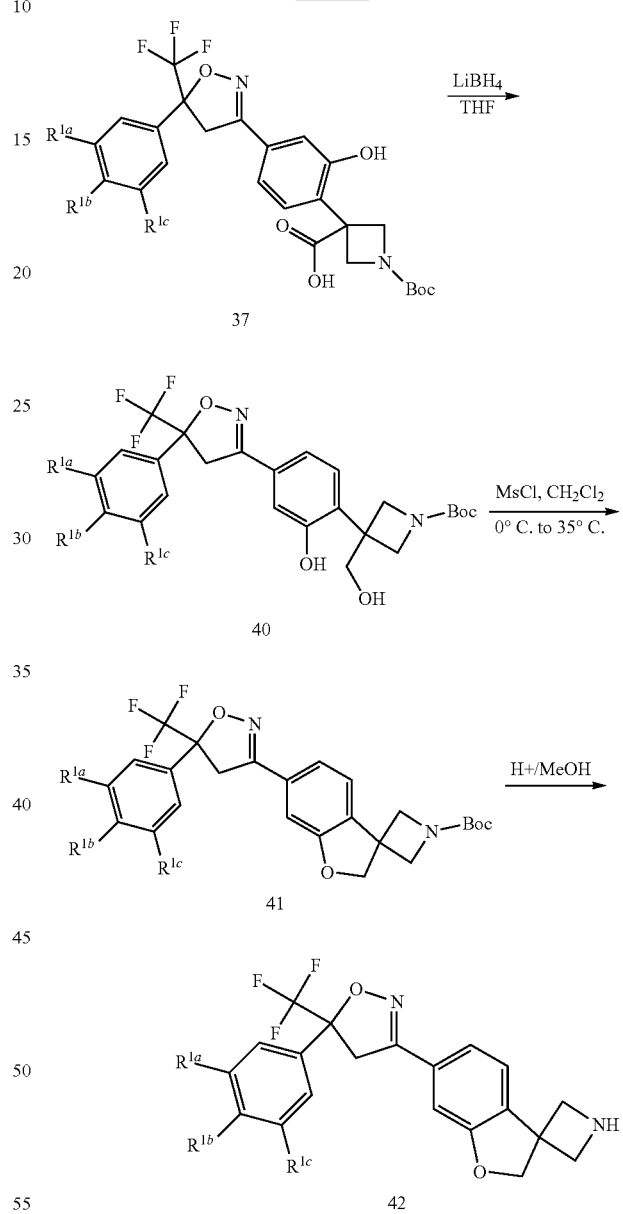

$R^{1a}$, $R^{1b}$, and $R^{1c}$ are as defined herein.

Reduction of the carboxylic acid 37 with lithium borohydride provides the bis-alcohol 40. Subsequent mesylation using methanesulfonyl chloride followed by displacement of this leaving group will give ether 41. Removal of the Boc protecting group with HCl in methanol gives the spirocyclic azetidine 42.

Scheme 10

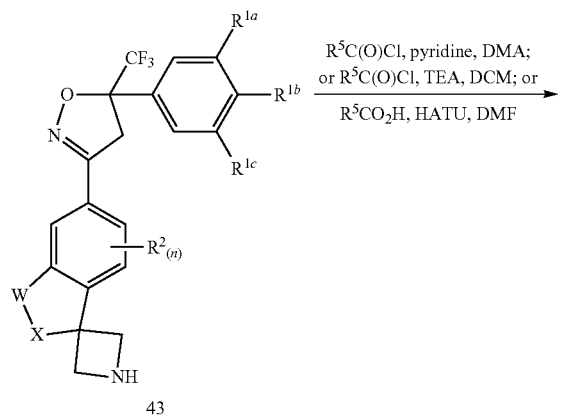

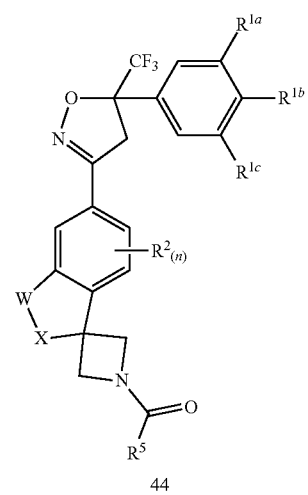

R$^{1a}$, R$^{1b}$, R$^{1c}$, R$^2$, R$^5$, X, W, and n are as defined herein.

Amide analogs of the azetidine ring can be prepared as shown in Scheme 10. Acylation of the azetidine ring can be accomplished by reaction of the azetidine 43 with an acid chloride in pyridine/DMA or by a condensation with a carboxylic acid utilizing a condensing agent such as HATU or HOBt to afford the substituted azetidine 44.

Scheme 11

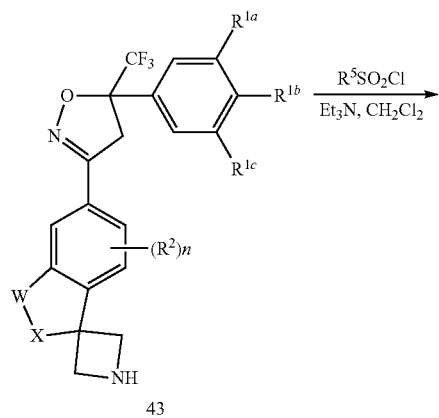

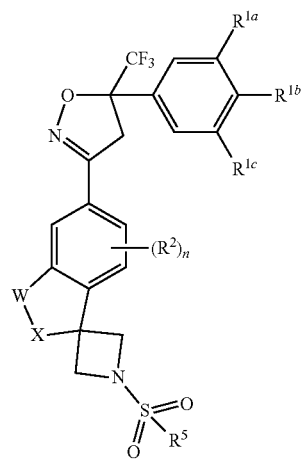

R$^{1a}$, R$^{1b}$, R$^{1c}$, R$^2$, R$^5$, X, W, and n are as defined herein.

Sulfonamide analogs of the azetidine ring can be prepared as shown in Scheme 11. Reaction of azetidine 43 with sulfonyl chlorides in the presence of triethylamine can give the desired sulfonamide substituted azetidines 45.

Scheme 12

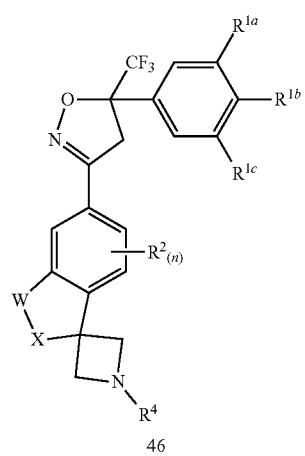

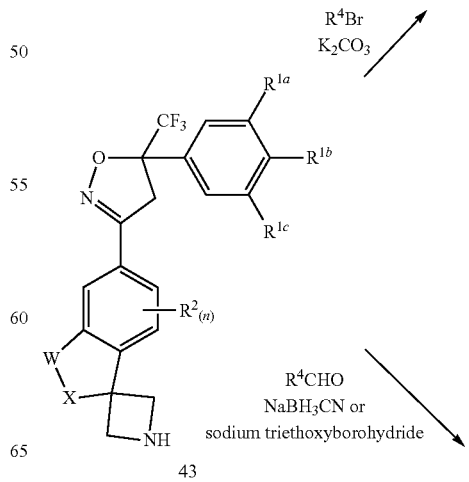

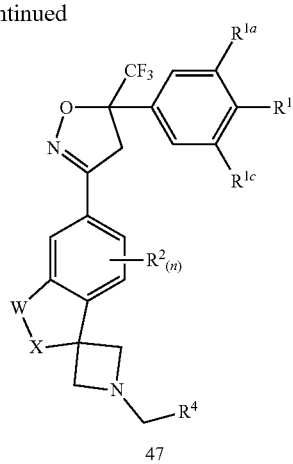

47

$R^{1a}$, $R^{1b}$, $R^{1c}$, $R^2$, $R^4$, X, W, and n are as defined herein.

Compounds in which $R^4$ is alkyl or substituted alkyl can be prepared from the azetidine 43 by standard alkylation chemistry or by reductive amination with the corresponding aldehydes as shown in Scheme 12 to prepare the alkyl substituted azetidines 46 and 47.

Scheme 13

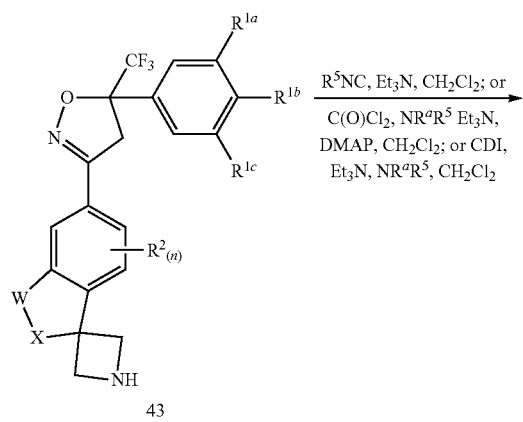

43

48

$R^{1a}$, $R^{1b}$, $R^{1c}$, $R^2$, $R^3$, $R^4$, $R^5$, X, W, and n are as defined herein.

Urea analogs can be prepared as shown in Scheme 13. Reaction of the azetidine 43 with an isocyanate or preformed carbamoyl chloride in the presence of a tertiary amine base provides the ureas 48.

Scheme 14

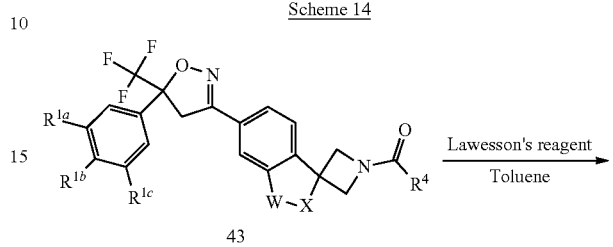

43

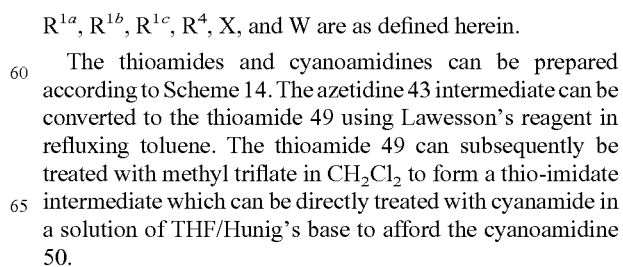

49

50

$R^{1a}$, $R^{1b}$, $R^{1c}$, $R^4$, X, and W are as defined herein.

The thioamides and cyanoamidines can be prepared according to Scheme 14. The azetidine 43 intermediate can be converted to the thioamide 49 using Lawesson's reagent in refluxing toluene. The thioamide 49 can subsequently be treated with methyl triflate in $CH_2Cl_2$ to form a thio-imidate intermediate which can be directly treated with cyanamide in a solution of THF/Hunig's base to afford the cyanoamidine 50.

Scheme 15

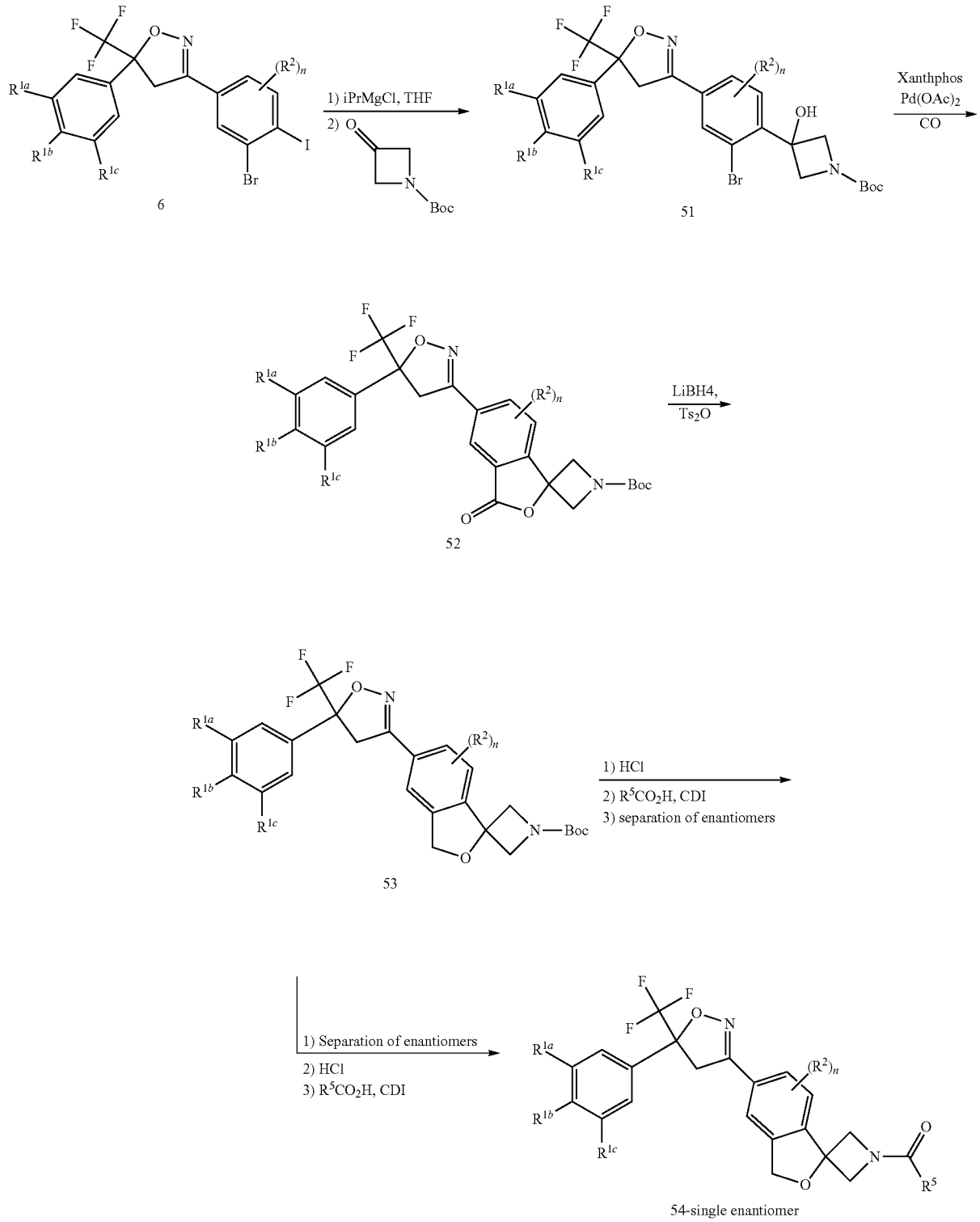

$R^{1a}$, $R^{1b}$, $R^{1c}$, $R^2$, $R^5$, and n are as defined herein.

The single enantiomers of the compounds described herein can be obtained from chiral supercritical fluid chromatography (SFC) separation. Chiral SFC separation of intermediate 53 provides a chiral intermediate which may be carried on to the single enantiomer of the described spiroazetidines. Alternatively, chiral separation may be performed on the final racemic product to provide both enantiomers of 54 as discreet products. Conditions for the chiral separation can be found in the examples section.

Scheme 16-Chiral synthesis

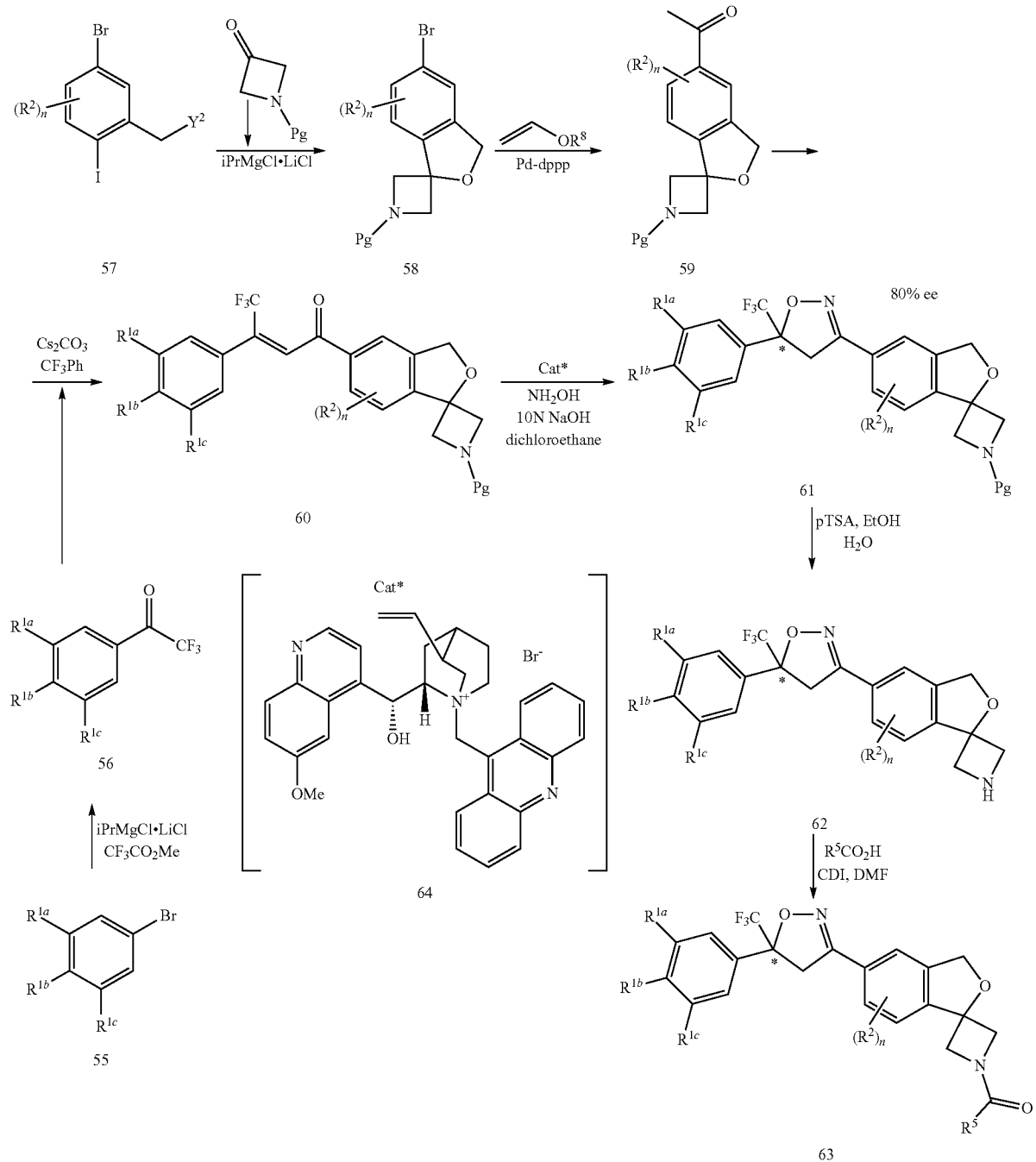

$R^{1a}$, $R^{1b}$, $R^{1c}$, $R^2$, $R^5$, and n are as defined herein. The $R^8$ substituent depicts a $C_1$-$C_6$alkyl moiety (e.g., methyl, ethyl, propyl, isopropyl, butyl, and the like). Pg is a protecting group, for example Boc, diphenylmethane, or a benzylcarbamate and $Y^2$ can be bromine, chlorine, iodine, hydroxyl, or a sulfonate leaving group. The asterisk (*) depicts a chiral center, (i.e., R or S stereochemistry).

A chiral synthesis of the compounds described within can be achieved according to Scheme 16. From the iodobromobenzyl derivative 57, Grignard formation and condensation with tert-butyl 3-oxoazetidine-1-carboxylate provides the cyclized tert-butyl 5'-bromo-3'H-spiro[azetidine-3,1'-isobenzofuran]-1-carboxylate in a one-pot reaction or a stepwise fashion. Palladium catalyzed condensation with a vinyl ether provides the acetophenone 59 which can undergo condensation with the trifluoroacetophenone 56 to give the chalcone 60. Addition of hydroxylamine and cyclization in the presence of a chiral catalyst such as 64 provides the desired enantiomer of the isoxazoline 61 with an 80% ee. Removal of the Boc protecting group can be achieved under acidic conditions such as para-toluenesulfonic acid in an ethanol/water mixture to provide the chiral azetidine 62 which can undergo couplings as previously described to provide the chiral amides 63.
Scheme 17-Synthesis of heterocyclic analogs
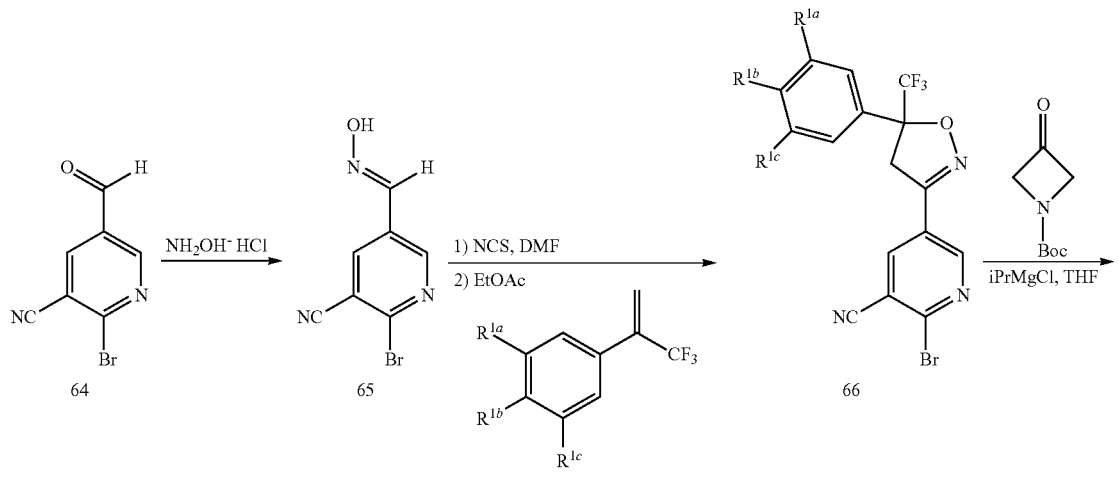
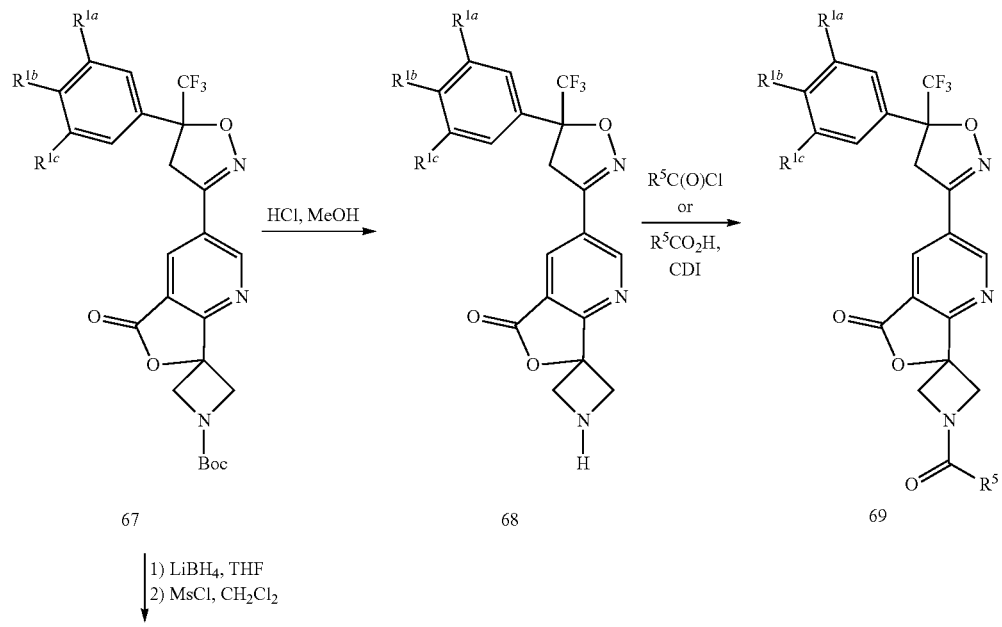

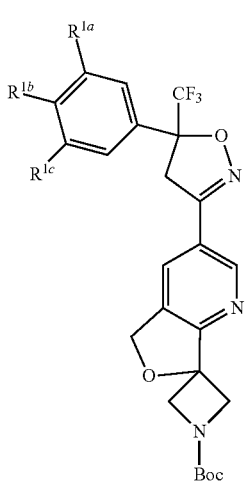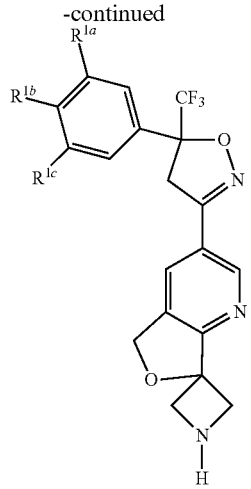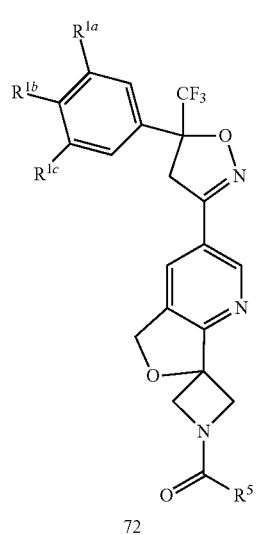

Heterocyclic analogs can be prepared according to Scheme 17. Commercially available aldehyde 64 can undergo condensation with hydroxylamine, chlorination and cyclization to give the bromo-isoxazoline 66. Grignard formation can be achieved using i-PrMgCl and the resulting organometallic adds to the N-protected azetidinone. Upon aqueous work-up, an intramolecular cyclization and hydrolysis will occur to give spiro-lactone 67. Deprotection of 67 with HCl in methanol followed by acid coupling with CDI or acid chloride addition will give final compounds 69. Alternatively, reduction of 67 using a reducing agent such as LiBH$_4$ and subsequent mesylation using methanesulfonyl chloride followed by displacement of the leaving group will give ether 70. Deprotection of 70 with HCl in methanol followed by acid coupling with CDI or acid chloride addition will give final compounds 72.

One skilled in the art will recognize that, in some cases, after the introduction of a given reagent as it is depicted in the schemes, it may be necessary to perform additional routine synthetic steps not described in detail to complete the synthesis of Formula (1) Formula (V.1), Formula (V.1.1), and Formula (V.2) compounds.

The present invention includes all veterinarily acceptable isotopically-labelled Formula (V.1), Formula (V.2), Formula (V.1.1), and Formula (1) compounds wherein one or more atoms are replaced by atoms having the same atomic number, but an atomic mass or mass number different from the atomic mass or mass number usually found in nature.

Examples of isotopes suitable for inclusion in the compounds of the present invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, and sulphur, such as $^{35}$S.

The skilled person will appreciate that the compounds of the present invention could be made by methods other than those herein described as incorporated herein by reference, by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions).

The Formula (V.1), Formula (V.1.1), Formula (V.2), and Formula (1) compounds are useful as antiparasitic agents, therefore, another embodiment of the present invention is a veterinary composition comprising a therapeutically effective amount of a Formula (V.1), Formula (V.1.1), Formula (V.2), and Formula (I) compound, stereoisomer thereof, and a veterinarily acceptable excipient, diluent or carrier. The compounds of the present invention (including the compositions and processes used therein) may also be used in the manufacture of a medicament for the therapeutic applications described herein.

A typical formulation is prepared by mixing a Formula (V.1), Formula (V.1.1), Formula (V.2), and Formula (1) compound with a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe to be administered to an animal. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or veterinary composition thereof) or aid in the manufacturing of the veterinary product (i.e., medicament).

The formulations can be prepared using conventional dissolution and mixing procedures. Such compositions and methods for their preparation may be found, for example, in 'Remington's Veterinary Sciences', 19th Edition (Mack Publishing Company, 1995; and "Veterinary Dosage Forms: Tablets, Vol. 1", by H. Lieberman and L. Lachman, Marcel Dekker, N.Y., 1980 (ISBN 0-8247-6918-X). For example, the bulk drug substance (i.e., compound of the present invention or stabilized form of the compound (e.g., complex with a cyclodextrin derivative or other known complexation agent)) is dissolved in a suitable solvent in the presence of one or more other excipients. The compounds of the present invention are typically formulated into veterinary dosage forms to provide an easily controllable dosage form for administration.

The compounds may be administered alone or in a formulation appropriate to the specific use envisaged, the particular species of host animal being treated and the parasite involved. Generally, they will be administered as a formulation in association with one or more veterinarily acceptable excipients, diluents, or carriers. The term "excipient", "diluent" or "carrier" is used herein to describe any ingredient other than the Formula (V.1), Formula (V.1.1), Formula (V.2), or Formula (1) compounds or any additional antiparasitic agent. The choice of excipient, diluent, or carrier will to a large extent depend on factors such as the particular mode of administration, the effect of the excipient, carrier, or diluent on solubility and stability, and the nature of the dosage form.

The methods by which the compounds of the present invention may be administered include oral, topical, and subcutaneous administration. The preferred method of administration of the Formula (V.1), Formula (V.1.1), Formula (V.2), and Formula (1) compounds is in an oral solid dosage form or oral liquid dosage form.

The Formula (V.1), Formula (V.1.1), Formula (V.2), and Formula (1) compounds can be administered orally by capsule, bolus, tablet, powders, lozenges, chews, multi and nanoparticulates, gels, solid solution, films, sprays, or liquid form. This is a preferred method of administration and as such it is desirable to develop active Formula (V.1), Formula (V.1.1), Formula (V.2), and Formula (1) compounds that are particularly suited to such formulations. Such formulations may be employed as fillers in soft or hard capsules and typically comprise a carrier, for example, water, ethanol, polyethylene glycol, N-methylpyrrolidone, propylene glycol, methylcellulose, or a suitable oil, and one or more emulsifying agents and/or suspending agents. Liquid forms include suspensions, solutions, syrups, drenches and elixirs. Liquid formulations may also be prepared by the reconstitution of a solid, for example, from a sachet. Oral drenches are commonly prepared by dissolving or suspending the active ingredient in a suitable medium. Oral formulations can comprise from about 0.5 mg/kg to 50 mg/kg of a Formula (V.1), Formula (V.1.1), Formula (V.2), and Formula (1) compound, and preferably about 1 mg/kg to 30 mg/kg of a Formula (V.1), Formula (V.1.1), Formula (V.2), and Formula (1) compound.

The compounds may be administered topically to the skin or mucosa, that is dermally or transdermally. This is a preferred method of administration and as such it is desirable to develop active Formula (V.1), Formula (V.1.1), Formula (V.2), and Formula (1) compounds that are particularly suited to such formulations, for example liquid forms. Typical formulations for this purpose include pour-on, spot-on, multi-spot-on, stripe-on, comb-on, roll-on, dip, spray, mousse, shampoo, powder formulation, gels, hydrogels, lotions, solutions, creams, ointments, dusting powders, dressings, foams, films, skin patches, wafers, implants, sponges, fibers, bandages and micro emulsions. Liposomes may also be used. Typical carriers include alcohol, water, mineral oil, liquid petrolatum, white petrolatum, glycerin, N-methyl formamide, glycol monomethyl ethers, polyethylene glycol, propylene glycol, and the like. Penetration enhancers may be incorporated—see, for example, J Pharm Sci, 88 (10), 955-958 by Finnin and Morgan (October 1999). Pour-on or spot-on formulations may be prepared by dissolving the active ingredients in an acceptable liquid carrier vehicle such as butyl digol, liquid paraffin or a non-volatile ester, optionally with the addition of a volatile component such as propan-2-ol or a glycol ether. Alternatively, pour-on, spot-on or spray formulations can be prepared by encapsulation, to leave a residue of active agent on the surface of the animal, this effect may ensure that the Formula (V.1), Formula (V.1.1), Formula (V.2), and Formula (1) compounds have increased persistence of action and are more durable, for example they may be more water fast. Topical formulations of the combination contemplated herein can comprise from about 0.5 mg/kg to 50 mg/kg of a Formula (V.1), Formula (V.1.1), Formula (V.2), and Formula (1) compound, and preferably about 1 mg/kg to 10 mg/kg of a Formula (V.1), Formula (V.1.1), Formula (V.2), and Formula (1) compound.

The compounds of the present invention can also be administered topically via a support matrix for example, a synthetic or natural resin, plastic, cloth, leather, or other such polymeric system in the shape of a collar or ear tag. Said collar or ear tag may be coated, impregnated, layered, by any means so as to provide a veterinarily acceptable amount of a compound of the present invention alone, or with a veterinarily acceptable excipient, diluent, or carrier, and optionally an additional veterinary agent, or veterinarily acceptable salt thereof.

The compositions suitable for spot-on application according to the invention can be prepared by conventional mixing means. The volume of the applied composition can be from about 0.5 mL/kg to 5 mL/kg and preferably from about 1 mL/kg to 3 mL/kg.

Agents may be added to the formulations of the present invention to improve the persistence of such formulations on the surface of the animal to which they are applied, for example to improve their persistence on the coat of the animal. It is particularly preferred to include such agents in a formulation which is to be applied as a pour-on or spot-on formulation. Examples of such agents include acrylic copolymers and in particular fluorinated acrylic copolymers. A particular suitable reagent is the trademark reagent "Foraperle" (Redline Products Inc, Texas, USA).

Certain topical formulations may include unpalatable additives to minimize oral exposure.

Subcutaneous injectable formulations may be prepared in the form of a sterile solution, which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending compounds of the instant invention alone or with an additional veterinary agent in the liquid carrier such that the final formulation contains from about 0.01 to 10% by weight of the active ingredients.

Suitable devices for subcutaneous administration include needle (including micro needle) injectors, needle-free injectors and infusion techniques. Subcutaneous formulations are typically aqueous solutions which may contain excipients such as salts, carbohydrates and buffering agents (preferably to a pH of from 3 to 9), but, for some applications, they may be more suitably formulated as a sterile non-aqueous solution or as a dry powder form to be used in conjunction with a suitable vehicle such as sterile, pyrogen-free water. The preparation of subcutaneous formulations under sterile conditions, for example, by lyophilisation, may readily be accomplished using standard veterinary techniques well known to those skilled in the art. The solubility of compounds of Formula (V.1), Formula (V.1.1), Formula (V.2), and Formula (1) used in the preparation of subcutaneous solutions may be increased by the use of appropriate formulation techniques, such as the incorporation of solubility-enhancing agents.

Such formulations are prepared in a conventional manner in accordance with standard medicinal or veterinary practice. Further, these formulations will vary with regard to the weight of active compound contained therein, depending on the species of host animal to be treated, the severity and type of infection or infestation, and the body weight of the animal.

As described herein, compounds of the present invention may be administered alone or in combination with at least one additional veterinary agent including insecticides, acaricides, anthelmintics, fungicides, nematocides, antiprotozoals, bactericides, and growth regulators to form a multi-component agent giving an even broader spectrum of veterinary utility. Thus, the present invention also pertains to a composition comprising an effective amount of a Formula (V.1), Formula (V.1.1), Formula (V.2), or Formula (1) compound, a stereoisomer thereof, and an effective amount of at least one additional veterinary agent and can further comprise one or more of a veterinarily acceptable excipient, diluent, or carrier.

The following list of additional veterinary agents together with which the compounds of the present invention can be used is intended to illustrate the possible combinations, but not to impose any limitation. Non-limiting examples of additional veterinary agents include: amitraz, arylpyrazoles as recited in publications WO1998/24767 and WO2005/060749, amino acetonitriles, anthelmintics (e.g., albendazole, cambendazole, fenbendazole, flubendazole, mebendazole, octadepsipeptides, oxfendazole, oxibendazole, paraherquamide, parbendazole, piperazines, praziquantel, thiabendazole, tetramisole, triclabendazole, levamisole, pyrantel pamoate, oxantel, morantel, and the like), avermectins (e.g., abamectin, doramectin, emamectin, eprinomectin, ivermectin, moxidectin, selamectin, and the like), milbemycin, milbemycin oxime, DEET, demiditraz, diethylcarbamazine, fipronil, insect growth regulators (e.g., hydroprene, kinoprene, methoprene, and the like), metaflumizone, niclosamide, permethrin, pyrethrins, pyriproxyfen, spinosad, and the like. In certain instances, combinations of a Formula (V.1), Formula (V.1.1), Formula (V.2), and Formula (1) compound with an additional veterinary agent(s) can result in a greater-than-additive effect. Reducing the quantity of active ingredients released in the environment while ensuring effective pest control is always desirable.

It may be desirable to administer a compound of the present invention, stereoisomers thereof, alone or in a composition comprising a veterinarily acceptable excipient, diluent, or carrier, for example, for the purpose of treating a particular parasitic infection or infestation or condition associated therewith. It is within the scope of the present invention that two or more veterinary compositions, at least one of which contains a Formula (V.1), Formula (V.1.1), Formula (V.2), and Formula (1) compound in accordance with the invention, and the other, an additional veterinary agent, may conveniently be combined in the form of a kit suitable for coadministration of the compositions.

The compounds of the present invention (including the compositions and processes used therein) may also be used in the manufacture of a medicament for the therapeutic applications described herein.

The compounds of the present invention, stereoisomers thereof, and compositions comprising a therapeutically effective amount of a Formula (V.1), Formula (V.1.1), Formula (V.2), and Formula (1) compound and a veterinarily acceptable excipient, diluent, or carrier are useful as ectoparasiticides for the control and treatment of infections or infestations manifested by said ectoparasite in an animal. The compounds of the present invention have utility as an ectoparasiticide, in particular, as an acaricide and insecticide. They may, in particular, be used in the fields of veterinary medicine, livestock husbandry and the maintenance of public health: against acarids, insects, and copepods which are parasitic upon vertebrates, particularly warm-blooded vertebrates, including companion animals, livestock, and fowl and cold-blooded vertebrates like fish. Some non-limiting examples of acaride, insect, and copepod parasites include: ticks (e.g., *Ixodes* spp., *Rhipicephalus* spp., *Boophilus* spp., *Amblyomma* spp., *Hyalomma* spp., *Haemaphysalis* spp., *Dermacentor* spp., *Ornithodorus* spp., and the like); mites (e.g., *Dermanyssus* spp., *Sarcoptes* spp., *Psoroptes* spp., *Chorioptes* spp., *Demodex* spp., and the like); chewing and sucking lice (e.g., *Damalinia* spp., *Linognathus* spp., and the like); copepods (e.g., sea lice within the Order Siphonostomatoida, including genera *Lepeophtheirus* and *Caligus*); fleas (e.g., *Siphonaptera* spp., *Ctenocephalides* spp., and the like); biting flies and midges (e.g., *Tabanidae* spp., *Haematobia* spp., *Stomoxys* spp., *Dermatobia* spp., *Simuliidae* spp., *Ceratopogonidae* spp., *Psychodidae* spp., and the like); and bed bugs (e.g., insects within the genus *Cimex* and family Cimicidae).

The compounds of the invention can also be used for the treatment of endoparasites, for example, heartworms, roundworms, hookworms, whipworms, and tapeworms.

The compounds of the present invention and compositions comprising compounds of the present invention in conjunction with at least one other veterinary agent are of particular value in the control of ectoparasites, endoparasites, and insects which are injurious to, or spread or act as vectors of diseases in companion animals, livestock, birds, and fish. The ectoparasites, insects, and endoparasites which can be treated with a combination of a Formula (V.1), Formula (V.1.1), Formula (V.2), and Formula (1) compound and an additional veterinary agent include those as herein before described and including helminthes of the phylum platyhelminthes (e.g., trematodes, eucestoda, and cestoda), and nemathelminthes (e.g., nematodes).

Any of the compounds of the present invention, or a suitable combination of a compound of the present invention and optionally, with at least one additional veterinary agent may be administered directly to the animal and/or indirectly by applying it to the local environment in which the animal dwells (such as bedding, enclosures, and the like). Direct administration includes contacting the skin, fur, or feathers of a subject animal with the compound(s), or by feeding or injecting the compounds into the animal.

The Formula (V.1), Formula (V.1.1), Formula (V.2), and Formula (1) compounds, stereoisomers thereof, and combinations with at least one additional veterinary agent, as described herein, are of value for the treatment and control of the various lifecycle stages of insects and parasites including egg, nymph, larvae, juvenile and adult stages.

The present invention also relates to a method of administering a compound of the present invention alone or in combination with at least one additional veterinary agent, and optionally a veterinarily acceptable excipient, diluent, or carrier, to animals in good health comprising the application to said animal to reduce or eliminate the potential for human parasitic infection or infestation from parasites carried by the animal and to improve the environment in which the animals inhabit.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed using glass-backed silica gel 60 F 254 precoated plates and eluted with appropriate solvent ratios (v/v). Reactions were assayed by TLC or LCMS and terminated as judged by the consumption of starting material. Visualization of the TLC plates was done with UV light (254 nM wavelength) or with an appropriate TLC visualizing solvent and activated with heat. Flash column chromatography (Still et al., *J. Org. Chem.* 43, 2923, (1978) was performed using silica gel (RediSep Rf) or various MPLC systems, such as Biotage or ISCO purification system.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography (TLC), recrystallization, and differential (i.e., liquid-liquid) extraction techniques.

The compound structures in the examples below were confirmed by one or more of the following methods: proton magnetic resonance spectroscopy, and mass spectroscopy. Proton magnetic resonance ($^1$H NMR) spectra were determined using a Bruker spectrometer operating at a field strength of 400 megahertz (MHz). Chemical shifts are reported in parts per million (PPM, δ) downfield from an internal tetramethylsilane standard. Mass spectra (MS) data were obtained using Agilent mass spectrometer with atmospheric pressure chemical ionization. Method: Acquity HPLC with chromatography performed on a Waters BEH C18 column (2.1×50 mm, 1.7 μm) at 50° C. The mobile phase was a binary gradient of acetonitrile (containing 0.1% trifluoroacetic acid) and water (5-100%).

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

The following examples provide a more detailed description of the process conditions for preparing compounds of the present invention. It is to be understood, however, that the invention, as fully described herein and as recited in the claims, is not intended to be limited by the details of the following schemes or modes of preparation.

Preparation 1

Methyl 3-bromo-4-iodobenzoate

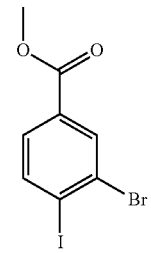

A solution of 4-amino-3-bromo-benzoic acid methyl ester (5.0 g, 22.0 mmol from Aldrich) in acetone (35 mL) was treated with 6M HCl (35 mL). The solution was cooled to 0° C. and treated dropwise with NaNO$_2$ (1.84 g, 26.1 mmol) dissolved in 10 mL water. After stirring for 2 hours at 0° C., the reaction was slowly treated with potassium iodide (5.47 g, 32.6 mmol) dissolved in 20 mL water. The reaction mixture was allowed to warm to room temperature and stir for 1 hour. Reaction mixture was diluted with water and extracted with EtOAc (2×150 mL). The combined organic phase was dried (Na$_2$SO$_4$) and concentrated under vacuum. The residue was chromatographed (80 g Redi-Sep column) eluting from 100% heptane to 20:80 EtOAc:heptane to afford the intermediate (4.1 g, 55%) as a solid. $^1$HNMR (CDCl$_3$) δ ppm: 8.27 (1H), 7.98 (1H), 7.64 (1H), 3.94 (3H).

Preparation 2

(3-bromo-4-iodophenyl)methanol

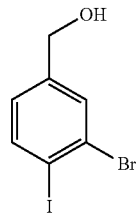

A solution of methyl 3-bromo-4-iodobenzoate (4.3 g, 12.6 mmol) in CH$_2$Cl$_2$ was cooled, under N$_2$, to −78° C. DIBAL-H (25.2 mL of a 1M solution in CH$_2$Cl$_2$) was added slowly to the solution, which was stirred at −78° C. for 45 minutes and then allowed to come to room temperature. Next, the reaction mixture was diluted with 1M HCL (40 mL) and stirred for 30 minutes. The reaction was further diluted with water and extracted with CH$_2$Cl$_2$. The organic phase was dried (Na$_2$SO$_4$) and concentrated under vacuum to afford the intermediate (3.2 g, 82%) as a solid. $^1$HNMR (CDCl$_3$) δ ppm: 7.85 (1H), 7.67 (1H), 7.02 (1H), 4.65 (2H), 1.76 (1H, OH).

Preparation 3

3-bromo-4-iodobenzaldehyde

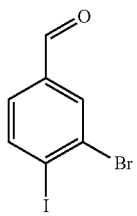

A solution of (3-bromo-4-iodophenyl)methanol (3.1 g, 9.9 mmol) in $CH_2Cl_2$/water (2:1, 225 mL) was treated with $NaHCO_3$ (915 mg, 10.9 mmol), NaBr (1060 mg, 10.2 mmol) and TEMPO free radical (40 mg, 0.2 mmol). The resulting mixture was cooled to 0° C. and NaOCl solution (0.8 mL, 10% aq.) was added dropwise. The reaction mixture was left to come to room temperature while stirring. TLC 25:75 EtOAc:heptane after 30 minutes showed approximately 50% conversion to less polar spot. Sequence repeated using same equivalent of reagents. TLC still showed unreacted starting material. The reaction mixture was separated and the organic phase was treated with 1.0× Dess-Martin periodinane (2.1 g, 4.9 mmol) while stirring. TLC after 10 minutes showed complete conversion to less polar spot. The organic phase was washed with saturated $NaHCO_3$, dried over $Na_2SO_4$, filtered and evaporated to give an orange solid. The crude material was chromatographed (80 g Redi-Sep column) eluting from 100% heptane to 50:50 EtOAc/heptane to give the intermediate (2.7 g, 87%) as a white solid. $^1$HNMR ($CDCl_3$) δ ppm: 9.94 (1H), 8.10 (2H), 7.50 (1H).

Preparation 4

(E/Z)-3-bromo-4-iodobenzaldehyde oxime

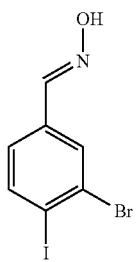 [SMILES: O/N=C/c1ccc(I)c(Br)c1]

To a solution of 3-bromo-4-iodobenzaldehyde (1000 mg, 3.2 mmol) in EtOH (50 mL) was added $NH_2OH$, HCl (345 mg, 4.8 mmol) and water (10 mL). The reaction was heated to 50° C. for 1 hour and then allowed to stir for 18 hours at room temperature. The reaction mixture was concentrated under vacuum to remove EtOH. Water was added to residue and extracted with EtOAc (2×75 mL). The combined organic phase was dried ($Na_2SO_4$) and concentrated under vacuum to afford the intermediate (1035 mg, 98%) as a glass. m/z (CI)=326 $[M+H]^+$.

Preparation 5

3-(3-bromo-4-iodophenyl)-5-(3,4,5-trichlorophenyl)-5-(trifluoromethyl)-4,5-dihydroisoxazole

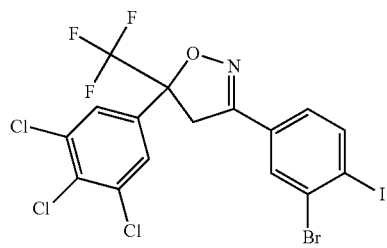 [SMILES: FC(F)(F)C1(c2cc(Cl)c(Cl)c(Cl)c2)CC(c2ccc(I)c(Br)c2)=NO1]

To a DMF (25 mL) solution of (E/Z)-3-bromo-4-iodobenzaldehyde oxime (1000 mg, 3.1 mmol) was added NCS (500 mg, 3.7 mmol) portionwise. The reaction was stirred at room temperature for 18 hours. TLC 50:50 EtOAc:heptane shows slightly less polar spot, no starting material. The reaction mixture was diluted with EtOAc (100 mL) and washed with water (2×50 mL). The organic phase was dried over sodium sulfate and concentrated to give the chlorooxime intermediate (1056 mg, 96%) as a solid. Next, to an ethyl acetate (70 mL) solution of the chlorooxime (1 g, 2.8 mmol) and 1,2,3-trichloro-5-(1,1,1-trifluoroprop-2-en-2-yl)benzene (765 mg, 2.8 mmol) was added potassium bicarbonate (310 mg, 3.1 mmol). The mixture was allowed to stir at room temperature over the weekend. Reaction mixture was filtered and concentrated under vacuum. The residue was chromatographed (80 g Redi-Sep column) eluting from 100% heptane to 20:80 EtOAc:heptane to afford the intermediate (1.53 g, 92%) as a solid. $^1$HNMR ($CDCl_3$) δ ppm: 7.95 (1H), 7.88 (1H), 7.65 (2H), 7.33 (1H), 4.07 (1H), 3.67 (1H).

Preparation 6

1-benzhydryl-3-(2-bromo-4-(5-(3,4,5-trichlorophenyl)-5-(trifluoromethyl)-4,5-dihydroisoxazol-3-yl)phenyl)azetidin-3-ol

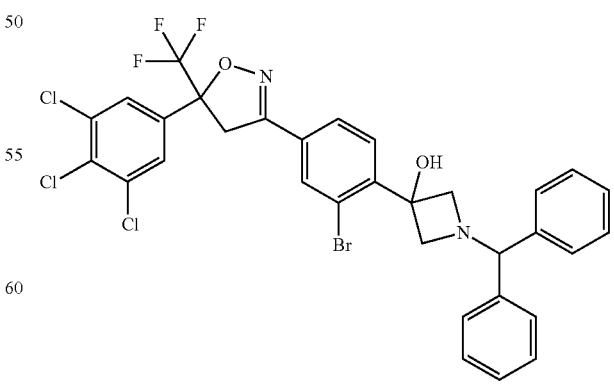

In an oven-dried flask containing 3-(3-bromo-4-iodophenyl)-5-(3,4,5-trichlorophenyl)-5-(trifluoromethyl)-4,5-dihydroisoxazole (1000 mg, 1.67 mmol) in THF (25 mL) at −40° C. was slowly added isopropyl magnesium chloride (1.7 mL of 2.0M solution). The reaction was stirred at approximately −40° C. for 1.5 hours under nitrogen. 1-benzhydrylazetidin-3-one (520 mg in 4 mL THF) was slowly added. The reaction was stirred at −40° C. for an additional 30 minutes and allowed to warm to room temperature. Stirring was continued for 2 hours at room temperature. The reaction was quenched with saturated NH$_4$Cl and extracted with EtOAc (2×75 mL). The combined organic phase was dried (Na$_2$SO$_4$) and concentrated under vacuum. The crude material was chromatographed (40 g Redi-Sep column) eluting from 100% heptane to 60:40 EtOAc:heptane, collecting the intermediate (615 mg, 52%) as a glass. $^1$HNMR (CDCl$_3$) δ ppm: 7.87 (1H), 7.66-7.63 (3H), 7.45 (4H), 7.36-7.21 (7H), 4.39 (1H), 4.07 (1H), 3.73-3.58 (5H), 3.06 (1H); m/z (CI) 711 [M+H]$^+$.

Preparation 7

1-benzhydryl-5'-(5-(3,4,5-trichlorophenyl)-5-(trifluoromethyl)-4,5-dihydroisoxazol-3-yl)-3'H-spiro[azetidine-3,1'-isobenzofuran]-3'-one

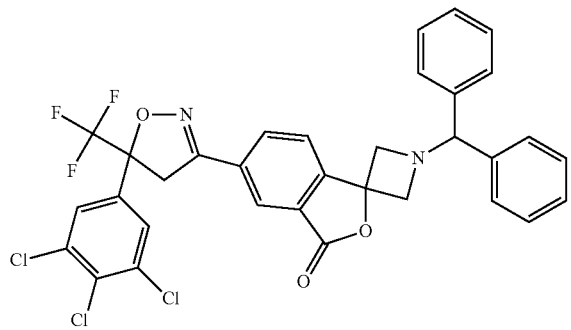 [SMILES: O=C1OC2(CN(C(c3ccccc3)c3ccccc3)C2)c2ccc(C3=NOC(c4cc(Cl)c(Cl)c(Cl)c4)(C(F)(F)F)C3)cc21]

To a solution of 1-benzhydryl-3-(2-bromo-4-(5-(3,4,5-trichlorophenyl)-5-(trifluoromethyl)-4,5-dihydroisoxazol-3-yl)phenyl)azetidin-3-ol (500 mg, 0.7 mmol) in DMF (12 mL) was added Zn(CN)$_2$ (180 mg, 1.5 mmol) and the reaction was degassed with N$_2$ purge. Pd(PPh$_3$)$_4$ (40 mg, 0.04 mmol) was added and the reaction mixture was heated at 150° C. for 15 minutes under microwave irradiation. The reaction mixture was diluted with water, extracted with EtOAc, dried, and concentrated under vacuum. The crude material was chromatographed (40 g Redi-Sep column) eluting from 100% heptane to 50:50 EtOAc:heptane to afford the intermediate (268 mg, 58%) as a glass. $^1$HNMR (CDCl$_3$) δ ppm: 8.32 (1H), 8.18 (1H), 7.95 (1H), 7.68 (2H), 7.51 (4H), 7.35-7.23 (6H), 4.55 (1H), 4.15 (1H), 3.79-3.69 (3H), 3.60 (2H); m/z (CI) 657 ([M+H]$^+$.

Preparation 8

5'-(3,4,5-trichlorophenyl)-5-(trifluoromethyl)-4,5-dihydroisoxazol-3-yl)-3'H-spiro{azetidine-3,1'-isobenzofuran}-3'-one

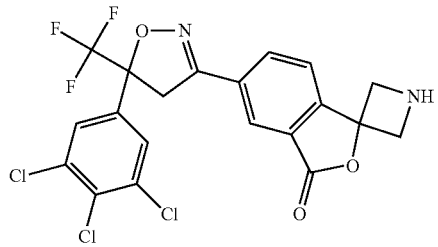 [SMILES: O=C1OC2(CNC2)c2ccc(C3=NOC(c4cc(Cl)c(Cl)c(Cl)c4)(C(F)(F)F)C3)cc21]

To a solution of 1-benzhydryl-5'-(5-(3,4,5-trichlorophenyl)-5-(trifluoromethyl)-4,5-dihydroisoxazol-3-yl)-3'H-spiro[azetidine-3,1'-isobenzofuran]-3'-one (260 mg, 0.39 mmol) in MeCN/CH$_2$Cl$_2$ (5:1, 60 mL) at 0° C. was added 1-chloroethyl chloroformate (150 μL, 1.4 mmol). The reaction was heated to reflux for 2 hours then allowed to cool to room temperature while stirring for 18 hours. Next, the reaction mixture was concentrated under vacuum, re-dissolved in anhydrous MeOH (50 mL), and refluxed for 1 hour. The reaction was cooled, concentrated under reduced pressure, and diethyl ether was added to the residue. The resulting precipitate was filtered, rinsed with diethyl ether, and air dried to afford the intermediate (148 mg, 71%) as a solid. m/z (CI) 491 [M+H]$^+$.

Example 1

1-(cyclopropanecarbonyl)-5'-(3,4,5-trichlorophenyl)-5-(trifluoromethyl)-4,5-dihydroisoxazol-3-yl)-3'H-spiro{azetidine-3,1'-isobenzofuran}-3'-one

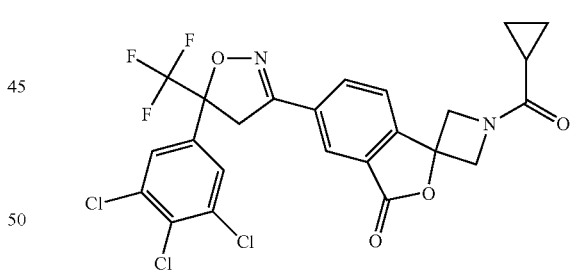

5'-(3,4,5-trichlorophenyl)-5-(trifluoromethyl)-4,5-dihydroisoxazol-3-yl)-3'H-spiro{azetidine-3,1'-isobenzofuran}-3'-one (140 mg, 0.3 mmol) was dissolved in CH$_2$Cl$_2$ (5 mL) at 0° C. and TEA (0.15 mL, 1.1 mmol) was added. The reaction was stirred at room temperature for 5 minutes and cyclopropanecarbonyl chloride (35 mg, 0.3 mmol) was added. The resulting solution was stirred at room temperature for 15 minutes. Next, a few drops of MeOH were added and the reaction was concentrated to ~3 mL under vacuum and injected directly onto a 24 g Redi Sep column. The crude material was chromatographed eluting from 100% heptane to 60:40 EtOAc:heptane to afford the final product (68 mg, 46%) as a solid. $^1$HNMR (CDCl$_3$) δ ppm: 8.29 (1H), 8.04 (1H), 7.85 (1H), 7.67 (2H) 4.94-4.83 (1H), 4.86-4.58 (2H), 4.49-4.37 (1H), 4.16 (1H), 3.78 (1H), 1.50 (1H), 1.11 (2H), 0.90 (2H); m/z (CI) 559 [M+H]⁺.

Example 2

5'-(5-(3,5-dichloro-4-fluorophenyl)-5-(trifluoromethyl)-4,5-dihydroisoxazol-3-yl)-1-propionyl-3'H-spiro[azetidine-3,1'-isobenzofuran]-3'-one

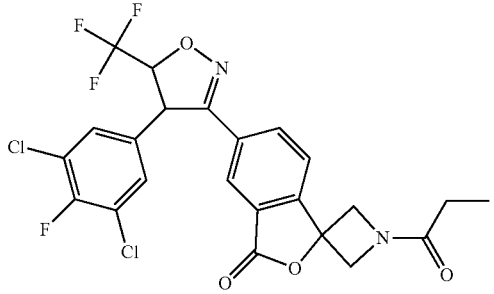 [SMILES: CCC(=O)N1CC2(C1)OC(=O)c1cc(C3=NOC(C(F)(F)F)C3c3cc(Cl)c(F)c(Cl)c3)ccc12]

The compound was prepared similarly to that of Example 1 except that the cyclopropanecarbonyl chloride was replaced with propionyl chloride (10 mg, 0.1 mmol) and the olefin (1AB) was 1,3-dichloro-2-fluoro-5-(1-trifluoromethyl-vinyl)-benzene rather than 1,2,3-trichloro-(1-trifluoromethyl-vinyl)-benzene.

The reaction was injected directly onto a 24 g Redi Sep column. The crude material was chromatographed eluting from 100% heptane to 50:50 EtOAc:heptane to afford the final product (25 mg, 48%) as a solid. m/z (CI) 531 [M+H]⁺.

Preparation 9

1-benzhydryl-3-(2-bromo-4-(5-(3,5-dichlorophenyl-4-fluoro)-5-(trifluoromethyl)-4,5-dihydroisoxazol-3-yl)phenyl)azetidin-3-ol

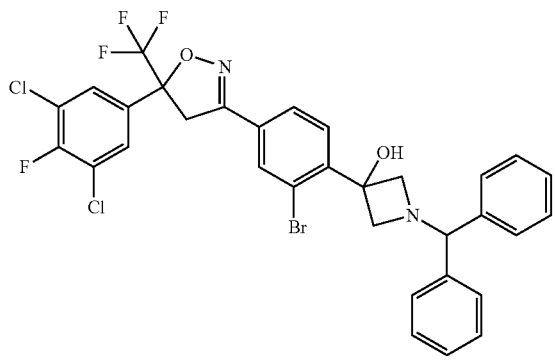 [SMILES: OC1(c2ccc(C3=NOC(c4cc(Cl)c(F)c(Cl)c4)(C(F)(F)F)C3)cc2Br)CN(C(c2ccccc2)c2ccccc2)C1]

This compound was made from the compound of Preparation 4 according to the procedures of Preparations 5 and 6, utilizing 1,3-dichloro-2-fluoro-5-(1,1,1-trifluoroprop-2-en-2-yl)benzene in place of 1,2,3-trichloro-5-(1,1,1-trifluoroprop-2-en-2-yl)benzene. m/z (CI)=695 [M+H]⁺.

Preparation 10

1-benzhydryl-5'-(5-(3,5-dichloropheny-4-fluorol)-5-(trifluoromethyl)-4,5-dihydroisoxazol-3-yl)-3'H-spiro[azetidine-3,1'-isobenzofuran]-3'-one

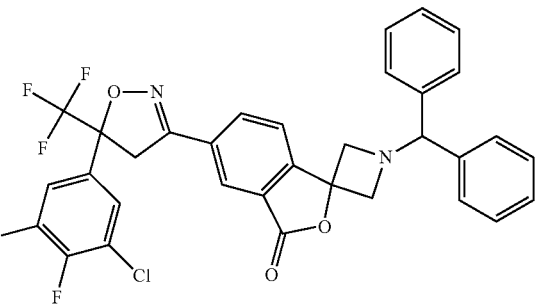

A stream of carbon monoxide gas was bubbled through a solution of 1-benzhydryl-3-(2-bromo-4-(5-(3,5-dichlorophenyl-4-fluoro)-5-(trifluoromethyl)-4,5-dihydroisoxazol-3-yl)phenyl)azetidin-3-ol (Preparation 9, 50 g, 72 mmol) in toluene (100 mL) and triethylamine (100 mL) for 30 seconds. To this was added palladium acetate (260 mg) and Xantphos (680 mg, 1.2 mmol). A balloon containing carbon monoxide was attached to the reaction flask and it was heated to 85° C. for 4 hours. At this point, an additional and identical amount of both palladium acetate and Xantphos were added. The reaction was heated for an additional eight hours at 85° C. The reaction was cooled to ambient temperature and filtered to remove the catalyst. The product was isolated by silica column chromatography: 400 gm of silica, eluting with a gradient of 0% to 10% ethyl acetate in a mixture of 1:1 CH₂Cl₂:hexane. The material was dried under vacuum at 50'C to afford 35 g of a white solid. m/z (CI)=642 [M+H]⁺.

Preparation 11

1-benzhydryl-3-(2-hydroxymethyl-4-(5-(3,4,5-trichlorophenyl)-5-(trifluoromethyl)-4,5-dihydroisoxazol-3-yl)phenyl)azetidin-3-ol

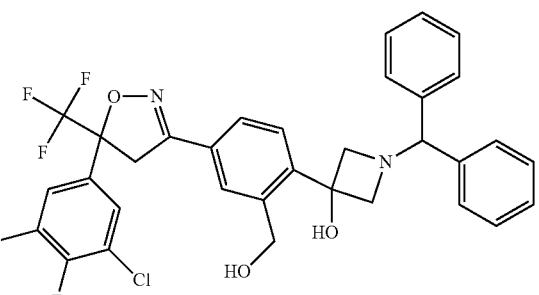

To a solution of 1-benzhydryl-5'-(5-(3,5-dichloropheny-4-fluorol)-5-(trifluoromethyl)-4,5-dihydroisoxazol-3-yl)-3'H-spiro[azetidine-3,1'-isobenzofuran]-3'-one (Preparation 10, 20.0 g, 31 mmol) in THF (200 mL) was added lithium borohydride (1.03 g, 47 mmol) at ambient temperature. The reaction was stirred for 16 hours and was then quenched by slow addition of methanol (20 mL). The solution was concentrated under reduced pressure and the residue was dissolved in EtOAc (200 mL) and then washed with saturated aqueous Na₂CO₃ (2×100 mL). The organics were concentrated and the residue was purified on a silica column: 400 g of silica with gradient eluent of 0% to 30% EtOAc in CH₂Cl₂. The product was dried under vacuum at 50'C to afford 10.0 gm of a white solid. m/z (CI)=646 [M+H]⁺.

Preparation 12

1-benzhydryl-5'-(5-(3,5-dichloropheny-4-fluorol)-5-(trifluoromethyl)-4,5-dihydroisoxazol-3-yl)-3'H-spiro[azetidine-3,1'-isobenzofuran]

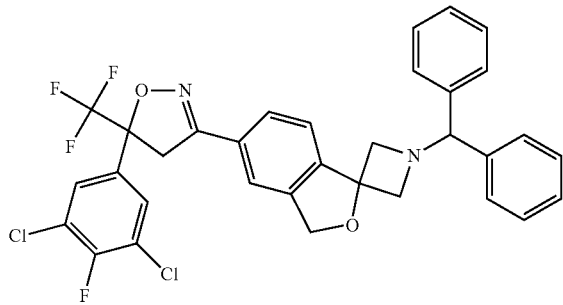 [SMILES: Fc1c(Cl)cc(C2(C(F)(F)F)CC(c3ccc4c(c3)COC43CN(C(c4ccccc4)c4ccccc4)C3)=NO2)cc1Cl]

A solution of 1-benzhydryl-3-(2-hydroxymethyl-4-(5-(3, 4,5-trichlorophenyl)-5-(trifluoromethyl)-4,5-dihydroisoxazol-3-yl)phenyl)azetidin-3-ol (Preparation 11, 9.8 g, 15.2 mmol) in toluene (100 mL) was cooled to 0° C. To this was added triethylamine (5 g) followed by p-toluene sulfonic anhydride (5.7 g, 17.4 mmol). The reaction was allowed to warm to ambient temperature and was stirred for 16 hours. The reaction was washed with saturated aqueous Na₂CO₃ (2×50 mL) and then with water (50 mL). The organic solution was filtered through a plug of silica (10 g) and was concentrated under reduced pressure. m/z (CI)=628 [M+H]⁺.

Preparation 13

5'-(5-(3,5-dichloropheny-4-fluorol)-5-(trifluoromethyl)-4,5-dihydroisoxazol-3-yl)-3'H-spiro[azetidine-3,1'-isobenzofuran]

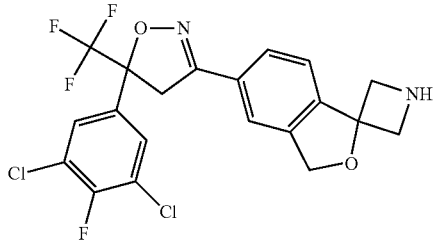 [SMILES: Fc1c(Cl)cc(C2(C(F)(F)F)CC(c3ccc4c(c3)COC43CNC3)=NO2)cc1Cl]

To a solution of 1-benzhydryl-5'-(5-(3,5-dichloropheny-4-fluorol)-5-(trifluoromethyl)-4,5-dihydroisoxazol-3-yl)-3'H-spiro[azetidine-3,1'-isobenzofuran](Preparation 12, 10.0 g, 16 mmol) in MeCN (100 mL) at ambient temperature was added 1-chloroethyl-chloroformate (9.8 g, 68 mmol). The reaction was heated to 75'C for 2 hours. The reaction was cooled to ambient temperature and was concentrated under vacuum. The residue was dissolved in anhydrous methanol (200 mL) and was heated to reflux for 1 hour. The reaction was concentrated under reduced pressure and the residue was purified on a silica column: 200 g of silica, gradient of 0 to 20% EtOH in methylene chloride. ¹HNMR (d₆-DMSO) δ ppm: 8.10 (1H), 7.81 (3H), 7.70 (1H), 5.10 (2H), 4.37 (2H), 4.24 (2H), 4.15 (2H), m/z (CI) 462 [M+H]⁺.

Example 3

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-((trifluoromethypthio)ethanone

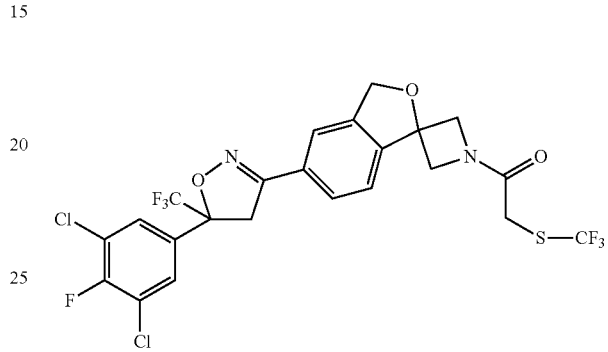

5'-[5-(3,5-dichloro-4-fluorophenyl)-5-(trifluoromethyl)-4,5-dihydro-1,2-oxazol-3-yl]-3'H-spiro[azetidine-3,1'-[2] benzofuran] (0.05 mmol) was dissolved in DMF (0.5 ml); this was added to [(trifluoromethyl)sulfanyl]acetic acid (0.1 mmol), followed by a solution of O-(7-azabenzotriazol-1-yl)-N,N,N',N'-tetramethyl-uroniumhexafluorophosphate in DMF (0.5 ml), and triethylamine (0.5 mmol). The resulting mixture was shaken at ambient temperature for 16 hours. The solvent was removed by distillation under vacuum, and the crude product purified by preparative HPLC to give 3.2 mg of the title compound. m/z [M+H]⁺603; retention time 4.21 minutes.

Example 4

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1-oxidothietan-3-yl)methanone

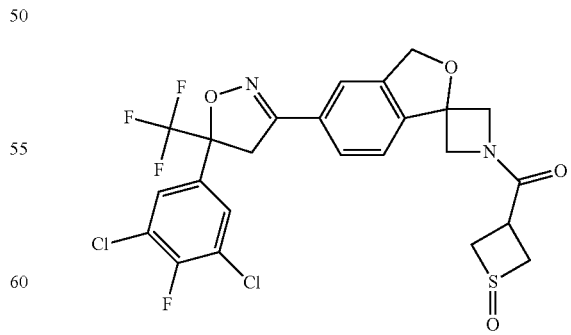

To a solution of thietane-3-carboxylic acid 1-oxide (53 mg, 0.4 mmol) in DMF (5 mL) was added CDI (65 mg, 0.4 mmol). The reaction was stirred at room temperature for 15 minutes and TEA (0.25 mL, 1.6 mmol) and 5'-(5-(3,5-dichloropheny- 4-fluorol)-5-(trifluoromethyl)-4,5-dihydroisoxazol-3-yl)-3'H-spiro[azetidine-3,1'-isobenzofuran] (Preparation 13, 150 mg, 0.3 mmol) were added. The reaction was stirred at room temperature for 18 hours, then diluted with water and extracted with EtOAc (2×75 mL). The combined organic phase was dried (Na$_2$SO$_4$) and concentrated under vacuum to afford the intermediate (100 mg, 53%) as a solid. m/z (CI) 577 [M+H]$^+$.

Example 5

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone

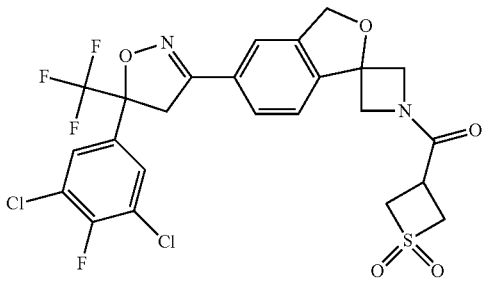 [SMILES: O=C(C1CS(=O)(=O)C1)N1CC2(C1)OCc1cc(C3=NOC(c4cc(Cl)c(F)c(Cl)c4)(C(F)(F)F)C3)ccc12]

To a 20 mL vial containing a solution of oxone (320 mg, 0.52 mmol) in water (2 mL) at 0° C. was added (5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1-oxidothietan-3-yl)methanone from Example 4 (100 mg, 0.17 mmol) as a solution in methanol (4 mL). The reaction was stirred at 0° C. and allowed to warm to room temperature while stirring over 2 hours. Next, the reaction mixture was concentrated to remove excess MeOH and diluted with water. The crude product was extracted with CH$_2$Cl$_2$ (75 mL) and the organic phase was dried (Na$_2$SO$_4$) and concentrated under vacuum. The residue was purified by preparative HPLC to afford the final product (16 mg, 16%) as a solid. $^1$HNMR (CDCl$_3$) δ ppm: 7.69 (1H), 7.63-7.60 (3H), 7.49 (1H), 5.19 (2H), 4.61-4.45 (4H), 4.36 (2H), 4.24-4.09 (3H), 3.72 (1H), 3.30 (1H); m/z (CI) 593 [M+H]$^+$.

Preparation 14

General Amide Coupling, can be Done in a Parallel Fashion

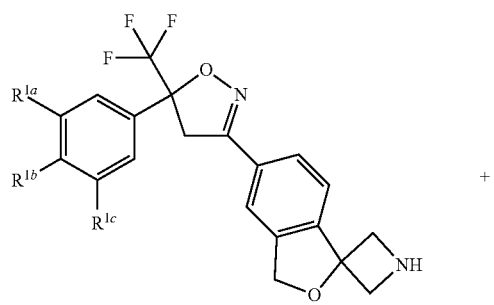

+

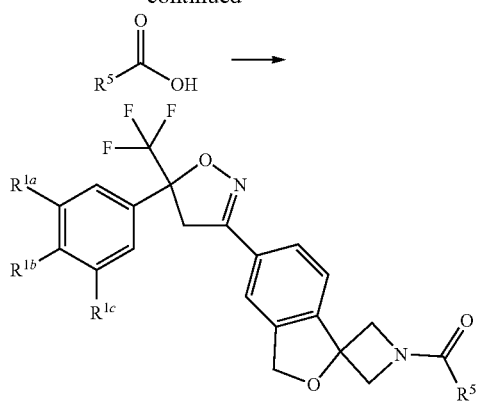

The respective amine (0.05 mmol) was dissolved in DMF (0.5 ml); this was added to the respective acid (0.1 mmol), followed by a solution of O-(7-azabenzotriazol-1-yl)-N,N,N',N'-tetramethyluroniumhexafluorophosphate in DMF (0.5 ml), and triethylamine (0.5 mmol). The resulting mixture was shaken at ambient temperature for 16 hours. The solvent was removed by distillation under vacuum, and the crude product purified by preparative HPLC.

HPLC conditions: Instrument: Waters Alliance 2795 with ZQ MS-ESI+; Column: 4.6×100 NXC18, 5 µm; Flow Rate: 1.0 mL/minute; solvent A 0.05% TFA in water; solvent B ACN; Gradient: 50 to 95% B from 0 to 10 minutes; Injection Volume: 2 µl; Run time: 12 minutes; Detection: 254 nm, and appropriate mass.

Preparation 15

2-bromo-4-(diethoxymethyl)-1-fluorobenzene

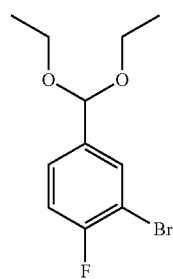

A 250 mL flask was charged with 3-bromo-4-fluorobenzaldehyde (13.5 g, 66.5 mmol), triethyl orthoformate (13.3 mL, 79.8 mmol), and anhydrous EtOH (150 mL). Tetrabutylammonium tribromide was added and the reaction mixture was allowed to stir at room temperature for 48 hours. The crude reaction was poured into aqueous NaHCO$_3$ and extracted with ethyl acetate (75 ml). The organic layers were combined, dried with Na$_2$SO$_4$ and reduced under vacuum to afford the intermediate (16.2 g, 88%) as a clear oil. $^1$HNMR (CDCl$_3$) δ ppm: 7.71 (1H), 7.40 (1H), 7.12 (1H), 5.48 (1H), 3.65-3.51 (4H), 1.28-1.24 (6H).

Preparation 16

1-benzhydryl-3-(2-bromo-4-(diethoxymethyl)phenyl)azetidine-3-carbonitrile

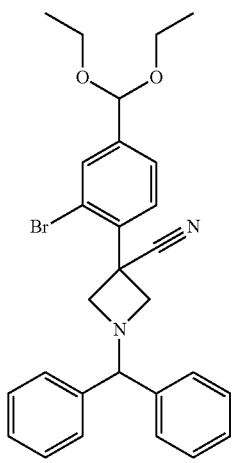 [SMILES: CCOC(OCC)c1ccc(C2(C#N)CN(C(c3ccccc3)c3ccccc3)C2)c(Br)c1]

To a solution of 2-bromo-4-(diethoxymethyl)-1-fluorobenzene (Preparation 15, 10.0 g, 36.0 mmol) in THF (125 mL) was added 1-benzhydrylazetidine-3-carbonitrile (13.4 g, 54.1 mmol) and KHMDS (10.8 g, 54.1 mmol). The reaction mixture is left stirring at room temperature for 1 hour. Next, the reaction mixture is concentrated to an oil under vacuum, diluted with EtOAc, and washed 2× with water. The organic phase was dried ($Na_2SO_4$) and concentrated under vacuum. The crude material was chromatographed (220 g Redi-Sep column) eluting from 100% heptane to 20:80 EtOAc:heptane to afford the intermediate (13.7 g, 75%) as a solid. $^1$HNMR (CDCl$_3$) δ ppm: 7.73 (1H), 7.48-7.44 (5H), 7.37-23 (6H), 7.13 (1H), 5.47 (1H), 4.33 (1H), 4.14 (2H), 3.65-3.52 (4H), 3.41 (2H), 1.29-1.25 (6H).

Preparation 17

1-benzhydryl-3-(2-bromo-4-(diethoxymethyl)phenyl)azetidine-3-carboxylic acid

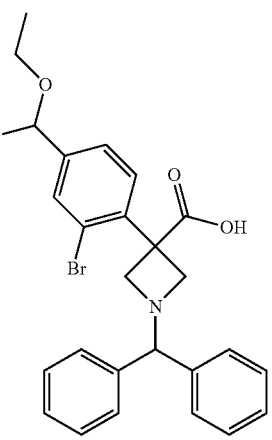

To a suspension of 1-benzhydryl-3-(2-bromo-4-(diethoxymethyl)phenyl)-azetidine-3-carbonitrile (Preparation 16, 13.5 g, 26.7 mmol) in EtOH (150 mL) was added aq NaOH (85 mL of a 25% wt. solution). The reaction mixture was heated to reflux for 36 hours. Contents were concentrated under vacuum to remove EtOH to a concentration of ~100 mL and solution became cloudy. The residue was placed in an ice bath and cooled. The pH of the residue was lowered to ~5-7 by the slow addition of 3M HCl at which time a precipitate formed. Additional water was added and the mixture was stirred for 15 minutes and filtered. The precipitate was re-dissolved in EtOAc (250 mL) and washed with saturated NH$_4$Cl and brine.

The organic phase was dried (Na$_2$SO$_4$) and concentrated under vacuum. The solid was placed under high-vac for 18 h to afford the acid (14.1 g, 100%) as a solid. $^1$HNMR (CDCl$_3$) δ ppm: 7.55 (1H), 7.34-7.13 (11H), 7.02 (1H), 5.37 (1H), 4.40 (1H), 4.16 (2H), 3.58-3.44 (6H), 1.22-1.19 (6H); m/z (CI) 524 [M+H]$^+$.

Preparation 18

1-benzhydryl-5'-(diethoxymethyl)spiro[azetidine-3,1'-isoindolin]-3'-one

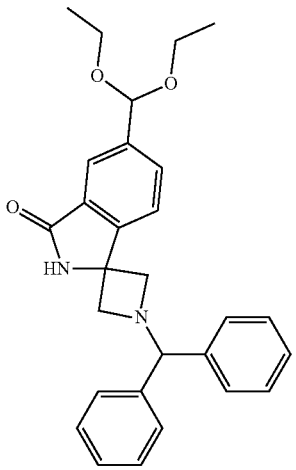 [SMILES: CCOC(OCC)c1ccc2c(c1)C(=O)NC21CN(C(c2ccccc2)c2ccccc2)C1]

To a solution of 1-benzhydryl-3-(2-bromo-4-(diethoxymethyl)phenyl)-azetidine-3-carboxylic acid (Preparation 17, 5.00 g, 9.5 mmol) in CH$_2$Cl$_2$ (100 mL) was added 1-chloro-N,N,2-trimethyl-1-propen-1-amine (1.4 mL, 10.5 mmol). The reaction was stirred at room temperature for 1.5 hours. Next, the reaction was concentrated under vacuum and re-dissolved in anhydrous DMF (75 mL). Sodium azide (950 mg, 8.6 mmol) was added and the reaction mixture was stirred at room temperature for 18 hours. MTBE was next added (200 mL) and the mixture was washed with 0.5M Na$_2$CO$_3$ (2×100 mL), water (100 mL), and brine (100 mL). The organic phase was dried (Na$_2$SO$_4$), diluted with toluene (100 mL), and concentrated under vacuum to remove MTBE. The acyl-azide/toluene solution was next heated to 90° C. for 1 hour. Upon heating, N$_2$ gas evolution was observed. The reaction was then cooled and concentrated under vacuum to afford the crude isocyanate (2.4 g). The residue was dissolved in THF (100 mL) and cooled to −78° C. After ~15 minutes, tert-butyl lithium (5.4 mL, 9.2 mmol) was added drop-wise and stirring continued for another 10 minutes at −78° C. The reaction mixture was then warmed to 0° C. and maintained at that temperature for ~10 minutes. The reaction was quenched with sat NH$_4$Cl and warmed to room temperature. Additional saturated NH$_4$Cl was added and the reaction was extracted with MTBE. The organic phase was dried (Na$_2$SO$_4$) and concentrated under vacuum. The crude material was chromatographed (80 g Redi-Sep column) eluting from 100% hexanes to 50:50 EtOAc:hexanes to afford the intermediate (1.41 g, 33%) as a solid. $^1$HNMR (CDCl$_3$) δ ppm: 8.12 (1H), 7.95 (1H), 7.86 (1H), 7.53-7.51 (4H), 7.34-7.21 (6H), 6.88 (1H), 5.61 (1H), 4.49 (1H), 3.68-3.56 (6H), 3.45 (2H), 1.29-1.26 (6H); m/z (CI) 443 [M+H]$^+$.

Preparation 19 tert-butyl 5'-(diethoxymethyl)-3'-oxospiro[azetidine-3,1'-isoindoline]-1-carboxylate

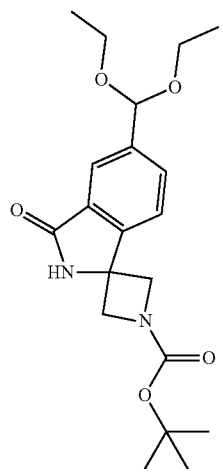 [SMILES: CCOC(OCC)c1ccc2c(c1)C(=O)NC21CN(C(=O)OC(C)(C)C)C1]

To a deoxygenated solution of 1-benzhydryl-5'-(diethoxymethyl)spiro-[azetidine-3,1'-isoindolin]-3'-one (Preparation 18, 1.4 g, 3.2 mmol) in EtOH (75 mL) was added ammonium formate (1.4 g, 22.1 mmol), Boc anhydride (2.1 g, 9.5 mmol) and 10% Pd/C (504 mg, 0.5 mmol). The resulting suspension was heated to reflux while stirring under N$_2$ for 1 hour. The reaction mixture was cooled, filtered through a pad of celite, and the filtrate was concentrated under vacuum. The crude residue was chromatographed (40 g Redi-Sep column) eluting from 100% hexanes to 50:50 EtOAc:hexanes to afford the intermediate (885 mg, 74%) as a solid. $^1$H NMR (CDCl$_3$) δ ppm: 7.96 (1H), 7.83 (1H), 7.74 (1H), 7.13 (1H), 5.60 (1H), 4.38-4.29 (4H), 3.66-3.54 (4H), 1.53 (9H), 1.29-1.25 (6H).

Preparation 20

(E/Z)-tert-butyl 5'-((hydroxyimino)methyl)-3'-oxospiro[azetidine-3,1'-isoindoline]-1-carboxylate

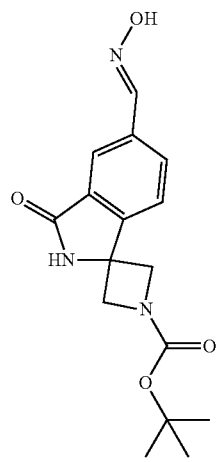 [SMILES: CC(C)(C)OC(=O)N1CC2(C1)NC(=O)c1cc(/C=N/O)ccc12]

To a solution of tert-butyl 5'-(diethoxymethyl)-3'-oxospiro [azetidine-3,1'-isoindoline]-1-carboxylate (Preparation 19, 880 mg, 2.3 mmol) in EtOH (40 mL) was added NH$_2$OH.HCl (330 mg, 4.7 mmol) and water (5 mL). The reaction mixture was heated to 50° C. for 1 hour. The reaction mixture was next cooled and concentrated under vacuum to remove EtOH. Water was added to residue and extracted with CH$_2$Cl$_2$ (2×50 mL). The combined organic phases were dried (Na$_2$SO$_4$) and concentrated under vacuum to afford the intermediate (755 mg, 100%) as a solid. m/z (CI) 262 [M-56+H]$^+$.

Preparation 21 tert-butyl 5'-(5-(3,5-bis(trifluoromethyl)phenyl)-5-(trifluoromethyl)-4,5-dihydroisoxazol-3-yl)-3'-oxospiro[azetidine-3,1'-isoindoline]-1-carboxylate To a DMF (15 mL) solution of (E/Z)-tert-butyl F-((hydroxyimino)methyl)-3'-oxospiro[azetidine-3,1'-isoindoline]-1-carboxylate (Preparation 20, 250 mg, 0.8 mmol) was added NCS (122 mg, 0.9 mmol) portion-wise. The reaction was then heated to 50° C. for 1 hour. Additional NCS (60 mg, 0.4 mmol) was added and heating continued for 30 minutes. The reaction mixture was cooled to room temperature and diluted with EtOAc (15 mL). Next, 1,3-bis(trifluoromethyl)-5-(1,1,1-trifluoroprop-2-en-2-yl)benzene (243 mg, 0.8 mmol) and K$_2$CO$_3$ (174 mg, 1.7 mmol) were added. The mixture was allowed to stir at room temperature for 18 hours. The reaction mixture was diluted with EtOAc and washed with water and brine. The organic phase was dried ($Na_2SO_4$) and concentrated under vacuum. The residue was chromatographed (24 g silica-gel column) eluting from 100% hexanes to 50:50 EtOAc:hexanes to afford the intermediate (245 mg, 50%) as a solid. $^1$H NMR ($CDCl_3$) δ ppm: 8.22 (1H), 8.12 (2H), 8.00-7.97 (2H), 7.86 (1H), 7.23 (1H), 4.40 (2H), 4.32-4.26 (3H), 3.87 (1H), 1.53 (9H); m/z (CI) 568 [M-56+H]$^+$.

Preparation 22

5'-(5-(3,5-bis(trifluoromethyl)phenyl)-5-(trifluoromethyl)-4,5-dihydroisoxazol-3-yl)spiro[azetidine-3,1'-isoindolin]-3'-one

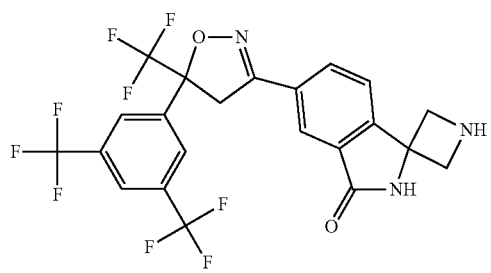 [SMILES: O=C1NC2(CNC2)c2ccc(C3=NOC(c4cc(C(F)(F)F)cc(C(F)(F)F)c4)(C(F)(F)F)C3)cc21]

A 100 mL vial equipped with stir bar was charged with tert-butyl 5'-(5-(3,5-bis(trifluoromethyl)phenyl)-5-(trifluoromethyl)-4,5-dihydroisoxazol-3-yl)-3'-oxospiro[azetidine-3,1'-isoindoline]-1-carboxylate (Preparation 21, 240 mg, 0.4 mmol) and anhydrous methanol (25 mL). A methanolic solution of HCl (1 mL of a 1.25M solution) was added and the reaction was heated to 65° C. for 6 hours. The reaction was cooled and concentrated under vacuum. The residue was rinsed with diethyl ether, concentrated under vacuum, and subsequently placed under high vacuum for 1 hour to afford the intermediate (216 mg, 95%) as an HCl salt. m/z (CI) 524 [M+H]$^+$.

Example 6

5-(5-(3,5-bis(trifluoromethyl)phenyl)-5-(trifluoromethyl)-4,5-dihydroisoxazol-3-yl)-1-(2-(methylsulfonyl)acetyl)spiro[azetidine-3,1'-isoindolin]-3'-one

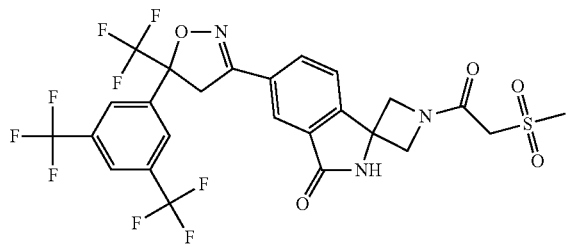 [SMILES: CS(=O)(=O)CC(=O)N1CC2(C1)NC(=O)c1cc(C3=NOC(c4cc(C(F)(F)F)cc(C(F)(F)F)c4)(C(F)(F)F)C3)ccc12]

To a solution of 2-methanesulfonylacetic acid (40 mg, 0.3 mmol) in DMF (5 mL) was added CDI (40 mg, 0.2 mmol). The reaction was stirred at room temperature for 30 minutes and TEA (0.15 mL, 1.0 mmol) and 5'-(5-(3,5-bis(trifluoromethyl)phenyl)-5-(trifluoromethyl)-4,5-dihydroisoxazol-3-yl)spiro[azetidine-3,1'-isoindolin]-3'-one (Preparation 22, 100 mg, 0.2 mmol) were added. The reaction was stirred at room temperature for 18 hours, then diluted with 0.1N NaOH and extracted with EtOAc (2×75 mL). The combined organic phase was dried ($Na_2SO_4$) and concentrated under vacuum. The crude product purified by preparative HPLC (Instrument: Waters Alliance 2795 with ZQ MS-ESI+; Column: 4.6×100 NXC18, 5 μm; Flow Rate: 1.0 mL/min; solvent A 0.05% TFA in water; solvent B ACN; Gradient: 50 to 95% B from 0 to 10 minutes; Injection Volume: 2 μl; Run time: 12 minutes; Detection: 254 nm, and appropriate mass) to afford the final product (54 mg, 44%) as a solid. $^1$HNMR ($CDCl_3$) δ ppm: 8.22 (1H), 8.13 (2H), 8.00 (2H), 7.88 (1H), 7.55 (1H) 4.84 (2H), 4.55 (2H), 4.29 (1H), 3.95 (2H), 3.89 (1H), 3.24 (3H); m/z (CI) 644 [M+H]$^+$.

Preparation 23

General Amide Coupling for Parallel Synthesis

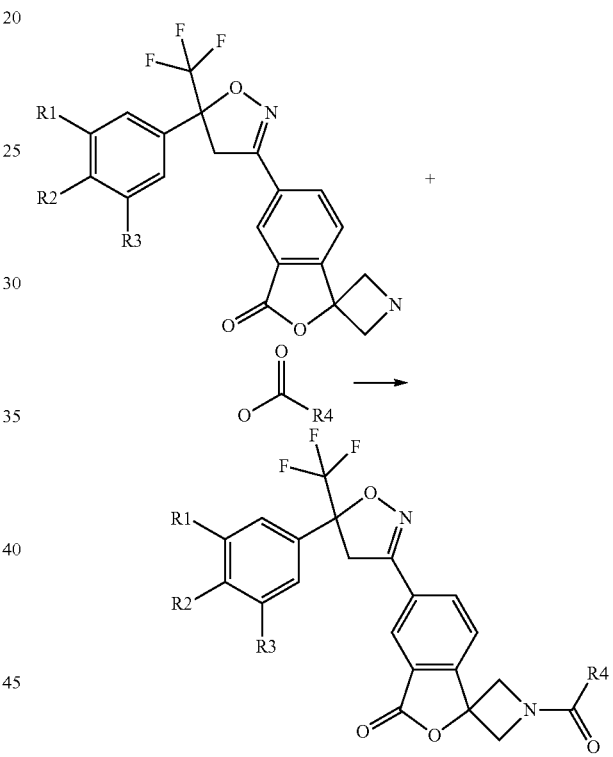

The respective amine (0.05 mmol) was dissolved in DMF (0.5 ml); this was added to the respective acid (0.1 mmol), followed by a solution of O-(7-azabenzotriazol-1-yl)-N,N,N',N'-tetramethyluroniumhexafluorophosphate in DMF (0.5 ml), and triethylamine (0.5 mmol). The resulting mixture was shaken at ambient temperature for 16 hours. The solvent was removed by distillation under vacuum, and the crude product purified by preparative HPLC.
Preparative HPLC Conditions:
Instrument—Waters Autopurifer
Column—Gemini-NX 5 μm, C18, 110A, 100×21.1 mm
Flow—20 mL/minute
MPA—Water with 0.1% formic acid
MPB—Acetonitrile with 0.1% formic acid
Gradient—60% B to 95% B in 5 minutes, hold 5 minutes
Injection Volume—1000 μl
Run Time—10 minutes
Detector—PDA (260 nm) and ESI+

Preparation 24

Chiral Separation of Racemic Products

Chiral separation of enantiomers of the racemic products was performed on a preparative SFC column. Prep SFC=Berger Multigram, Column=Chiralcel OJ 30×250 mm 5 μm, MP A=CO$_2$ MP B=0.1% TEA in MeOH:CH$_2$Cl$_2$, Isocratic 23% B, 120 bar, 100 mL/minute.

Preparation 25 tert-butyl 5'-bromo-3'H-spiro[azetidine-3,1'-isobenzofuran]-1-carboxylate

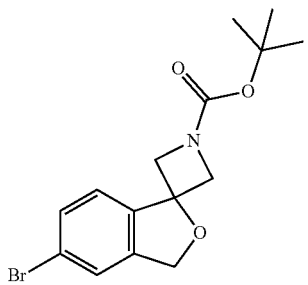 [SMILES: CC(C)(C)OC(=O)N1CC2(C1)OCc1cc(Br)ccc12]

4-bromo-2-(chloromethyl)-1-iodobenzene (500 g, 1.509 moles) was dissolved in tetrahydrofuran (3750 mL) and cooled to −20° C. i-PrMgCl-LiCl (1.3M solution in THF) (1275 ml, 1.66 moles) was added at less than −15° C. The reaction mixture was cooled to −20° C. 3-Oxo-azetidine-1-carboxylic acid, tert-butyl ester (310 g, 1.81 moles), as a solution in tetrahydrofuran (750 mL), was added. The reaction was warmed to room temperature over 90 minutes, and then stirred overnight. 1M Aqueous citric acid solution (2 L) was added, followed by tert-butylmethylether (2 L). The mixture was shaken. The organic phase was separated, dried over anhydrous magnesium sulphate, filtered and evaporated to dryness to give an orange oil. The oil was dissolved in EtOH (2.5 L) and the solution diluted with water (1 L). The mixture stood at room temperature, overnight. The resulting crystals of tert-butyl 5'-bromo-3'H-spiro[azetidine-3,1'-isobenzofuran]-1-carboxylate were filtered under reduced pressure and dried under vacuum at 50° C., giving 290 g. $^1$H NMR (CDCl$_3$) δ ppm: 1.49 (9H, s), 4.15 (2H, d), 4.34 (2H, d), 5.11 (2H, s), 7.38 (2H, m), 7.56 (1H, d).

Preparation 26 tert-butyl 5'-acetyl-3'H-spiro[azetidine-3,1'-isobenzofuran]-1carboxylate

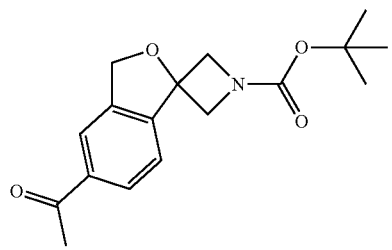 [SMILES: CC(=O)c1ccc2c(c1)COC21CN(C(=O)OC(C)(C)C)C1]

In a scintillation vial containing in 15 mL of EtOH was added Pd(OAc)$_2$ (8.3 mg, 0.037 mmol) and DPPP (31 mg, 0.073 mmol). The reaction vessel was purged with nitrogen gas, capped, and heated to 60° C. for 18 hours. To this was added tert-butyl 5'-bromo-3'H-spiro[azetidine-3,1'-isobenzofuran]-1-carboxylate (Preparation 25, 250 mg, 0.74 mmol) and triethylamine (205 μL, 1.5 mmol) and the mixture was heated to 90° C. for 5 minutes. Butyl vinyl ether (190 uL, 1.5 mmol) was subsequently added and the reaction was heated to 90° C. for 4 hours under nitrogen. The reaction was cooled and 1.0N HCl (2 mL) was added at room temperature and stirred for 2 hours. The reaction was neutralized with saturated NaHCO$_3$ and extracted with EtOAc. The organic phase was dried (Na$_2$SO$_4$) and concentrated under vacuum. The crude material was chromatographed (12 g Redi-Sep column) eluting from 100% hexanes to 35:65 EtOAc:hexanes to afford the intermediate (172 mg, 77%) as a solid. $^1$HNMR (CDCl$_3$) δ ppm: 8.01 (1H), 7.83 (1H), 7.58 (1H), 5.17 (2H) 4.35 (2H), 4.16 (2H), 2.64 (3H), 1.51 (9H); m/z (CI) 204 ([M+H-100]$^+$.

Preparation 27

1-(4-chloro-3,5-difluorophenyl)-2,2,2-trifluoroethanone

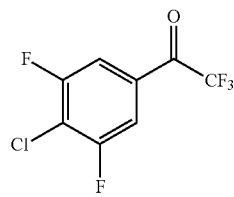 [SMILES: O=C(c1cc(F)c(Cl)c(F)c1)C(F)(F)F]

5-bromo-2-chloro-1,3-difluorobenzene (2000 mg, 8.2 mmol) was stirred at room temperature in THF under N$_2$ and the isopropylmagnesium chloride/LiCl reagent (1310 mg, 9.02 mmol, 6.94 mL) was added over about 1 minute—very slight exotherm noticed to ~30° C. Reaction was stirred at room temperature for 30 minutes followed by the addition of methyl trifluoroacetate (1580 mg, 12.3 mmol, 1.24 mL) over about 1 minute—slight exotherm to ~40° C. Solvents were evaporated under reduced pressure to provide the desired product. $^1$H NMR (CDCl$_3$) δ ppm: 8.05 (s, 2H).

Preparation 28 tert-butyl 5'-(3-(3,5-dichloro-4-fluorophenyl)-4,4,4-trifluorobut-2-enoyl)-3'H-spiro[azetidine-3,1'-isobenzofuran]-1-carboxylate

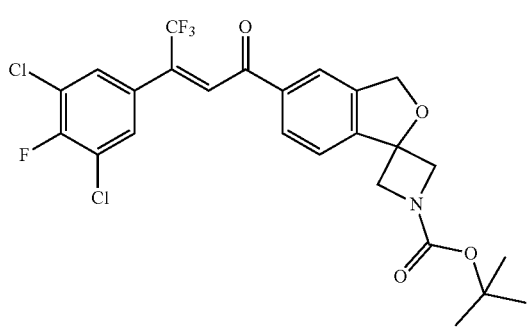 [SMILES: CC(C)(C)OC(=O)N1CC2(C1)OCc1cc(C(=O)/C=C(/c3cc(Cl)c(F)c(Cl)c3)C(F)(F)F)ccc12]

1-(3,5-dichloro-4-fluorophenyl)-2,2,2-trifluoroethanone (Preparation 27, 59.4 g, 227 mmols) and tert-butyl 5'-acetyl-3'H-spiro[azetidine-3,1-isobenzofuran]-1-carboxylate (Preparation 26, 60.0 g, 198 mmols) were mixed in a 1:1 mix of toluene and trifluoromethylbenzene (250 ml) in a 1 L three necked flask. One neck was equipped with a modified short path Dean-Stark head with a condenser on top, and the other with a very low flow nitrogen input (the nitrogen input is off at the beginning of the reaction). The reaction was heated to 110° C. The starting material quickly dissolved and $Cs_2CO_3$ (5 g, 16 mmols) was then added. A vigorous effervescence was observed and the nitrogen flow was connected. The reaction was stirred for 1 hour, emptying the Dean-Stark trap as necessary. HPLC-MS shows about 75% progress. Another 1 g of $Cs_2CO_3$ was added to the crude mixture and the reaction was stirred for an additional 1 hour. An HPLC-Ms shows >95% conversion. The crude reaction was then poured into 500 mL TBME and filtered through a 2" cake of silica. The solvents are removed under vacuum, and the resulting brown gum is re-dissolved in a 1:1 mix of TBME:hexanes, filtered over a 5" cake of silica, and eluted with 2 L of the same solution. The organics were concentrated to dryness. The solids were dissolved in a 95:5 mix of hot heptane:TBME (c.a. 250 ml). The solution was then slowly cooled to 0° C. with stirring and seeded with solids from previous batches. A beige solid formed after 30 minutes. The slurry was left stirring at 0° C. for 2 hours. A pale beige solid was filtered (90 g, 83% yield), showed >99% purity by HPLC, and 85:15 ratio of double bond isomers. The remaining mother liquor was concentrated to an oil (c.a. 30 g) and was purified on a silica cartridge. (400 g, 10-100% TBME in hexanes over 12CV, 100 ml/minute, ~254 nm). An additional 13 g of material is isolated. Analytical method: Xbridge phenyl column (250 mm×3.0 mm); 70% to 100% over 25 minutes, methanol with 0.1% TFA in water with 0.1% TFA, ~254 nm: 16.019 minutes (84.5% major isomer) and 16.439 minutes (14.9%, minor isomer). LC-MS method: Xbridge C18 column; 90% to 100% Acetonitrile/Methanol 1:1 with water; [546] Ms+~4.970 minutes, ~254 nm (single peak).

Preparation 29

Chiral-tert-butyl 5'-(5-(3,5-dichloro-4-fluorophenyl)-5-(trifluoromethyl)-4,5-dihydroisoxazol-3-yl)-3'H-spiro[azetidine-3,1'-isobenzofuran]-1-carboxylate

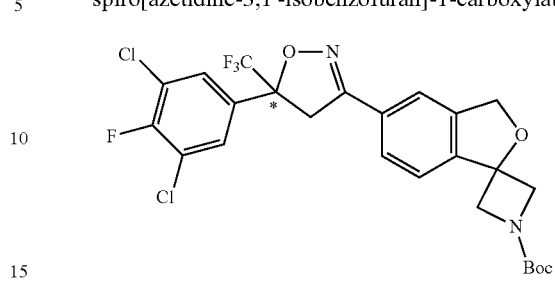

A solution of (Z)-tert-butyl 5'43-(3,5-dichloro-4-fluorophenyl)-4,4,4-trifluorobut-2-enoyl)-3'H-spiro[azetidine-3,1'-isobenzofuran]-1-carboxylate (Preparation 28, 1.0 g, 1.83 mmol) in dichloroethane (8 mL) was cooled to −2° C. The catalyst, (2S)-1-(acridin-9-ylmethyl)-24 (R)-hydroxy(6-methoxyquinolin-4-yl)methyl)-5-vinylquinuclidin-1-ium bromide (180 mg, 0.37 mmol) was added and stirred to dissolve. In a separate flask, 10N aqueous sodium hydroxide (0.42 mL) was cooled to 5'C and 50 wt % aqueous hydroxylamine (254 mg, 3.84 mmol) was added and stirred for 10 minutes. This basic solution was added in one shot to the reaction solution. The resulting solution was stirred at O'C for 1 hour. The reaction mixture was washed with water (2×10 mL). The solution was concentrated to a volume of 3 mL and then 15 mL of methyl tert-butyl ether was added and the heterogeneous mixture was stirred at ambient temperature for 15 minutes. The precipitated catalyst was removed by filtration. The organic solution at this point contained a 90:10 mixture of isoxazoline enantiomers. The organics were concentrated to a volume of 3 mL and the product was allowed to slowly crystallize at ambient temperature and was then cooled to 0° C. The product was isolated by filtration to afford 910 mg (89%) of white crystals. The crystallization generally provided an enantiomeric upgrading such that the percentage of active isomer was >95%. Chiral LC: Chiralpak AD 250× 3.0 mm column, 70:30 hexane:ethanol (0.2% diethylamine), 1.0 mL/minute, 260 nm detection. Retention times: 5.4 minutes and 12.4 minutes. $^{1}H$ NMR, 600 MHz ($CDCl_3$) δ ppm: 7.70 (d, 1H), 7.60 (m, 4H), 5.18 (s, 2H), 4.36 (d, 2H), 4.15 (m, 3H), 3.72 (d, 1H), 1.55 (s, 9H). m/z 462 ([M+H]-Boc). The asterisk (*) depicts a chiral center.

Preparation 30

Chiral—5-(5-(3,5-dichloro-4-fluorophenyl)-5-(trifluoromethyl)-4,5-dihydroisoxazol-3-yl)-3'H-spiro[azetidine-3,1'-isobenzofuran]hydrochloride

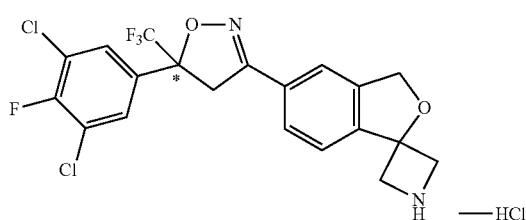

Chiral-tert-butyl 5'-(5-(3,5-dichloro-4-fluorophenyl)-5-(trifluoromethyl)-4,5-dihydroisoxazol-3-yl)-3'H-spiro[azetidine-3,1'-isobenzofuran]-1-carboxylate (Preparation 29, 1.1 g, 2.0 mmol) was dissolved in methanol (50 mL). A methanolic solution of HCl (5 mL of a 1.25M solution) was added and the reaction was heated to 65° C. for 18 hours. The reaction was cooled and concentrated under vacuum to afford the intermediate (980 mg, 100%) a solid. $^1$H NMR, 300 MHz ($d_6$-DMSO) δ ppm: 9.86 (1H), 9.45 (1H), 8.14 (1H), 7.82 (3H), 7.70 (1H), 5.15 (2H), 4.41-4.30 (6H); m/z (CI) 461 [M+H] (free amine). The asterisk (*) depicts a chiral center.

Preparation 31

Chiral-5'-(5-(3,5-dichloro-4-fluorophenyl)-5-(trifluoromethyl)-4,5-dihydroisoxazol-3-yl)-3'H-spiro[azetidine-3,1'-isobenzofuran]para-toluene sulfonate

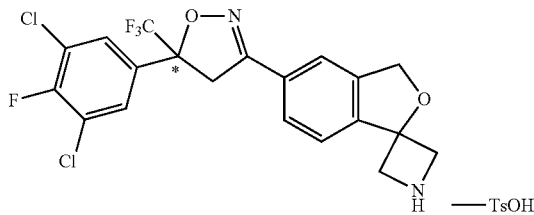

Chiral-tert-butyl 5'-(5-(3,5-dichloro-4-fluorophenyl)-5-(trifluoromethyl)-4,5-dihydroisoxazol-3-yl)-3'H-spiro[azetidine-3,1'-isobenzofuran]-1-carboxylate (Preparation 29, 162 g, 289 mmol) was dissolved in ethanol (1800 mL) and water (200 mL). p-Toluenesulfonic acid monohydrate (113 g, 577 mmol) was added and the solution was heated to 75° C. for 3 hours. The reaction was cooled to 20° C. and was filtered to isolate the product. The product was dried to afford 167.4 g (92%) of a white powder. $^1$H NMR, 600 MHz ($d_6$-DMSO) δ ppm: 8.98 (br s, 2H), 7.92 (d, 1H), 7.80 (m, 3H), 7.70 (s, 1H), 7.50 (d, 2H), 7.15 (d, 2H), 5.15 (s, 2H), 4.40 (m, 6H), 2.25 (s, 3H); m/z (CI) 461 [M+H] (free amine). The asterisk (*) depicts a chiral center.

Example 7

Chiral-1-(5'-(5-(3,5-dichloro-4-fluorophenyl)-5-(trifluoromethyl)-4,5-dihydroisoxazol-3-yl)-3'H-spiro [azetidine-3,1'-isobenzofuran]-1-yl)-2-(methylthio)ethanone

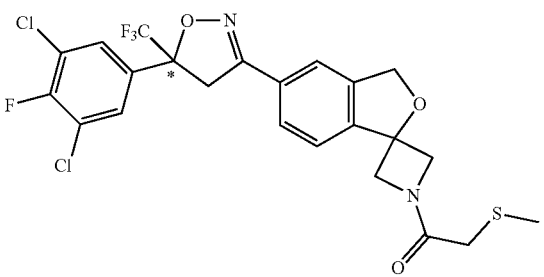 [SMILES: CSCC(=O)N1CC2(C1)OCc1cc(C3=NOC(c4cc(Cl)c(F)c(Cl)c4)(C(F)(F)F)C3)ccc12]

To a solution of 2-(methylthio)acetic acid (210 mg, 2.0 mmol) in DMF (15 mL) was added CDI (390 mg, 2.3 mmol). The reaction was stirred at room temperature for 15 minutes then TEA (1.4 mL, 9.7 mmol) and Chiral—5'-(5-(3,5-dichloro-4-fluorophenyl)-5-(trifluoromethyl)-4,5-dihydroisoxazol-3-yl)-3'H-spiro[azetidine-3,1-isobenzofuran] hydrochloride (Preparation 30, 970 mg, 2.0 mmol) were added. The reaction was stirred at room temperature for 18 hours, then diluted with 0.1 N NaOH and extracted with EtOAc (2×75 mL). The combined organic phase was dried ($Na_2SO_4$) and concentrated under vacuum. The residue was chromatographed (40 g silica-gel column) eluting from 100% hexanes to 40:60 EtOAc:hexanes to afford the desired product (772 mg, 72%) as a solid. $^1$HNMR (CDCl$_3$) δ ppm: 7.68 (1H), 7.60 (3H), 7.54 (1H), 5.18 (2H), 4.64 (1H), 4.45 (2H), 4.32 (1H) 4.11 (1H), 3.72 (1H), 3.15 (2H), 2.30 (3H); m/z (CI) 549 [M+H]$^+$. The asterisk (*) depicts a chiral center.

Example 8

Chiral-1-(5'-(5-(3,5-dichloro-4-fluorophenyl)-5-(trifluoromethyl)-4,5-dihydroisoxazol-3-yl)-3'H-spiro [azetidine-3,1'-isobenzofuran]-1-yl)-2-(methylsulfinyl)ethanone—mixture of diastereomers at the sulfoxide

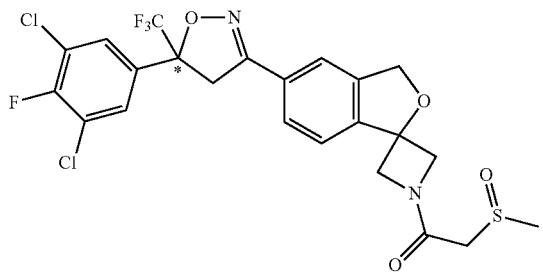 [SMILES: CS(=O)CC(=O)N1CC2(C1)OCc1cc(C3=NOC(c4cc(Cl)c(F)c(Cl)c4)(C(F)(F)F)C3)ccc12]

To a flask containing 18 mL of water at 0° C. was added sodium periodate (345 mg, 1.6 mmol). Next, a solution of Chiral-1-(5'-(5-(3,5-dichloro-4-fluorophenyl)-5-(trifluoromethyl)-4,5-dihydroisoxazol-3-yl)-3'H-spiro[azetidine-3, 1-isobenzofuran]-1-yl)-2-(methylthio)ethanone (Example 7, 770 mg, 1.4 mmol) in methanol (30 mL) was added while stirring. The reaction was allowed to warm to room temperature and stir overnight. Next, the reaction was diluted with water (100 mL) and the crude product was extracted with $CH_2Cl_2$ (2×75 mL). The combined organic phase was dried ($Na_2SO_4$) and concentrated under vacuum. The residue was chromatographed (40 g silica-gel column) eluting from 100% hexanes to 90:10 $CH_2Cl_2$:MeOH to afford the product (658 mg, 83%) as a mixture of diastereomers. $^1$HNMR (CDCl$_3$) δ ppm: 7.72-7.60 (5H), 5.18 (2H), 4.69-4.62 (2H), 4.48-4.38 (2H), 4.10 (1H) 3.86-3.33 (3H), 2.87-2.83 (3H); m/z (CI) 565 [M+H]$^+$. The asterisk (*) depicts a chiral center.

Example 9

Chiral-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone

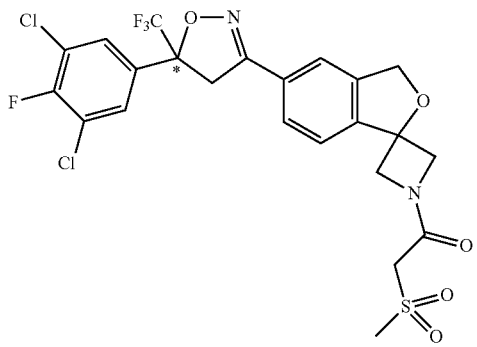 [SMILES: CS(=O)(=O)CC(=O)N1CC2(C1)OCc1cc(C3=NOC(c4cc(Cl)c(F)c(Cl)c4)(C(F)(F)F)C3)ccc12]

The p-toluenesulfonic acid salt of Chiral-5'-(5-(3,5-dichloro-4-fluorophenyl)-5-(trifluoromethyl)-4,5-dihydroisoxazol-3-yl)-3'H-spiro[azetidine-3,1-isobenzofuran] (Preparation 31,157 g, 248 mmol) was stirred as a slurry in methyl tert-butyl ether (700 mL) at ambient temperature. To this was added 0.5N aqueous sodium hydroxide (600 mL, 300 mmol) and the mixture was stirred for 15 minutes at which time the two layers were clear. The aqueous layer was separated and the organics were washed with saturated brine (200 mL) and dried with sodium sulfate (5 gm). The organics were filtered to remove the solids.

In a separate flask, 43.2 gm (297 mmol) of 2-methansulfonylacetic acid was dissolved in DMF (300 mL) at ambient temperature. Carbonyldiimidazole (45.1 gm, 271 mmol) was added portionwise to the solution over 15 minutes to control foaming. After addition, the solution was stirred for 15 minutes at ambient temperature. The above ethereal solution of the amine was added to this reaction in one portion. The resulting solution was stirred at ambient temperature for 30 minutes. Water (800 mL) was added to quench the reaction. After stirring for two minutes, the aqueous layer is settled and removed. The organic layer is stirred at ambient temperature for one hour. During this time, the racemate precipitated from the reaction mixture. The mixture is then filtered through filter aid (Celite 545) to remove the racemic material. The sulfonamide remaining in solution is greater than 99% of a single isomer. The organic solution is washed with water twice (2×1 L) and concentrated to an off-white solid. (138.2 gm, 96%) Residual color can be removed by dissolving material in ethanol, stirring with 10 wt % charcoal (Darco G-60), filtering, and concentrating to a solid.

Chiral HPLC of the sulfonamide enantiomers: Chiralpak IA column (250×3.0 mm), isocratic 50/50 methyl tert-butyl ether/ethanol with 0.2% diethylamine, flow rate 1.0 mL/minute, detection at 260 nm. Retention times: 8.5 minutes (active isomer product), 16.5 minutes (inactive minor isomer). The isolated solid is 99% active isomer and 1% or less of the inactive isomer. Further enantiomeric enrichment can be obtained by stirring in MTBE (for example) and filtering any solids which form. Product was identical to the first eluting enantiomer of the racemate under the preparative chiral SFC conditions described in Preparation 24. $^1$H NMR, 600 MHz (d$_6$-DMSO): 7.88 (d, 2H), 7.82 (d, 1H), 7.73 (m, 2H), 5.18 (s, 2H), 4.62 (dd, 2H), 4.42 (dd, 2H), 4.28 (m, 4H), 3.20 (s, 3H); m/z(CI) 582 [M+1-1]. The asterisk (*) depicts a chiral center.

The following chromatographic conditions were used to obtain quoted retention times for synthesized compounds of Table 1, 2, and 3.
Standard Conditions
Instrument—Waters Alliance 2795 with ZQ MS ESI+
Column—Gemini-NX 5 μm, C18, 110A, 100×4.6 mm
Flow—1 mL/minute
MP A—Water with 0.1% formic acid
MP B—Acetonitrile with 0.1% formic acid
Gradient—50% B to 95% B in 5 minutes, hold 5 minutes
Injection Volume—2 μl
Run Time—10 minutes
Detector—PDA (260 nm) and ESI+

By the methods described herein, the following spirocyclic lactone Examples of Table 1 were prepared from Formula 1.1a.

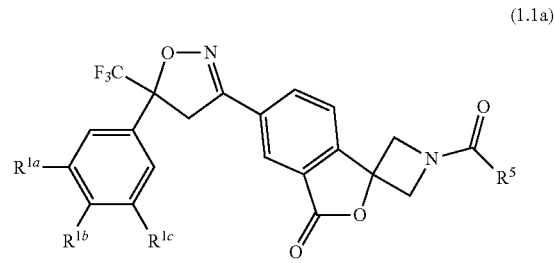

(1.1a)

TABLE 1

Spirocyclic Lactones

| Example No. | $R^{1a}$ | $R^{1b}$ | $R^{1c}$ | $R^5$ | m/z (ESI) [M + H]+ | Retention Time (minutes) |
|---|---|---|---|---|---|---|
| 10 | Cl | F | Cl | cyclopropyl | 543 | 4.59 |
| 11 | Cl | F | Cl | isobutyl | 559 | 4.07 |
| 12 | Cl | F | Cl | —C(OH)(CH$_3$)$_2$ | 561 | 4.09 |
| 13 | Cl | F | Cl | —CH$_2$-cyclopropyl | 557 | 4.78 |
| 14 | Cl | F | Cl | methyl | 517 | 4.09 |
| 15 | Cl | F | Cl | ⌳-OH (cyclopropyl-OH) | 559 | 4.03 |
| 16 | Cl | F | Cl | cyclobutyl | 557 | 4.95 |

TABLE 1-continued

Spirocyclic Lactones

| Example No. | $R^{1a}$ | $R^{1b}$ | $R^{1c}$ | $R^5$ | m/z (ESI) [M + H]+ | Retention Time (minutes) |
|---|---|---|---|---|---|---|
| 17 | Cl | F | Cl | t-butyl | 559 | 4.03 |
| 18 | Cl | F | Cl | —CH$_2$OH | 533 | 3.62 |
| 19 | Cl | F | Cl | —CH$_2$CH(CH$_3$)(OH) | 561 | 3.79 |
| 20 | Cl | F | Cl | propyl | 545 | 4.80 |
| 21 | Cl | F | Cl | —CH$_2$SCH$_3$ | 563 | 4.63 |
| 22 | Cl | F | Cl | 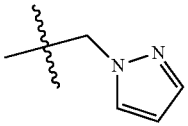 [SMILES: *Cn1cccn1] | 583 | 4.23 |
| 23 | Cl | F | Cl | 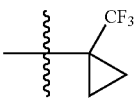 | 611 | 5.20 |
| 24 | Cl | F | Cl | isopropyl | 545 | 4.78 |
| 25 | Cl | F | Cl | 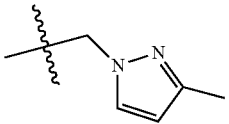 [SMILES: *Cn1ccc(C)n1] | 597 | 4.39 |
| 26 | Cl | F | Cl | —CH(CH$_3$)CH$_2$OH | 561 | 3.76 |
| 27 | Cl | F | Cl | 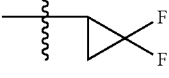 | 579 | 4.78 |
| 28 | Cl | F | Cl | —CH$_2$CF$_3$ | 585 | 4.82 |

The Examples of Table 1 were named using ChemBio-Draw Ultra 12.0 of ChemBioOffice 2010 and include:

1-(cyclopropanecarbonyl)-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one (10);

5'-(5-(3,5-dichloro-4-fluorophenyl)-5-(trifluoromethyl)-4,5-dihydroisoxazol-3-yl)-1-(3-methylbutanoyl)-3'H-spiro[azetidine-3,1-isobenzofuran]-3'-one (11);

5'-(5-(3,5-dichloro-4-fluorophenyl)-5-(trifluoromethyl)-4,5-dihydroisoxazol-3-yl)-1-(2-hydroxy-2-methylpropanoyl)-3'H-spiro[azetidine-3,1'-isobenzofuran]-3'-one (12);

1-(2-cyclopropylacetyl)-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one (13);

1-acetyl-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one (14);

5'-(5-(3,5-dichloro-4-fluorophenyl)-5-(trifluoromethyl)-4,5-dihydroisoxazol-3-yl)-1-(1-hydroxycyclopropanecarbonyl)-3'H-spiro[azetidine-3,1'-isobenzofuran]-3'-one (15);

1-(cyclobutanecarbonyl)-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one (16);

5'-(5-(3,5-dichloro-4-fluorophenyl)-5-(trifluoromethyl)-4,5-dihydroisoxazol-3-yl)-1-piyaloyl-3'H-spiro[azetidine-3,1'-isobenzofuran]-3'-one (17);

5'-(5-(3,5-dichloro-4-fluorophenyl)-5-(trifluoromethyl)-4,5-dihydroisoxazol-3-yl)-1-(2-hydroxyacetyl)-3'H-spiro[azetidine-3,1'-isobenzofuran]-3'-one (18);

5'-(5-(3,5-dichloro-4-fluorophenyl)-5-(trifluoromethyl)-4,5-dihydroisoxazol-3-yl)-1-(2-(1-hydroxycyclopropyl)acetyl)-3'H-spiro[azetidine-3,1'-isobenzofuran]-3'-one (19);

1-butyryl-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one (20);

5'-(5-(3,5-dichloro-4-fluorophenyl)-5-(trifluoromethyl)-4,5-dihydroisoxazol-3-yl)-1-(2-(methylthio)acetyl)-3'H-spiro[azetidine-3,1'-isobenzofuran]-3'-one (21);

5'-(5-(3,5-dichloro-4-fluorophenyl)-5-(trifluoromethyl)-4,5-dihydroisoxazol-3-yl)-1-(2-(methylsulfinyl)acetyl)-3'H-spiro[azetidine-3,1'-isobenzofuran]-3'-one (sulfinyl of 21);

5'-(5-(3,5-dichloro-4-fluorophenyl)-5-(trifluoromethyl)-4,5-dihydroisoxazol-3-yl)-1-(2-(methylsulfonyl)acetyl)-3'H-spiro[azetidine-3,1'-isobenzofuran]-3'-one (sulfonyl of 21);

1-(2-(1H-pyrazol-1-yl)acetyl)-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one (22);

5'-(5-(3,5-dichloro-4-fluorophenyl)-5-(trifluoromethyl)-4,5-dihydroisoxazol-3-yl)-1-(1-(trifluoromethyl)cyclopropanecarbonyl)-3'H-spiro[azetidine-3,1'-isobenzofuran]-3'-one (23);

5'-(5-(3,5-dichloro-4-fluorophenyl)-5-(trifluoromethyl)-4,5-dihydroisoxazol-3-yl)-1-isobutyryl-3'H-spiro[azetidine-3,1'-isobenzofuran]-3'-one (24);

5'-(5-(3,5-dichloro-4-fluorophenyl)-5-(trifluoromethyl)-4,5-dihydroisoxazol-3-yl)-1-(2-(3-methyl-1H-pyrazol-1-yl)acetyl)-3'H-spiro[azetidine-3,1'-isobenzofuran]-3'-one (25);

5'-(5-(3,5-dichloro-4-fluorophenyl)-5-(trifluoromethyl)-4,5-dihydroisoxazol-3-yl)-1-(3-hydroxy-2-methylpropanoyl)-3'H-spiro[azetidine-3,1'-isobenzofuran]-3'-one (26);

5'-(5-(3,5-dichloro-4-fluorophenyl)-5-(trifluoromethyl)-4,5-dihydroisoxazol-3-yl)-1-(2,2-difluorocyclopropanecarbonyl)-3'H-spiro[azetidine-3,1'-isobenzofuran]-3'-one (27); and 5'-(5-(3,5-dichloro-4-fluorophenyl)-5-(trifluoromethyl)-4,5-dihydroisoxazol-3-yl)-1-(4,4,4-trifluorobutanoyl)-3'H-spiro[azetidine-3,1'-isobenzofuran]-3'-one (28).

By the methods described herein, the following spirocyclic ether Examples of Table 2 were prepared from Formula 1.2a.

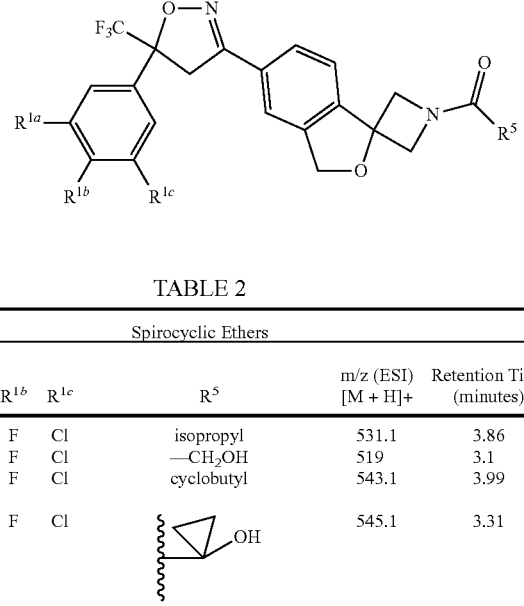

(1.2a)

TABLE 2

Spirocyclic Ethers

| Example No. | $R^{1a}$ | $R^{1b}$ | $R^{1c}$ | $R^5$ | m/z (ESI) [M + H]+ | Retention Time (minutes) |
|---|---|---|---|---|---|---|
| 29 | Cl | F | Cl | isopropyl | 531.1 | 3.86 |
| 30 | Cl | F | Cl | —CH$_2$OH | 519 | 3.1 |
| 31 | Cl | F | Cl | cyclobutyl | 543.1 | 3.99 |
| 32 | Cl | F | Cl | ⟨cyclopropyl-OH⟩ | 545.1 | 3.31 |
| 33 | Cl | F | Cl | CH$_2$NHCHO | 546.1 | 2.98 |
| 34 | Cl | F | Cl | methyl | 503 | 3.41 |
| 35 | Cl | F | Cl | ethyl | 517.1 | 3.66 |
| 36 | Cl | F | Cl | —C(OH)(CH$_3$)$_2$ | 547.1 | 3.35 |
| 37 | Cl | F | Cl | —CH$_2$-cyclopropyl | 543.1 | 3.88 |
| 38 | Cl | F | Cl | t-butyl | 545.1 | 4.14 |
| 39 | Cl | F | Cl | ⟨cyclopropyl-CF$_3$⟩ | 597.1 | 4.23 |
| 40 | Cl | F | Cl | —CH(CH$_3$)CH$_2$OH | 547.1 | 3.16 |
| 41 | Cl | F | Cl | ⟨CH$_2$-pyrazolyl-methyl⟩ | 583.1 | 3.50 |
| 42 | Cl | F | Cl | isobutyl | 545.1 | 4.07 |
| 43 | Cl | F | Cl | ⟨C(CH$_3$)$_2$CH$_2$-pyrazolyl⟩ | 569.1 | 3.46 |
| 44 | Cl | F | Cl | —CH$_2$CH(CH$_3$)(OH) | 547.1 | 3.19 |
| 45 | Cl | F | Cl | cyclopropyl | 529.1 | 3.75 |
| 46 | Cl | F | Cl | propyl | 531.1 | 3.87 |
| 47 | Cl | F | Cl | ⟨thietanyl⟩ | 561 | nt |
| 48 | Cl | F | Cl | CH$_2$S(O)$_2$CH$_3$ | 581 | 3.43 |
| 48a^, identical to Example 9 | Cl | F | Cl | CH$_2$S(O)$_2$CH$_3$ | 581 | nt |
| 48b^ | Cl | F | Cl | CH$_2$S(O)$_2$CH$_3$ | 581 | nt |

TABLE 2-continued

Spirocyclic Ethers

| Example No. | R$^{1a}$ | R$^{1b}$ | R$^{1c}$ | R$^5$ | m/z (ESI) [M + H]+ | Retention Time (minutes) |
|---|---|---|---|---|---|---|
| 49a^ | Cl | F | Cl | cyclobutyl-SO$_2$ (thietane 1,1-dioxide) | 593 | nt |
| 50 | Cl | Cl | Cl | —CH$_2$S(O)$_2$CH$_3$ | 599 | 3.52 |
| 51 | Cl | H | Cl | —CH$_2$S(O)$_2$CH$_3$ | 563 | 3.40 |
| 52 | Cl | H | CF$_3$ | —CH$_2$S(O)$_2$CH$_3$ | 597 | 3.45 |
| 53 | Cl | Cl | CF$_3$ | —CH$_2$S(O)$_2$CH$_3$ | 631 | 3.57 |
| 54 | Cl | Br | Cl | —CH$_2$S(O)$_2$CH$_3$ | 642 | 3.48 |
| 55 | CF$_3$ | H | CF$_3$ | —CH$_2$S(O)$_2$CH$_3$ | 631 | nt |
| 56 | Cl | H | Br | —CH$_2$S(O)$_2$CH$_3$ | 609 | nt |
| 57 | CF$_3$ | Cl | CF$_3$ | —CH$_2$S(O)$_2$CH$_3$ | 665 | nt |
| 58 | Cl | H | F | —CH$_2$S(O)$_2$CH$_3$ | 547 | nt |
| 59 | Cl | F | H | —CH$_2$S(O)$_2$CH$_3$ | 547 | nt |
| 60 | CF$_3$ | H | H | —CH$_2$S(O)$_2$CH$_3$ | 563 | nt |

^ indicates single enantiomer obtained by chiral SFC separation of racemic product.
a^ indicates first eluting enantiomer.
b^ indicates second eluting enantiomer.
nt—not tested.

The Examples of Table 2 were named using ChemBioDraw Ultra 12.0 of ChemBioOffice 2010 and include:

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-methylpropan-1-one (29);

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-hydroxyethanone (30);

cyclobutyl(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)methanone (31);

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1-hydroxycyclopropyl)methanone (32);

N-(2-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-oxoethyl)formamide (33);

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)ethanone (34);

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)propan-1-one (35);

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-hydroxy-2-methylpropan-1-one (36);

2-cyclopropyl-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)ethanone (37);

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2,2-dimethylpropan-1-one (38);

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1-(trifluoromethyl)cyclopropyl)methanone (39);

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-3-hydroxy-2-methylpropan-1-one (40);

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(3-methyl-1H-pyrazol-1-yl)ethanone (41);

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-3-methylbutan-1-one (42);

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(1H-pyrazol-1-yl)ethanone (43);

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-3-hydroxybutan-1-one (44); cyclopropyl(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)methanone (45);

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-Abutan-1-one (46);

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(thietan-3-yl)methanone (47);

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone (48);

Chiral-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone (48a,b);

Chiral-(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone (49a);

2-(methylsulfonyl)-1-(5'-(5-(3,4,5-trichlorophenyl)-5-(trifluoromethyl)-4,5-dihydroisoxazol-3-yl)-3'H-spiro[azetidine-3,1'-isobenzofuran]-1-yl)ethanone (50);

1-(5'-(5-(3,5-dichlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone (51);
1-(5'-(5-(3-chloro-5-(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone (52);
1-(5'-(5-(3,4-dichloro-5-(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)-ethanone (53);
1-(5'-(5-(4-bromo-3,5-dichlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone (54);
1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone (55);
1-(5'-(5-(3-bromo-5-chlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone (56);
1-(5'-(5-(4-chloro-3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone (57);
1-(5'-(5-(3-chloro-5-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone (58);
1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone (59); and
2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone (60).

By the methods described herein, the following spirocyclic lactam Examples of Table 3 were prepared from Formula 1.3a.

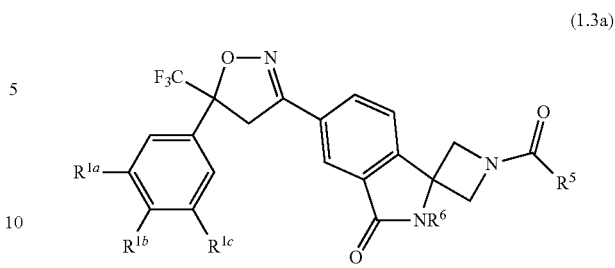

(1.3a)

The Examples of Table 3 were named using ChemBioDraw Ultra 12.0 of ChemBioOffice 2010 and include:

5'-(5-(3,5-dichloro-4-fluorophenyl)-5-(trifluoromethyl)-4,5-dihydroisoxazol-3-yl)-1-(2-(methylsulfonyl)acetyl)spiro[azetidine-3,1'-isoindolin]-3'-one (61);
1-(cyclopropanecarbonyl)-5'-(5-(3,5-dichloro-4-fluorophenyl)-5-(trifluoromethyl)-4,5-dihydroisoxazol-3-yl)spiro[azetidine-3,1'-isoindolin]-3'-one (62);
5'-(5-(3,4-dichloro-5-(trifluoromethyl)phenyl)-5-(trifluoromethyl)-4,5-dihydroisoxazol-3-yl)-1-(2-(methylsulfonyl)acetyl)spiro[azetidine-3,1'-isoindolin]-3'-one (63);
1-(2-(methylsulfonyl)acetyl)-5'-(5-(3,4,5-trichlorophenyl)-5-(trifluoromethyl)-4,5-dihydroisoxazol-3-yl)spiro[azetidine-3,1'-isoindolin]-3'-one (64);
5'-(5-(3-chloro-5-(trifluoromethyl)phenyl)-5-(trifluoromethyl)-4,5-dihydroisoxazol-3-yl)-1-(2-(methylsulfonyl)acetyl)spiro[azetidine-3,1'-isoindolin]-3'-one (65);
5'-(5-(4-bromo-3,5-dichlorophenyl)-5-(trifluoromethyl)-4,5-dihydroisoxazol-3-yl)-1-(2-(methylsulfonyl)acetyl)spiro[azetidine-3,1'-isoindolin]-3'-one (66);

TABLE 3

Spirocyclic Lactams

| Example No. | $R^{1a}$ | $R^{1b}$ | $R^{1c}$ | $R^5$ | $R^6$ | m/z (ESI) [M + H]+ | Retention Time (minutes) |
|---|---|---|---|---|---|---|---|
| 61 | Cl | F | Cl | —CH$_2$S(O)$_2$CH$_3$ | H | 594 | nt |
| 62 | Cl | F | Cl | cyclopropyl | H | nt | nt |
| 63 | Cl | Cl | CF$_3$ | —CH$_2$S(O)$_2$CH$_3$ | H | 644 | nt |
| 64 | Cl | Cl | Cl | —CH$_2$S(O)$_2$CH$_3$ | H | 610 | nt |
| 65 | Cl | H | CF$_3$ | —CH$_2$S(O)$_2$CH$_3$ | H | 610 | nt |
| 66 | Cl | Br | Cl | —CH$_2$S(O)$_2$CH$_3$ | H | 656 | nt |
| 67 | Cl | H | Cl | —CH$_2$S(O)$_2$CH$_3$ | H | nt | nt |
| 68 | Cl | F | Cl | 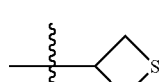 | H | nt | nt |
| 69 | Cl | F | Cl | 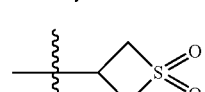 | H | 606 | 6.00 |
| 70 | CF$_3$ | H | CF$_3$ | cyclopropyl | H | 592 | nt |
| 71 | CF$_3$ | H | Cl | cyclopropyl | H | 558 | nt |
| 72 | Cl | Br | Cl | cyclopropyl | H | 604 | nt |
| 73 | Cl | Cl | Cl | —CH$_2$S(O)$_2$CH$_3$ | methyl | 624 | nt |
| 74 | Cl | F | Cl | —CH$_2$S(O)$_2$CH$_3$ | methyl | 608 | nt |
| 75 | Cl | Cl | Cl | cyclopropyl | methyl | 572 | nt | nt—not tested.

5'-(5-(3,5-dichlorophenyl)-5-(trifluoromethyl)-4,5-dihydroisoxazol-3-yl)-1-(2-(methylsulfonyl)acetyl)spiro[azetidine-3,1'-isoindolin]-3'-one (67);

5'-(5-(3,5-dichloro-4-fluorophenyl)-5-(trifluoromethyl)-4,5-dihydroisoxazol-3-yl)-1-(thietane-3-carbonyl)spiro[azetidine-3,1'-isoindolin]-3'-one (68);

5'-(5-(3,5-dichloro-4-fluorophenyl)-5-(trifluoromethyl)-4,5-dihydroisoxazol-3-yl)-1-(1,1-dioxidothietane-3-carbonyl)spiro[azetidine-3,1'-isoindolin]-3'-one (69);

5'-(5-(3,5-bis(trifluoromethyl)phenyl)-5-(trifluoromethyl)-4,5-dihydroisoxazol-3-yl)-1-(cyclopropanecarbonyl)spiro[azetidine-3,1'-isoindolin]-3'-one (70);

5'-(5-(3-chloro-5-(trifluoromethyl)phenyl)-5-(trifluoromethyl)-4,5-dihydroisoxazol-3-yl)-1-(cyclopropanecarbonyl)spiro[azetidine-3,1'-isoindolin]-3'-one (71);

5'-(5-(4-bromo-3,5-dichlorophenyl)-5-(trifluoromethyl)-4,5-dihydroisoxazol-3-yl)-1-(cyclopropanecarbonyl)spiro[azetidine-3,1'-isoindolin]-3'-one (72);

2'-methyl-1-(2-(methylsulfonyl)acetyl)-5'-(5-(3,4,5-trichlorophenyl)-5-(trifluoromethyl)-4,5-dihydroisoxazol-3-yl)spiro[azetidine-3,1'-isoindolin]-3'-one (73);

5-(5-(3,5-dichloro-4-fluorophenyl)-5-(trifluoromethyl)-4,5-dihydroisoxazol-3-yl)-2'-methyl-1-(2-(methylsulfonyl)acetyl)spiro[azetidine-3,1'-isoindolin]-3'-one (74); and 1-(cyclopropanecarbonyl)-2'-methyl-5'-(5-(3,4,5-trichlorophenyl)-5-(trifluoromethyl)-4,5-dihydroisoxazol-3-yl)spiro[azetidine-3,1'-isoindolin]-3'-one (75).

Additional NMR data is provided for specific Examples in Table 4.

TABLE 4

NMR Data Obtained for Specific Examples

| Example No. | 1H NMR |
|---|---|
| 9, 48, 48^a, and 48^b | (CDCl3) δ ppm: 7.67-7.60 (5H), 5.19 (2H) 4.72-4.67 (2H), 4.47-4.48 (1H), 4.37-4.38 (1H), 4.13-4.10 (1H), 3.93-3.88 (2H), 3.74-3.71 (1H), 3.23 (3H) |
| 53 | (CDCl$_3$) δ ppm: 8.10 (2H), 8.00 (1H), 7.70-7.62 (3H), 5.19 (2H), 4.69 (2H), 4.47 (1H), 4.39 (1H), 4.23 (1H), 3.89 (2H), 3.78 (1H), 3.22 (3H) |
| 54 | (CDCl$_3$) δ ppm: 7.68-7.58 (6H), 5.19 (2H), 4.69 (2H), 4.47 (1H), 4.39 (1H), 4.11 (1H), 3.89 (2H), 3.73 (1H), 3.22 (3H) |
| 55 | (CDCl$_3$) δ ppm: 8.15 (2H), 7.69-7.62 (3H), 5.19 (2H), 4.69 (2H), 4.47 (1H), 4.38 (1H), 4.21 (1H), 3.89 (2H), 3.75 (1H), 3.22 (3H) |
| 56 | (CDCl$_3$) δ ppm: 7.68-7.60 (3H), 7.43 (1H), 7.30 (1H), 7.20 (1H), 5.19 (2H), 4.68 (2H), 4.47 (1H), 4.37 (1H), 4.10 (1H), 3.89 (2H), 3.72 (1H), 3.22 (3H) |
| 57 | (CDCl$_3$) δ ppm: 7.71-7.60 (4H), 7.50 (1H), 7.25 (1H), 5.19 (2H), 4.68 (2H), 4.47 (1H), 4.36 (1H), 4.11 (1H), 3.89 (2H), 3.74 (1H), 3.22 (3H) |
| 58 | (CDCl$_3$) δ ppm: 7.89 (1H), 7.86 (1H), 7.67-7.60 (5H), 5.19 (2H), 4.68 (2H), 4.47 (1H), 4.40 (1H), 4.16 (1H), 3.89 (2H), 3.78 (1H), 3.22 (3H) |
| 59 | (CDCl$_3$) δ ppm: 8.19 (1H), 7.98 (1H), 7.89 (1H), 7.62 (2H), 7.50 (1H), 4.83 (2H), 4.55 (2H), 4.17 (1H), 3.95 (2H), 3.81 (1H), 3.24 (3H) |
| 61 | (CDCl$_3$) δ ppm: 8.20 (1H), 7.98 (2H), 7.88 (2H), 7.47 (1H), 4.83 (2H), 4.55 (2H), 4.22 (1H), 3.95 (2H), 3.83 (1H), 3.24 (3H) |
| 62 | (CDCl$_3$) δ ppm: 8.19 (1H), 7.98 (1H), 7.88 (1H), 7.69 (2H), 7.63 (1H), 4.83 (2H), 4.55 (2H), 4.17 (1H), 3.95 (2H), 3.81 (1H), 3.24 (3H) |
| 63 | (CDCl$_3$) δ ppm: 8.21 (1H), 7.99 (1H), 7.89-7.86 (2H), 7.80 (1H), 7.72 (1H), 7.53 (1H), 4.83 (2H), 4.55 (2H), 4.22 (1H), 3.95 (2H), 3.85 (1H), 3.24 (3H) |
| 67 | (d$_6$-DMSO) δ ppm: 3.4-3.7 (m, 2H), 4.2-4.7 (m, 9H), 7.8-7.9 (m, 2H), 7.95 (s, 1H), 8.1 (2H), 9.3 (s, 1H). This nmr is on my CeN, 00110163-1240-002. |
| 68 | (CDCl$_3$) δ ppm: 8.24 (1H), 8.13 (2H), 8.00 (1H), 7.88 (1H), 7.54 (1H) 4.90-4.39 (4H), 4.29 (1H), 3.90 (1H), 1.56 (1H), 1.12 (2H), 0.93 (2H) |

TABLE 4-continued

NMR Data Obtained for Specific Examples

| Example No. | 1H NMR |
|---|---|
| 69 | (CDCl$_3$) δ ppm: 8.23 (1H), 7.99 (1H), 7.86 (2H), 7.80 (1H), 7.72 (1H), 7.54 (1H) 4.85-4.40 (4H), 4.23 (1H), 3.87 (1H), 1.54 (1H), 1.11 (2H), 0.91 (2H) |
| 70 | (CDCl$_3$) δ ppm: 8.21 (1H), 7.97 (1H), 7.86 (1H), 7.67 (2H), 7.59 (1H) 4.80-4.40 (4H), 4.17 (1H), 3.82 (1H), 1.52 (1H), 1.10 (2H), 0.90 (2H) |
| 71 | (CDCl$_3$) δ ppm: 8.16 (1H), 7.95 (1H), 7.88 (1H), 7.67 (2H), 4.85 (1H), 4.75 (1H), 4.57 (1H), 4.44 (1H), 4.15 (1H), 3.95 (2H), 3.77 (1H), 3.27 (3H), 3.24 (3H) |
| 72 | (CDCl$_3$) δ ppm: 8.16 (1H), 7.95 (1H), 7.88 (1H), 7.61 (2H), 4.87 (1H), 4.75 (1H), 4.58 (1H), 4.45 (1H), 4.15 (1H), 3.95 (2H), 3.77 (1H), 3.27 (3H), 3.24 (3H) |
| 73 | (CDCl$_3$) δ ppm: 8.17 (1H), 7.95 (1H), 7.85 (1H), 7.67 (2H), 4.72 (1H), 4.57-4.50 (2H), 4.38 (1H), 4.16 (1H), 3.78 (1H), 3.27 (3H), 1.53 (1H), 1.11 (2H), 0.92 (2H) |

Biological Assays

The biological activity of the compounds of the present invention can be tested against hard tick larvae, soft ticks, fleas, and horn flies using the test methods described below.

Flea (*Ctenocephalides felis*) Membrane Feed Assay-Adult

Formula (1) compounds were dissolved in DMSO and aliquots added to citrated bovine blood in a membrane covered Petri dish pre-warmed to 37° C. Feeding tubes containing approximately 30-35 adult fleas were placed onto the Petri dishes. The fleas were allowed to feed for approximately 2 hours. Fleas were observed for knockdown and/or death at approximately 2 and 24 hours. Endpoint data were recorded as a lethal dose 80% ($LD^{80}$) in μg/mL. In this assay, Examples 1-3,5,9,13, 20, 21, 27-30, 35, 37, 42-43, 45-46, 48, 49a, 52, and 54-60 had an $LD^{80} \leq 1$ μg/mL; Examples 8, 10-11, 36, 48b, 51, and 53 had an $LD^{80} \leq 3$ μg/mL; Examples 14-19 and 25 had an $LD^{80} \leq 30$ μg/mL; and Examples 61-64 had an $LD^{80} \leq 100$ μg/mL.

Soft Tick (*Ornithidorus turicata*) Blood Feed Assay

Formula (1) compounds were dissolved in dimethylsulfoxide (DMSO) and aliquots added to citrated bovine blood in a membrane covered Petri dish. The Petri dish was placed on a warming tray. Approximately 5 nymph stage ticks were placed onto the membrane, covered, and left to feed. Fed ticks were removed and placed into a Petri dish with sand. Fed ticks were observed at approximately 24, 48 and 72 hours for paralysis and/or death. Endpoint data was recorded as an $ED^{100}$ and/or an $LD^{100}$ in μg/mL. Positive control was fipronil and DMSO was used as the negative control. In this assay, Examples 5, 9, 29, 35, 49a, and 51-59 had an $LD^{100} \leq 0.01$ μg/mL; Examples 3, 13, 21, 28, 30, 36-37, 42-43, 45-46, 48, 50, and 60 had an $LD^{100} \leq 0.03$ μg/mL; and Examples 1-2, 11, and 27 had an $LD^{100} \leq 0.1$ μg/mL.

Horn Fly (*Haematobia irritans*) Feed Assay

Formula (1) compounds were dissolved in DMSO and aliquots added to citrated bovine blood in a membrane covered Petri dish. Approximately ten horn flies were placed onto each Petri dish and covered. The flies were then allowed to feed on the treated blood cell. Flies were held at approximately 80° F. with a minimum of approximately 50% relative humidity. Flies were examined for knockdown and mortality at approximately 2 and 24 hours. Endpoint data was recorded as a lethal dose 90% ($LD^{90}$) in μg/mL. In this assay, Examples 9, 35, 37, and 49a had an $LD^{90}$ of $\leq 0.3$ μg/mL; Examples 2, 29, 30, 45, 46, and 48 had an $LD^{90}$ of $\leq 1$ μg/mL; and Examples 1, 3, 5, 42, and 43 had an $LD^{90}$ of $\leq 3$ μg/mL.

We claim:

1. A compound of Formula (V.1) or Formula (V.2)

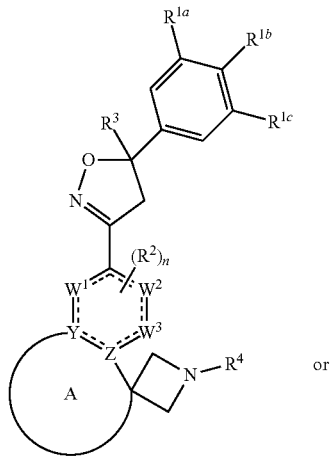

(V.1)

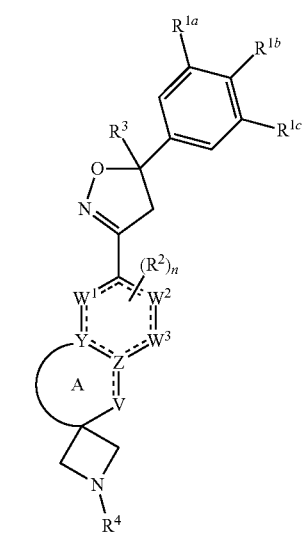

(V.2)

wherein

Y and Z are each independently C or N;

$W^1$, $W^2$, and $W^3$ are each independently C or N;

V is C, N, O, or S;

A taken together with Y and Z or V, Y, and Z is a 5- to 7-membered partially saturated or saturated carbocyclic or heterocyclic ring where the heterocyclic ring contains at least 1 to 3 heteroatoms selected from N, O, or S, and where ring A is optionally substituted with at least one substituent selected from oxo, =S, =$NR^7$, halo, hydroxyl, cyano, $C_1$-$C_6$alkyl, $C_1$-$C_6$haloalkyl, and $C_1$-$C_6$alkoxy;

$R^{1a}$, $R^{1b}$, and $R^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$ cycloalkyl, $C_1$-$C_6$haloalkoxy, —C(O)$NH_2$, —$SF_5$, or —S(O)$_p$R;

$R^2$ is halo, cyano, $C_1$-$C_6$alkyl, $C_1$-$C_6$haloalkyl, nitro, hydroxyl, —C(O)$NR^aR^b$, $C_2$-$C_6$alkenyl, $C_2$-$C_6$alkynyl, —S(O)$_p$R, or —OR;

$R^3$ is cyano, $C_1$-$C_6$alkyl, $C_1$-$C_6$haloalkyl, —C(O)$NR^aR^b$, $C_2$-$C_6$alkenyl, $C_2$-$C_6$alkynyl, $C_2$-$C_6$haloalkenyl, or $C_2$-$C_6$haloalkynyl;

$R^4$ is hydrogen, $C_1$-$C_6$alkyl, $C_0$-$C_6$alkyl$C_3$-$C_6$cycloalkyl, —C(O)$R^5$, —C(S)$R^5$, —C(O)$NR^aR^5$, —C(O)C(O)$NR^aR^5$, —S(O)$_p R^c$, —S(O)$_2NR^aR^5$, —C($NR^7$)$R^5$, —C($NR^7$)$NR^aR^5$, $C_0$-$C_6$alkylphenyl, $C_0$-$C_6$alkylheteroaryl, or $C_0$-$C_6$alkylheterocycle;

$R^5$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;

$R^6$ is hydrogen, $C_1$-$C_6$alkyl, hydroxyl, or $C_1$-$C_6$alkoxy;

$R^7$ is hydrogen, $C_1$-$C_6$alkyl, hydroxyl, cyano, nitro, —S(O)$_p R^c$, or $C_1$-$C_6$alkoxy;

R is $C_1$-$C_6$alkyl or $C_3$-$C_6$cycloalkyl optionally substituted with at least one halo substituent;

$R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

$R^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p NR^aR^b$, —$NR^aR^b$, —$NR^aC(O)R^b$, —SC(O)R, —SCN, or —C(O)$NR^aR^b$;

each of $R^4$ and $R^5$ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, —S(O)$_p R^c$, —SH, —S(O)$_p N R^aR^b$, —$NR^aR^b$, —$NR^aC(O)R^b$, —SC(O)R, —SCN, or —C(O)$NR^aR^b$; and wherein each of $R^4$ and $R^5$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =$NR^7$, hydroxyl, $C_1$-$C_6$alkoxy, hydroxyl$C_1$-$C_6$alkyl-, $C_1$-$C_6$alkyl, $C_1$-$C_6$haloalkyl, —SH, —S(O)$_p$R, and $C_1$-$C_6$haloalkoxy;

n is the integer 0, 1, or 2, and when n is 2, each $R^2$ may be identical or different from each other;

p is the integer 0, 1, or 2; and

---- is a single or double bond;

stereoisomers thereof, and veterinarily acceptable salts thereof.

2. A pharmaceutical or veterinary composition comprising a therapeutic amount of a compound of Formula (V.1) or (Formula V.2) of claim 1.

3. The compound of Formula (V.1) of claim 1 having Formula (V.1.1)

(V.1.1)

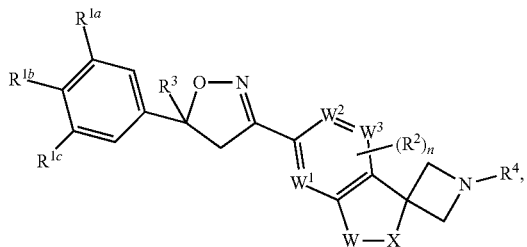

wherein
W¹, W², and W³ are each independently C or N;
X and W are each independently O, S, NR⁶, —CH₂—, —C(O)—, —C(NR⁷)—, or —C(S)—, when X is O, S, or NR⁶, then W is —CH₂—, —C(O)—, —C(NR⁷)—, or —C(S)—, and when W is O, S, or NR⁶, then X is —CH₂—, —C(O)—, —C(NR⁷)—, or —C(S)—,
$R^{1a}$, $R^{1b}$, and $R^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$ cycloalkyl, $C_1$-$C_6$haloalkoxy, —C(O)NH₂, —SF₅, or —S(O)$_p$R;
R² is halo, cyano, $C_1$-$C_6$alkyl, $C_1$-$C_6$haloalkyl, nitro, hydroxyl, —C(O)NR$^a$R$^b$, $C_2$-$C_6$alkenyl, $C_2$-$C_6$alkynyl, —S(O)$_p$R, or —OR;
R³ is cyano, $C_1$-$C_6$alkyl, $C_1$-$C_6$haloalkyl, —C(O)NR$^a$R$^b$, $C_2$-$C_6$alkenyl, $C_2$-$C_6$alkynyl, $C_2$-$C_6$haloalkenyl, or $C_2$-$C_6$haloalkynyl;
R⁴ is hydrogen, $C_1$-$C_6$alkyl, $C_0$-$C_6$alkyl$C_3$-$C_6$cycloalkyl, —C(O)R⁵, —C(S)R⁵, —C(O)NR$^a$R⁵, —C(O)C(O)NR$^a$R⁵, —S(O)$_p$R$^c$, —S(O)₂NR$^a$R⁵, —C(NR⁷)R⁵, —C(NR⁷)NR$^a$R⁵, $C_0$-$C_6$alkylphenyl, $C_0$-$C_6$alkylheteroaryl, or $C_0$-$C_6$alkylheterocycle;
R⁵ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;
R⁶ is hydrogen, $C_1$-$C_6$alkyl, hydroxyl, or $C_1$-$C_6$alkoxy;
R⁷ is hydrogen, $C_1$-$C_6$alkyl, hydroxyl, cyano, nitro, —S(O)$_p$R$^c$, or $C_1$-$C_6$alkoxy;
R is $C_1$-$C_6$alkyl or $C_3$-$C_6$cycloalkyl optionally substituted with at least one halo substituent;
R$^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;
R$^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;
R$^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, —S(O)$_p$R, —SH, —S(O)$_p$NR$^a$R$^b$, —NR$^a$R$^b$, —NR$^a$C(O)R$^b$, —SC(O)R, —SCN, or —C(O)NR$^a$R$^b$;
each of R⁴ and R⁵ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, —S(O)$_p$R$^c$, —SH, —S(O)$_p$NR$^a$R$^b$, —NR$^a$R$^b$, —NR$^a$C(O)R$^b$, —SC(O)R, —SCN, or —C(O)NR$^a$R$^b$; and
wherein each of R⁴ and R⁵ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =NR⁷, hydroxyl, $C_1$-$C_6$alkoxy, hydroxyl$C_1$-$C_6$alkyl-, $C_1$-$C_6$alkyl, $C_1$-$C_6$haloalkyl, —SH, —S(O)$_p$R, and $C_1$-$C_6$haloalkoxy;
n is the integer 0, 1, or 2, and when n is 2, each R² may be identical or different from each other; and
p is the integer 0, 1, or 2,
stereoisomers thereof, and veterinary acceptable salts thereof.

4. The compound of claim 3 wherein W¹ is N and W² and W³ are each C, or W² is N and W¹ and W³ are each C, or W³ is N and W¹ and W² are each C; and n is the integer 0, 1, or 2, stereoisomers thereof, and veterinary acceptable salts thereof.

5. A pharmaceutical or veterinary composition comprising a therapeutic amount of a compound of Formula (V.1.1) of claim 3.

6. A compound of Formula (1)

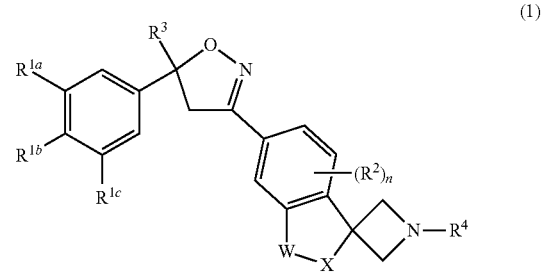

(1)

wherein
X and W are each independently O, S, NR⁶, —CH₂—, —C(O)—, —C(NR⁷)—, or —C(S)—, when X is O, S, or NR⁶, then W is —CH₂—, —C(O)—, —C(NR⁷)—, or —C(S)—, and when W is O, S, or NR⁶, then X is —CH₂—, —C(O)—, —C(NR⁷)—, or —C(S)—,
$R^{1a}$, $R^{1b}$, and $R^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$ cycloalkyl, $C_1$-$C_6$haloalkoxy, —C(O)NH₂, —SF₅, or —S(O)$_p$R;
R² is halo, cyano, $C_1$-$C_6$alkyl, $C_1$-$C_6$haloalkyl, nitro, hydroxyl, —C(O)NR$^a$R$^b$, $C_2$-$C_6$alkenyl, $C_2$-$C_6$alkynyl, —S(O)$_p$R, or —OR;
R³ is cyano, $C_1$-$C_6$alkyl, $C_1$-$C_6$haloalkyl, —C(O)NR$^a$R$^b$, $C_2$-$C_6$alkenyl, $C_2$-$C_6$alkynyl, $C_2$-$C_6$haloalkenyl, or $C_2$-$C_6$haloalkynyl;
R⁴ is hydrogen, $C_1$-$C_6$alkyl, $C_0$-$C_6$alkyl$C_3$-$C_6$cycloalkyl, —C(O)R⁵, —C(S)R⁵, —C(O)NR$^a$R⁵, —C(O)C(O)NR$^a$R⁵, —S(O)$_p$R$^c$, —S(O)₂NR$^a$R⁵, —C(NR⁷)R⁵, —C(NR⁷)NR$^a$R⁵, $C_0$-$C_6$alkylphenyl, $C_0$-$C_6$alkylheteroaryl, or $C_0$-$C_6$alkylheterocycle;
R⁵ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;
R⁶ is hydrogen, $C_1$-$C_6$alkyl, hydroxyl, or $C_1$-$C_6$alkoxy;
R⁷ is hydrogen, $C_1$-$C_6$alkyl, hydroxyl, cyano, nitro, —S(O)$_p$R$^c$, or $C_1$-$C_6$alkoxy;
R is $C_1$-$C_6$alkyl or $C_3$-$C_6$cycloalkyl optionally substituted with at least one halo substituent;

$R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

$R^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R, —SCN, or —C(O)NR$^a$R$^b$;

each of $R^4$ and $R^5$ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, —S(O)$_p$R$^c$, —SH, —S(O)$_p$NR$^a$R$^b$, —NR$^a$R$^b$, —NR$^a$C(O)R$^b$, —SC(O)R, —SCN, or —C(O)NR$^a$R$^b$; and wherein each of $R^4$ and $R^5$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =NR$^7$, hydroxyl, $C_1$-$C_6$alkoxy, hydroxyl$C_1$-$C_6$alkyl-, $C_1$-$C_6$alkyl, $C_1$-$C_6$haloalkyl, —SH, —S(O)$_p$R, and $C_1$-$C_6$haloalkoxy;

n is the integer 0, 1, or 2, and when n is 2, each $R^2$ may be identical or different from each other; and p is the integer 0, 1, or 2;

stereoisomers thereof, and veterinarily acceptable salts thereof.

7. The compound of claim 6 wherein X is —O— and W is —C(O)—, or X is —O— and W is —CH$_2$—, or X is —NR$^6$— and W is —C(O)—, or W is —O— and X is —C(O)—, or W is —O— and X is —CH$_2$—, or W is —NR$^6$— and X is —C(O)—; and wherein $R^{1a}$, $R^{1b}$, and $R^{1c}$ are each independently hydrogen, halo, or $C_1$-$C_6$haloalkyl;

$R^3$ is $C_1$-$C_6$haloalkyl;

$R^4$ is —C(O)R$^5$; and n is the integer 0;

stereoisomers thereof, and veterinarily acceptable salts thereof.

8. The compound of claim 7 wherein X is —O— and W is —C(O)—, or W is —O— and X is —C(O)—; and wherein $R^{1a}$, $R^{1b}$, and $R^{1c}$ are each independently hydrogen, halo, or $C_1$-$C_6$haloalkyl;

$R^3$ is —CF$_3$; and $R^4$ is —C(O)R$^5$;

stereoisomers thereof, and veterinarily acceptable salts thereof.

9. The compound of claim 8 wherein X is —O— and W is —C(O)—;

$R^5$ is $C_1$-$C_6$alkyl, $C_0$-$C_6$alkyl$C_3$-$C_6$cycloalkyl, $C_0$-$C_6$alkylheteroaryl, or $C_0$-$C_6$alkylheterocycle;

wherein each of $R^5$ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, —S(O)$_p$R$^c$, —SH, —S(O)$_p$NR$^a$R$^b$, —NR$^a$R$^b$, —NR$^a$C(O)R$^b$, —SC(O)R, —SCN, or —C(O)NR$^a$R$^b$; and wherein each of $R^5$ $C_0$-$C_6$alkylheteroaryl or $C_0$-$C_6$alkylheterocycle moiety can be further optionally substituted with at least one substituent selected from cyano, halo, oxo, =S, =NR$^7$, hydroxyl, $C_1$-$C_6$alkoxy, $C_1$-$C_6$alkyl, $C_1$-$C_6$haloalkyl, hydroxyl$C_1$-$C_6$alkyl-, —SH, —S(O)$_p$R, and $C_1$-$C_6$haloalkoxy;

stereoisomers thereof, and veterinarily acceptable salts thereof.

10. The compound of claim 7 wherein X is —O— and W is —CH$_2$— or W is —O— and X is —CH$_2$—; and wherein $R^{1a}$, $R^{1b}$ and $R^{1c}$ are each independently hydrogen, halo, or $C_1$-$C_6$haloalkyl;

$R^3$ is —CF$_3$; and $R^4$ is —C(O)R$^5$;

stereoisomers thereof, and veterinarily acceptable salts thereof.

11. The compound of claim 10 wherein X is —O— and W is —CH$_2$—; and wherein $R^5$ is $C_1$-$C_6$alkyl, $C_0$-$C_6$alkyl$C_3$-$C_6$cycloalkyl, $C_0$-$C_6$alkylheteroaryl, or $C_0$-$C_6$alkylheterocycle;

wherein each of $R^5$ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, —S(O)$_p$R$^c$, —SH, —S(O)$_p$NR$^a$R$^b$, —NR$^a$R$^b$, —NR$^a$C(O)R$^b$, —SC(O)R, —SCN, or —C(O)NR$^a$R$^b$; and wherein each of $R^5$ $C_0$-$C_6$alkylheteroaryl or $C_0$-$C_6$alkylheterocycle moiety can be further optionally substituted with at least one substituent selected from cyano, halo, oxo, =S, =NR$^7$, hydroxyl, $C_1$-$C_6$alkoxy, $C_1$-$C_6$alkyl, $C_1$-$C_6$haloalkyl, hydroxyl$C_1$-$C_6$alkyl-, —SH, —S(O)$_p$R, and $C_1$-$C_6$haloalkoxy;

stereoisomers thereof, and veterinarily acceptable salts thereof.

12. A compound selected from the group consisting of:

1-(cyclopropanecarbonyl)-5'-(3,4,5-trichlorophenyl)-5-(trifluoromethyl)-4,5-dihydroisoxazol-3-yl)-3'H-spiro{azetidine-3,1'-isobenzofuran}-3'-one;

5'-(5-(3,5-dichloro-4-fluorophenyl)-5-(trifluoromethyl)-4,5-dihydroisoxazol-3-yl)-1-propionyl-3'H-spiro[azetidine-3,1-isobenzofuran]-3'-one;

1-(cyclopropanecarbonyl)-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(3-methylbutanoyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2-hydroxy-2-methylpropanoyl)-3'H-spiro[azetidine-3,1'-isobenzofuran]-3'-one;

1-(2-cyclopropylacetyl)-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

1-acetyl-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(1-hydroxycyclopropanecarbonyl)-3'H-spiro[azetidine-3,1'-isobenzofuran]-3'-one;

1-(cyclobutanecarbonyl)-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-pivaloyl-3'H-spiro[azetidine-3,1-isobenzofuran]-3'-one;

5'-(5-(3,5-dichloro-4-fluorophenyl)-5-(trifluoromethyl)-4,5-dihydroisoxazol-3-yl)-1-(2-hydroxyacetyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2-(1-hydroxycyclopropyl)acetyl)-3'H-spiro[azetidine-3,1'-isobenzofuran]-3'-one;

1-butyryl-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2-(methylthio)acetyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2-(methylsulfinyl)acetyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2-(methylsulfonyl)acetyl)-3'H-spiro[azetidine-3,1'-isobenzofuran]-3'-one;

1-(2-(1H-pyrazol-1-yl)acetyl)-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(1-(trifluoromethyl)cyclopropanecarbonyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-isobutyryl-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2-(3-methyl-1H-pyrazol-1-yl)acetyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(3-hydroxy-2-methylpropanoyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(2,2-difluorocyclopropanecarbonyl)-3'H-spiro[azetidine-3,1'-isobenzofuran]-3'-one;

5'-(5-(3,5-dichloro-4-fluorophenyl)-5-(trifluoromethyl)-4,5-dihydroisoxazol-3-yl)-1-(4,4,4-trifluorobutanoyl)-3'H-spiro[azetidine-3,1'-isobenzofuran]-3'-one;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-((trifluoromethyl)thio)ethanone;

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1-oxidothietan-3-yl)methanone;

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;

(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;

(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;

(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;

(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-methylpropan-1-one;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-hydroxyethanone;

cyclobutyl(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)methanone;

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1-hydroxycyclopropyl)methanone;

N-(2-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-oxoethyl)formamide;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)propan-1-one;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-hydroxy-2-methylpropan-1-one;

2-cyclopropyl-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2,2-dimethylpropan-1-one;

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1-(trifluoromethyl)cyclopropyl)methanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-3-hydroxy-2-methylpropan-1-one;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(3-methyl-1H-pyrazol-1-yl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-3-methylbutan-1-one;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(1H-pyrazol-1-yl)ethanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-3-hydroxybutan-1-one;

cyclopropyl(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)methanone;

1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1yl-)butan-1-one;

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(thietan-3-yl)methanone;

(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;

(R)-(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;

(S)-(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;

2-(methylsulfonyl)-1-(5'-(5-(3,4,5-trichlorophenyl)-5-(trifluoromethyl)-4,5-dihydroisoxazol-3-yl)-3'H-spiro[azetidine-3,1'-isobenzofuran]-1-yl)ethanone;

1-(5'-(5-(3,5-dichlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3-chloro-5-(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3,4-dichloro-5-(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(4-bromo-3,5-dichlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(R)-1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(S)-1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3-bromo-5-chlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(4-chloro-3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3-chloro-5-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(R)-1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

(S)-1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;

2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone;

(R)-2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone;

(S)-2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone;

5'-(5-(3,5-bis(trifluoromethyl)phenyl)-5-(trifluoromethyl)-4,5-dihydroisoxazol-3-yl)-1-(2-(methylsulfonyl)acetyl)spiro[azetidine-3,1'-isoindolin]-3'-one;

5'-(5-(3,5-dichloro-4-fluorophenyl)-5-(trifluoromethyl)-4,5-dihydroisoxazol-3-yl)-1-(2-(methylsulfonyl)acetyl)spiro[azetidine-3,1'-isoindolin]-3'-one;

1-(cyclopropanecarbonyl)-5'-(5-(3,5-dichloro-4-fluorophenyl)-5-(trifluoromethyl)-4,5-dihydroisoxazol-3-yl)spiro[azetidine-3,1'-isoindolin]-3'-one;

5'-(5-(3,4-dichloro-5-(trifluoromethyl)phenyl)-5-(trifluoromethyl)-4,5-dihydroisoxazol-3-yl)-1-(2-(methylsulfonyl)acetyl)spiro[azetidine-3,1'-isoindolin]-3'-one;

1-(2-(methylsulfonyl)acetyl)-5'-(5-(3,4,5-trichlorophenyl)-5-(trifluoromethyl)-4,5-dihydroisoxazol-3-yl)spiro[azetidine-3,1'-isoindolin]3'-one;

5'-(5-(3-chloro-5-(trifluoromethyl)phenyl)-5-(trifluoromethyl)-4,5-dihydroisoxazol-3-yl)-1-(2-(methylsulfonyl)acetyl)spiro[azetidine-3,1'-isoindolin]-3'-one;

5'-(5-(4-bromo-3,5-dichlorophenyl)-5-(trifluoromethyl)-4,5-dihydroisoxazol-3-yl)-1-(2-(methylsulfonyl)acetyl)spiro[azetidine-3,1'-isoindolin]-3'-one;

5'-(5-(3,5-dichlorophenyl)-5-(trifluoromethyl)-4,5-dihydroisoxazol-3-yl)-1-(2-(methylsulfonyl)acetyl)spiro[azetidine-3,1'-isoindolin]-3'-one;

5'-(5-(3,5-dichloro-4-fluorophenyl)-5-(trifluoromethyl)-4,5-dihydroisoxazol-3-yl)-1-(thietane-3-carbonyl)spiro[azetidine-3,1'-isoindolin]-3'-one;

5'-(5-(3,5-dichloro-4-fluorophenyl)-5-(trifluoromethyl)-4,5-dihydroisoxazol-3-yl)-1-(1,1-dioxidothietane-3-carbonyl)spiro[azetidine-3,1'-isoindolin]-3'-one;

5'-(5-(3,5-bis(trifluoromethyl)phenyl)-5-(trifluoromethyl)-4,5-dihydroisoxazol-3-yl)-1-(cyclopropanecarbonyl)spiro[azetidine-3,1'-isoindolin]-3'-one;

5'-(5-(3-chloro-5-(trifluoromethyl)phenyl)-5-(trifluoromethyl)-4,5-dihydroisoxazol-3-yl)-1-(cyclopropanecarbonyl)spiro[azetidine-3,1'-isoindolin]-3'-one;

5'-(5-(4-bromo-3,5-dichlorophenyl)-5-(trifluoromethyl)-4,5-dihydroisoxazol-3-yl)-1-(cyclopropanecarbonyl)spiro[azetidine-3,1'-isoindolin]-3'-one;

2'-methyl-1-(2-(methylsulfonyl)acetyl)-5'-(5-(3,4,5-trichlorophenyl)-5-(trifluoromethyl)-4,5-dihydroisoxazol-3-yl)spiro[azetidine-3,1'-isoindolin]-3'-one;

5'-(5-(3,5-dichloro-4-fluorophenyl)-5-(trifluoromethyl)-4,5-dihydroisoxazol-3-yl)-2'-methyl-1-(2-(methylsulfonyl)acetyl)spiro[azetidine-3,1'-isoindolin]-3'-one; and 1-(cyclopropanecarbonyl)-2'-methyl-5'-(5-(3,4,5-trichlorophenyl)-5-(trifluoromethyl)-4,5-dihydroisoxazol-3-yl)spiro[azetidine-3,1'-isoindolin]-3'-one, or
a stereoisomer thereof, or a veterinarily acceptable salt thereof.

13. A compound of claim 12 selected from the group consisting of:
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-((trifluoromethyl)thio)ethanone;
(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1-oxidothietan-3-yl)methanone;
(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;
(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;
(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;
(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;
(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-methylpropan-1-one;
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-hydroxyethanone;
cyclobutyl(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)methanone;
(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1-hydroxycyclopropyl)methanone;
N-(2-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-oxoethyl)formamide;
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)ethanone;
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)propan-1-one;
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-hydroxy-2-methylpropan-1-one;
2-cyclopropyl-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)ethanone;
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2,2-dimethylpropan-1-one;
(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1-(trifluoromethyl)cyclopropyl)methanone;
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-3-hydroxy-2-methylpropan-1-one;
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(3-methyl-1H-pyrazol-1-yl)ethanone;
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-3-methylbutan-1-one;
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(1H-pyrazol-1-yl)ethanone;
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-3-hydroxybutan-1-one;
cyclopropyl(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)methanone;
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)butan-1-one;
(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(thietan-3-yl)methanone;
(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;
(R)-(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;
(S)-(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;
2-(methylsulfonyl)-1-(5'-(5-(3,4,5-trichlorophenyl)-5-(trifluoromethyl)-4,5-dihydroisoxazol-3-yl)-3'H-spiro[azetidine-3,1'-isobenzofuran]-1-yl)ethanone;
1-(5'-(5-(3,5-dichlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
1-(5'-(5-(3-chloro-5-(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;
1-(5'-(5-(3,4-dichloro-5-(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;

1-(5'-(5-(4-bromo-3,5-dichlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;
(R)-1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;
(S)-1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;
1-(5'-(5-(3-bromo-5-chlorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
1-(5'-(5-(4-chloro-3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;
1-(5'-(5-(3-chloro-5-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
(R)-1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
(S)-1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone;
(R)-2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone; and
(S)-2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone, or a stereoisomer thereof, or a veterinarily acceptable salt thereof.

14. The compound of claim 13 which is selected from:
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;
(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;
(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylthio)ethanone;
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;
(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;
(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfinyl)ethanone;
1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
(R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
(S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;
(R)-(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;
(S)-(5'-(5-(3,5-dichloro-4-fluorophenyl)-5-(trifluoromethyl)-4,5-dihydroisoxazol-3-yl)-2',3'-dihydrospiro[azetidine-3,1'-inden]-1-yl)(1,1-dioxidothietan-3-yl)methanone;
1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;
(R)-1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;
(S)-1-(5'-(5-(3,5-bis(trifluoromethyl)phenyl)-5-(trifluoromethyl)-4,5-dihydroisoxazol-3-yl)-3'H-spiro[azetidine-3,1'-isobenzofuran]-1-yl)-2-(methylsulfonyl)ethanone;
1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
(R)-1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
(S)-1-(5'-(5-(3-chloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone;
2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone;
(R)-2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone; and
(S)-2-(methylsulfonyl)-1-(5'-(5-(trifluoromethyl)-5-(3-(trifluoromethyl)phenyl)-4,5-dihydroisoxazol-3-yl)-3'H-spiro[azetidine-3,1'-isobenzofuran]-1-yl)ethanone, or a stereoisomer thereof, or a veterinarily acceptable salt thereof.

15. A veterinary composition comprising a compound of Formula 1

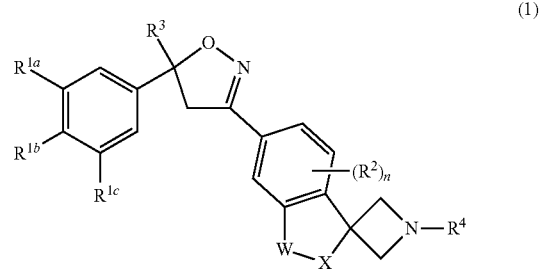

(1)

wherein
- X and W are each independently O, S, $NR^6$, —$CH_2$—, —C(O)—, —$C(NR^7)$—, or —C(S)—, when X is O, S, or $NR^6$, then W is —$CH_2$—, —C(O)—, —$C(NR^7)$—, or —C(S)—, and when W is O, S, or $NR^6$, then X is —$CH_2$—, —C(O)—, —$C(NR^7)$—, or —C(S)—;
- $R^{1a}$, $R^{1b}$, and $R^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$cycloalkyl, $C_1$-$C_6$haloalkoxy, —C(O)$NH_2$, —$SF_5$, or —$S(O)_pR$;
- $R^2$ is halo, cyano, $C_1$-$C_6$alkyl, $C_1$-$C_6$haloalkyl, nitro, hydroxyl, —C(O)$NR^aR^b$, $C_2$-$C_6$alkenyl, $C_2$-$C_6$alkynyl, —$S(O)_pR$, or —OR;
- $R^3$ is cyano, $C_1$-$C_6$alkyl, $C_1$-$C_6$haloalkyl, —C(O)$NR^aR^b$, $C_2$-$C_6$alkenyl, $C_2$-$C_6$alkynyl, $C_2$-$C_6$haloalkenyl, or $C_2$-$C_6$haloalkynyl;
- $R^4$ is hydrogen, $C_1$-$C_6$alkyl, $C_0$-$C_6$alkyl$C_3$-$C_6$cycloalkyl, —C(O)$R^5$, —C(S)$R^5$, —C(O)$NR^aR^5$, —C(O)C(O)$NR^aR^5$, —$S(O)_pR^c$, —$S(O)_2NR^aR^5$, —$C(NR^7)R^5$, —$C(NR^7)NR^aR^5$, $C_0$-$C_6$alkylphenyl, $C_0$-$C_6$alkylheteroaryl, or $C_0$-$C_6$alkylheterocycle;
- $R^5$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;
- $R^6$ is hydrogen, $C_1$-$C_6$alkyl, hydroxyl, or $C_1$-$C_6$alkoxy;
- $R^7$ is hydrogen, $C_1$-$C_6$alkyl, hydroxyl, cyano, nitro, —$S(O)_pR^c$, or $C_1$-$C_6$alkoxy;
- R is $C_1$-$C_6$alkyl or $C_3$-$C_6$cycloalkyl optionally substituted with at least one halo substituent;
- $R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;
- $R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —$S(O)_pR$;
- $R^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —$S(O)_pR$, —SH, —$S(O)_pNR^aR^b$, —$NR^aR^b$, —$NR^aC(O)R^b$, —SC(O)R, —SCN, or —C(O)$NR^aR^b$;
- each of $R^4$ and $R^5$ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, —$S(O)_pR^c$, —SH, —$S(O)_pN$-$R^aR^b$, —$NR^aR^b$, —$NR^aC(O)R^b$, —SC(O)R, —SCN, or —C(O)$NR^aR^b$; and
- wherein each of $R^4$ and $R^5$ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =$NR^7$, hydroxyl, hydroxyl$C_1$-$C_6$alkyl-, $C_1$-$C_6$alkoxy, $C_1$-$C_6$alkyl, $C_1$-$C_6$haloalkyl, —SH, —$S(O)_pR$, and $C_1$-$C_6$haloalkoxy;
- n is the integer 0, 1, or 2, and when n is 2, each $R^2$ may be identical or different from each other; and
- p is the integer 0, 1, or 2;

stereoisomers thereof, and veterinarily acceptable salts thereof.

16. The veterinary composition of claim 15 further comprising a veterinarily acceptable excipient, diluent, or carrier.

17. The veterinary composition of claim 16 further comprising at least one additional veterinary agent.

18. The veterinary composition of claim 17 wherein said additional veterinary agent is selected from the group consisting of consisting of abamectin, ivermectin, avermectin, moxidectin, emamectin, eprinomectin, selamectin, doramectin, nemadectin, albendazole, cambendazole, fenbendazole, flubendazole, mebendazole, oxfenbendazole, oxibendazole, parbendazole, tetramisole, levamisole, pyrantel pamoate, oxantel, morantel, indoxacarb, closantel, triclabendazole, clorsulon, refoxanide, niclosamide, praziquantel, epsiprantel, 2-desoxoparaherquamide, pyripole, pyrafluprole, lufenuron, spiromesifen, tebufenozide, spinosad, spinetoram, imidacloprid, dinotefuran, metaflumizone, thibendiamide, chlorantraniliprole, indoxacarb, pyridalyl, pyrimidifen, pyrifluquinazon, milbemycin oxime, milbemycin, demiditraz, amitraz, fipronil, methoprene, hydroprene, kinoprene, permethrin, and pyrethrin, or mixtures thereof.

19. A method for the treatment of a parasitic infection or infestation in an animal comprising administering to said animal in need of such treatment an effective amount of a compound of Formula 1

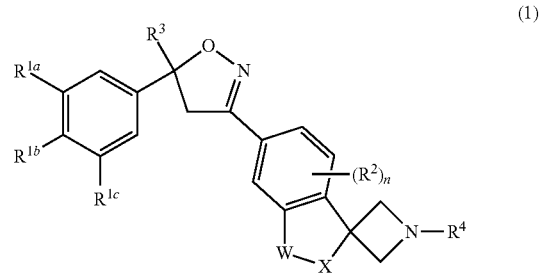

(1)

wherein
- X and W are each independently O, S, $NR^6$, —$CH_2$—, —C(O)—, —$C(NR^7)$—, or —C(S)—, when X is O, S, or $NR^6$, then W is —$CH_2$—, —C(O)—, —$C(NR^7)$—, or —C(S)—, and when W is O, S, or $NR^6$, then X is —$CH_2$—, —C(O)—, —$C(NR^7)$—, or —C(S)—;
- $R^{1a}$, $R^{1b}$, and $R^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$ cycloalkyl, $C_1$-$C_6$haloalkoxy, —C(O)$NH_2$, —$SF_5$, or —$S(O)_pR$;
- $R^2$ is halo, cyano, $C_1$-$C_6$alkyl, $C_1$-$C_6$haloalkyl, nitro, hydroxyl, —C(O)$NR^aR^b$, $C_2$-$C_6$alkenyl, $C_2$-$C_6$alkynyl, —$S(O)_pR$, or —OR;
- $R^3$ is cyano, $C_1$-$C_6$alkyl, $C_1$-$C_6$haloalkyl, —C(O)$NR^aR^b$, $C_2$-$C_6$alkenyl, $C_2$-$C_6$alkynyl, $C_2$-$C_6$haloalkenyl, or $C_2$-$C_6$haloalkynyl;
- $R^4$ is hydrogen, $C_1$-$C_6$alkyl, $C_0$-$C_6$alkyl$C_3$-$C_6$cycloalkyl, —C(O)$R^5$, —C(S)$R^5$, —C(O)$NR^aR^5$, —C(O)C(O)$NR^aR^5$, —$S(O)_pR^c$, —$S(O)_2NR^aR^5$, —$C(NR^7)R^5$, —$C(NR^7)NR^aR^5$, $C_0$-$C_6$alkylphenyl, $C_0$-$C_6$alkylheteroaryl, or $C_0$-$C_6$alkylheterocycle;
- $R^5$ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;
- $R^6$ is hydrogen, $C_1$-$C_6$alkyl, hydroxyl, or $C_1$-$C_6$alkoxy;

R⁷ is hydrogen, $C_1$-$C_6$alkyl, hydroxyl, cyano, nitro, —S(O)$_p$R$^c$, or $C_1$-$C_6$alkoxy;

R is $C_1$-$C_6$alkyl or $C_3$-$C_6$cycloalkyl optionally substituted with at least one halo substituent;

R$^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

R$^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

R$^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R, —SCN, or —C(O)NR$^a$R$^b$;

each of R⁴ and R⁵ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, —S(O)$_p$R$^c$, —SH, —S(O)$_p$NR$^a$R$^b$, —NR$^a$R$^b$, —NR$^a$C(O)R$^b$, —SC(O)R, —SCN, or —C(O)NR$^a$R$^b$; and wherein each of R⁴ and R⁵ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =NR⁷, hydroxyl, hydroxyl$C_1$-$C_6$alkyl-, $C_1$-$C_6$alkoxy, $C_1$-$C_6$alkyl, $C_1$-$C_6$haloalkyl, —SH, —S(O)$_p$R, and $C_1$-$C_6$haloalkoxy;

n is the integer 0, 1, or 2, and when n is 2, each R² may be identical or different from each other; and p is the integer 0, 1, or 2;

stereoisomers thereof, and veterinarily acceptable salts thereof.

20. The method of claim 19 wherein the compound is administered topically, orally, or subcutaneously.

21. The method of claim 20 wherein said animal is a companion animal.

22. A process for the preparation of a compound of Formula (63)

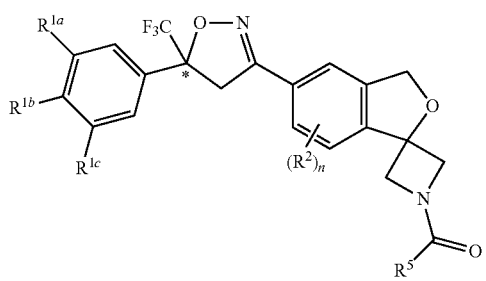

wherein

R$^{1a}$, R$^{1b}$, and R$^{1c}$ are each independently hydrogen, halo, hydroxyl, cyano, nitro, $C_1$-$C_6$alkyl, $C_1$-$C_6$haloalkyl, $C_1$-$C_6$alkoxy, $C_0$-$C_3$alkyl$C_3$-$C_6$cycloalkyl, $C_1$-$C_6$haloalkoxy, —C(O)NH$_2$, —SF$_5$, or —S(O)$_p$R;

R² is halo, cyano, $C_1$-$C_6$alkyl, $C_1$-$C_6$haloalkyl, nitro, hydroxyl, —C(O)NR$^a$R$^b$, $C_2$-$C_6$alkenyl, $C_2$-$C_6$alkynyl, —S(O)$_p$R, or —OR;

R⁵ is hydrogen, $C_1$-$C_6$alkyl, $C_2$-$C_6$alkenyl, $C_0$-$C_6$alkyl$C_3$-$C_6$cycloalkyl, $C_0$-$C_6$alkylphenyl, $C_0$-$C_6$alkylheteroaryl, or $C_0$-$C_6$alkylheterocycle;

R⁷ is hydrogen, $C_1$-$C_6$alkyl, hydroxyl, cyano, nitro, —S(O)$_p$R$^c$, or $C_1$-$C_6$alkoxy;

R is $C_1$-$C_6$alkyl or $C_3$-$C_6$cycloalkyl optionally substituted with at least one halo substituent;

R$^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

R$^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

R$^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R, —SCN, or —C(O)NR$^a$R$^b$;

wherein R⁵ $C_1$-$C_6$alkyl or $C_0$-$C_6$alkyl$C_3$-$C_6$cycloalkyl moiety can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, $C_1$-$C_6$alkyl, hydroxyl$C_1$-$C_6$alkyl-, —S(O)$_p$R$^c$, —SH, —S(O)$_p$NR$^a$R$^b$, —NR$^a$R$^b$, —NR$^a$C(O)R$^b$, —SC(O)R, —SCN, or —C(O)NR$^a$R$^b$; and wherein R⁵ $C_0$-$C_6$alkylphenyl, $C_0$-$C_6$alkylheteroaryl, or $C_0$-$C_6$alkylheterocycle moiety can be further optionally substituted with at least one substituent selected from cyano, halo, oxo, =S, =NR⁷, hydroxyl, hydroxyl$C_1$-$C_6$alkyl-, $C_1$-$C_6$alkoxy, $C_1$-$C_6$alkyl, $C_1$-$C_6$haloalkyl, —SH, —S(O)$_p$R, and $C_1$-$C_6$haloalkoxy;

n is the integer 0, 1, or 2, and when n is 2, each R² may be identical or different from each other;

p is the integer 0, 1, or 2; and

* depicts a chiral center, stereoisomers thereof, and veterinarily acceptable salts thereof;

said process comprising, optionally in a solvent, a) metallating an iodobromobenzyl derivative of Formula 57 with a Grignard reagent or halogen-metal exchange with an alkyllithium and reacting with a protected azetidinone in a one-pot process or in a step-wise process to provide a compound of Formula 58, wherein Y² is bromine, chlorine, iodine, hydroxyl, or a sulfonate leaving group;

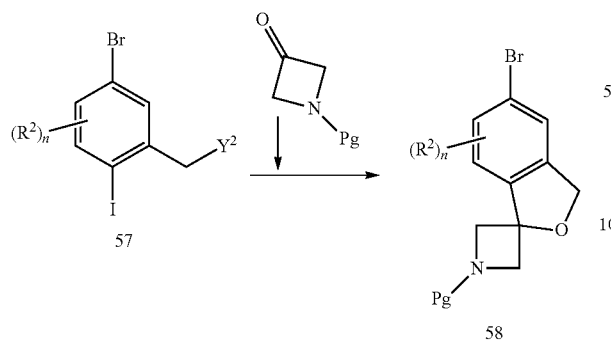

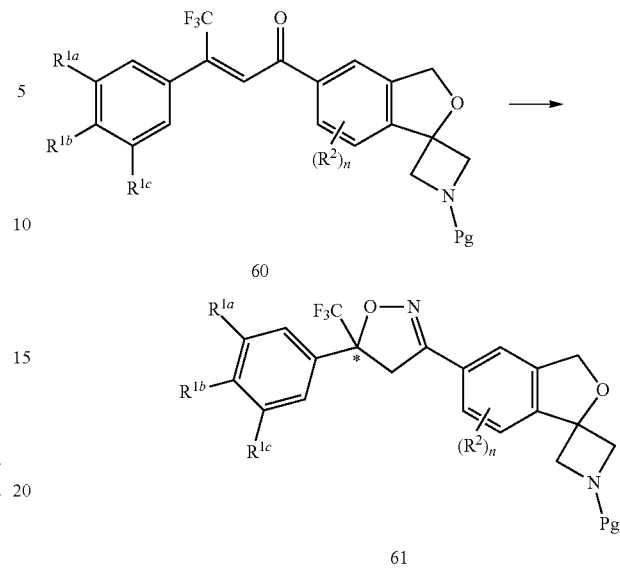

b) palladium catalyzed condensation of a compound of Formula 58 with a vinyl ether to provide a compound of Formula 59, wherein $R^8$ is a $C_1$-$C_6$alkyl;

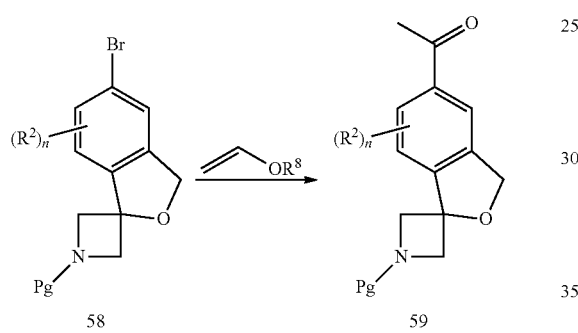

c) condensation of a compound of Formula 59 with a substituted trifluoroacetophenone of Formula 56 to provide a compound of Formula 60;

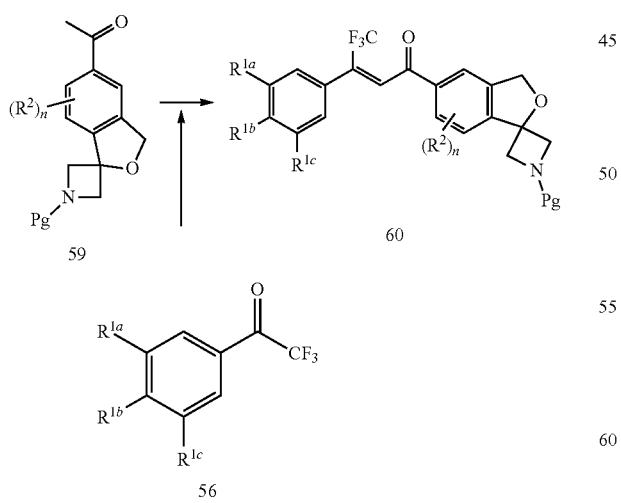

d) addition of hydroxylamine to a compound of Formula 60 and cyclization in the presence of a quinine based chiral catalyst to provide a compound of Formula 61;

e) removal of the azetidine protecting group of the compound of Formula 61 to provide a compound of Formula 62; and

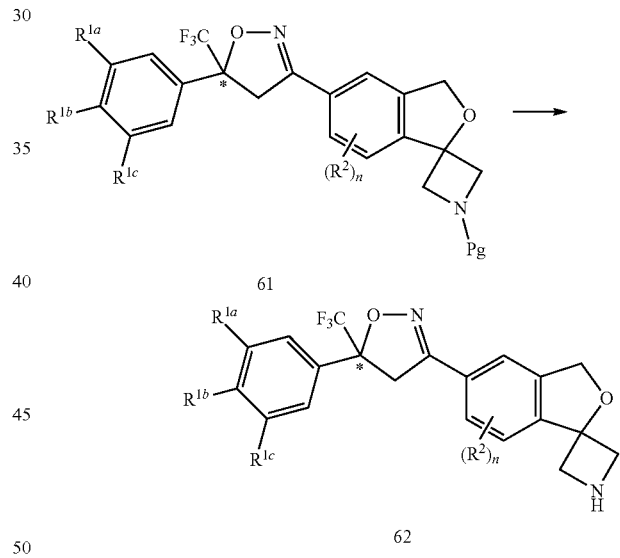

f) coupling the compound of Formula 62 with an acid or acid chloride under standard amide formation conditions to provide a compound of Formula 63;

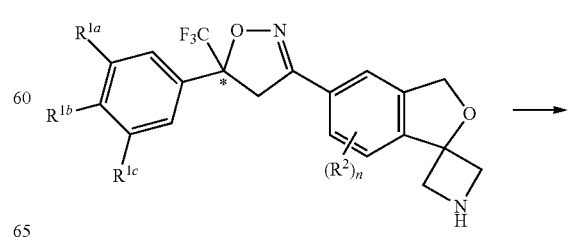

-continued

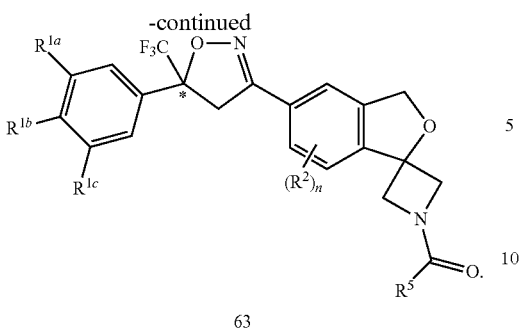

63

23. The process of claim 22 wherein
$R^{1a}$, $R^{1b}$, and $R^{1c}$ are each independently hydrogen, halo, or $C_1$-$C_6$haloalkyl;
$R^5$ is $C_1$-$C_6$alkyl, $C_0$-$C_6$alkyl$C_3$-$C_6$cycloalkyl, $C_0$-$C_6$alkylheteroaryl, or $C_0$-$C_6$alkylheterocycle;
wherein $R^5$ $C_1$-$C_6$alkyl or $C_0$-$C_6$alkyl$C_3$-$C_6$cycloalkyl moiety can be optionally and independently substituted by at least one substituent selected from halo, hydroxyl, hydroxyl$C_1$-$C_6$alkyl-, $C_1$-$C_6$haloalkyl, $C_1$-$C_6$alkyl, or —S(O)$_p$$R^c$; and
wherein $R^5$ $C_0$-$C_6$alkylheteroaryl or $C_0$-$C_6$alkylheterocycle moiety can be further optionally substituted with at least one substituent selected from oxo, hydroxyl, hydroxy$C_1$-$C_6$alkyl-, $C_1$-$C_6$alkyl, or $C_1$-$C_6$haloalkyl;
$R^c$ is $C_1$-$C_6$alkyl;
n is the integer 0; and
p is the integer 0, 1, or 2;
stereoisomers thereof, and veterinarily acceptable salts thereof.

24. The process of claim 23 wherein
$R^{1a}$, $R^{1b}$, and $R^{1c}$ are each independently hydrogen, chloro, fluoro, bromo, or trifluoromethyl;
$R^5$ is methyl, ethyl, propyl, isopropyl, butyl, isobutyl, t-butyl, cyclopropyl, or cyclobutyl, wherein each substituent can be optionally and independently substituted by at least one substituent selected from halo, hydroxyl, $C_1$-$C_6$haloalkyl, $C_1$-$C_6$alkyl, or —S(O)$_p$$R^c$; or $R^5$ is thietanyl, pyrazolyl, or —CH$_2$pyrazolyl, wherein each substituent can be further optionally substituted with at least one substituent selected from oxo, or $C_1$-$C_6$alkyl; and
$R^c$ is methyl or ethyl;
stereoisomers thereof, and veterinarily acceptable salts thereof.

25. The process of claim 24 wherein
$R^{1a}$ and $R^{1c}$ are each chloro, $R^{1b}$ is fluoro;
$R^5$ is —CH$_2$S(O)$_2$CH$_3$;
stereoisomers thereof, and veterinarily acceptable salts thereof.

26. The process of claim 22, comprising, optionally in a solvent, wherein the iodobromobenzyl derivative is 4-bromo-2-(chloromethyl)-1-iodobenzene and the protected azetidinone is 3-oxooazetidine-1-carboxylic acid tert-butyl ester or 1-benzhydrylazetidin-3-one.

27. A compound selected from the group consisting of:
tert-butyl 5'-bromo-3'H-spiro[azetidine-3,1'-isobenzofuran]-1-carboxylate;
1-benzhydryl-5'-bromo-3'H-spiro[azetidine-3,1'-isobenzofuran];
tert-butyl 5'-acetyl-3'H-spiro[azetidine-3,1'-isobenzofuran]-1-carboxylate;
1-(1-benzhydryl-3'H-spiro[azetidine-3,1'-isobenzofuran]-5'-yl)ethanone;

tert-butyl 5'-(3-(3,5-dichloro-4-fluorophenyl)-4,4,4-trifluorobut-2-enoyl)-3'H-spiro[azetidine-3,1'-isobenzofuran]-1-carboxylate;
(R)-tert-butyl 5'-(5-(3,5-dichloro-4-fluorophenyl)-5-(trifluoromethyl)-4,5-dihydroisoxazol-3-yl)-3'H-spiro[azetidine-3,1'-isobenzofuran]-1-carboxylate;
(S)-tert-butyl 5'-(5-(3,5-dichloro-4-fluorophenyl)-5-(trifluoromethyl)-4,5-dihydroisoxazol-3-yl)-3'H-spiro[azetidine-3,1'-isobenzofuran]-1-carboxylate;
(E/Z)-1-(1-benzhydryl-3'H-spiro[azetidine-3,1'-isobenzofuran]-5'-yl)-3-(3,5-dichloro-4-fluorophenyl)-4,4,4-trifluorobut-2-en-1-one;
tert-butyl 5'-(5-(3,5-dichloro-4-fluorophenyl)-5-(trifluoromethyl)-4,5-dihydroisoxazol-3-yl)-3'H-spiro[azetidine-3,1'-isobenzofuran]-1-carboxylate;
(R)-5'-(5-(3,5-dichloro-4-fluorophenyl)-5-(trifluoromethyl)-4,5-dihydroisoxazol-3-yl)-3'H-spiro[azetidine-3,1'-isobenzofuran]para-toluene sulfonate;
(S)-5'-(5-(3,5-dichloro-4-fluorophenyl)-5-(trifluoromethyl)-4,5-dihydroisoxazol-3-yl)-3'H-spiro[azetidine-3,1'-isobenzofuran]para-toluene sulfonate;
1-benzhydryl-5'-(5-(3,5-dichloro-4-fluorophenyl)-5-(trifluoromethyl)-4,5-dihydroisoxazol-3-yl)-3'H-spiro[azetidine-3,1'-isobenzofuran];
(R)-1-benzhydryl-5'-(5-(3,5-dichloro-4-fluorophenyl)-5-(trifluoromethyl)-4,5-dihydroisoxazol-3-yl)-3'H-spiro[azetidine-3,1'-isobenzofuran]
(S)-1-benzhydryl-5'-(5-(3,5-dichloro-4-fluorophenyl)-5-(trifluoromethyl)-4,5-dihydroisoxazol-3-yl)-3'H-spiro[azetidine-3,1'-isobenzofuran]; and
5'-(5-(3,5-dichloro-4-fluorophenyl)-5-(trifluoromethyl)-4,5-dihydroisoxazol-3-yl)-3'H-spiro[azetidine-3,1'-isobenzofuran]para-toluene sulfonate,
or a stereoisomer thereof, or a veterinarily acceptable salt thereof.

28. The compound of claim 14 which is 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-hydroxyethanone, or a stereoisomer thereof, or a veterinarily acceptable salt thereof.

29. The compound of claim 14 which is 2-cyclopropyl-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)ethanone, or a stereoisomer thereof, or a veterinarily acceptable salt thereof.

30. The compound of claim 14 which is 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)butan-1-one, or a stereoisomer thereof, or a veterinarily acceptable salt thereof.

31. The compound of claim 14 which is 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone; or a stereoisomer thereof, or a veterinarily acceptable salt thereof.

32. The compound of claim 14 which is (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone; or a veterinarily acceptable salt thereof.

33. The compound of claim 14 which is 1-(cyclopropanecarbonyl)-5'-(3,4,5-trichlorophenyl)-5-(trifluoromethyl)-4,5-dihydroisoxazol-3-yl)-3'H-spiro{azetidine-3,1'-isobenzofuran}-3'-one, or a stereoisomer thereof, or a veterinarily acceptable salt thereof.

34. The compound of claim 14 which is 5'-(5-(3,5-dichloro-4-fluorophenyl)-5-(trifluoromethyl)-4,5-dihydroisoxazol-3-yl)-1-propionyl-3'H-spiro[azetidine-3,1'-isobenzofuran]-3'-one, or a stereoisomer thereof, or a veterinarily acceptable salt thereof.

35. The compound of claim 14 which is (R)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethanone, or a veterinarily acceptable salt thereof.

36. The compound of claim 14 which is 1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-((trifluromethyl)thio)ethanone, or a stereoisomer thereof, or a veterinarily acceptable salt thereof.

\* \* \* \* \*

UNITED STATES PATENT AND TRADEMARK OFFICE
CERTIFICATE OF CORRECTION

PATENT NO. : 8,466,115 B2  
APPLICATION NO. : 13/414764  
DATED : June 18, 2013  
INVENTOR(S) : Curtis et al.

Page 1 of 2

It is certified that error appears in the above-identified patent and that said Letters Patent is hereby corrected as shown below:

In the Specification

Column 3, line 29, delete the variable R6 and it's defined attributes.

Column 75, lines 42-44, compound name of Preparation 9 should read:
"1-benzhydryl-3-(2-bromo-4-(5-(3,5-dichloro-4-fluorophenyl)-5-(trifluoromethyl)-4,5-dihydroisoxazol-3-yl)phenyl)azetidin-3-ol"

Column 76, lines 3-5, compound name of Preparation 10 should read:
"1-benzhydryl-5'-(5-(3,5-dichloro-4-fluorophenyl)-5-(trifluoromethyl)-4,5-dihydroisoxazol-3-yl)-3'H-spiro[azetidine-3,1'-isobenzofuran]-3'-one"

Column 76, lines 23-24, should read:
"solution of 1-benzhydryl-3-(2-bromo-4-(5-(3,5-dichloro-4-fluorophenyl)-5-(trifluoromethyl)-4,5-dihydroisoxazol-3-yl)"

Column 76, lines 42-44, compound name of Preparation 11 should read:
"1-benzhydryl-3-(2-hydroxymethyl-4-(5-(3,5-dichloro-4-fluorophenyl)-5-(trifluoromethyl)-4,5-dihydroisoxazol-3-yl)phenyl)azetidin-3-ol"

Column 76, lines 61-62, should read:
"To a solution of 1-benzhydryl-5'-(5-(3,5-dichloro-4-fluorophenyl)-5-(trifluoromethyl)-4,5-dihydroisoxazol-3-yl)-3'H-"

Column 77, lines 11-13, compound name of Preparation 12 should read:
"1-benzhydryl-5'-(5-(3,5-dichloro-4-fluorophenyl)-5-(trifluoromethyl)-4,5-dihydroisoxazol-3-yl)-3'H-spiro[azetidine-3,1'-isobenzofuran]"

Signed and Sealed this  
Seventh Day of October, 2014

Michelle K. Lee  
*Deputy Director of the United States Patent and Trademark Office*

CERTIFICATE OF CORRECTION (continued)  Page 2 of 2
U.S. Pat. No. 8,466,115 B2

Column 77, lines 30-31, should read:
"A solution of 1-benzhydryl-3-(2-hydroxymethyl-4-(5-(3,5-dichloro-4-fluorophenyl)-5-(trifluoromethyl)-4,5-dihydroisox-"

Column 77, lines 44-46, compound name of Preparation 13 should read:
"5'-(5-(3,5-dichloro-4-fluorophenyl)-5-(trifluoromethyl)-4,5-dihydroisoxazol-3-yl)-3'H-spiro[azetidine-3,1'-isobenzofuran]"

Column 77, lines 61-62, should read: "To a solution of 1-benzhydryl-5'-(5-(3,5-dichloro-4-fluorophenyl)-5-(trifluoromethyl)-4,5-dihydroisoxazol-3-yl)-3'H-"

In the Claims

Column 106, line 14, Claim 1, delete the variable R6 and it's defined attributes.

Column 110, line 47, Claim 12, should read: "dine-3,1'-isobenzofuran]-3'-one;"

Column 111, line 6, Claim 12, should read: "dine-3,1'-isobenzofuran]-3'-one;"

UNITED STATES PATENT AND TRADEMARK OFFICE
CERTIFICATE OF CORRECTION

Page 1 of 3

PATENT NO. : 8,466,115 B2
APPLICATION NO. : 13/414764
DATED : June 18, 2013
INVENTOR(S) : Curtis et al.

It is certified that error appears in the above-identified patent and that said Letters Patent is hereby corrected as shown below:

In the Specification

Column 13, lines 30-40, should read:

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

(R)-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

(S)-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

Column 17, lines 45-55, should read:

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

(R)-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

(S)-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

Column 19, lines 61-67 through Column 20, lines 1-4, should read:

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

Signed and Sealed this
Twenty-fifth Day of August, 2015

Michelle K. Lee
*Director of the United States Patent and Trademark Office*

CERTIFICATE OF CORRECTION (continued)
U.S. Pat. No. 8,466,115 B2

(R)-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

(S)-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

Column 100, lines 61-64, should read:

Chiral-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone (49a);

In the Claims

Column 113, lines 21-31, should read:

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

(R)-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

(S)-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

Column 116, lines 43-53, should read:

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

(R)-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

(S)-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

Column 118, lines 7-18, should read:

(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

(R)-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;

(S)-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)(1,1-dioxidothietan-3-yl)methanone;